(12) United States Patent
Ando et al.

(10) Patent No.: US 6,603,008 B1
(45) Date of Patent: Aug. 5, 2003

(54) SULFAMOYLHELEROARYL PYRAZOLE COMPOUNDS AS ANTI-INFLAMMATORY/ ANALGESIC AGENTS

(75) Inventors: Kazuo Ando, Aichi-Ken (JP); Kiyoshi Kawamura, Aichi (JP)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 09/723,661

(22) Filed: Nov. 28, 2000

Related U.S. Application Data
(60) Provisional application No. 60/168,889, filed on Dec. 3, 1999.

(51) Int. Cl.[7] .............................................. C07D 401/04
(52) U.S. Cl. .................... 546/269.7; 514/341; 514/342; 514/340; 546/271.4; 546/275.4
(58) Field of Search ............................ 546/269.7, 271.4, 546/275.4; 514/340, 341, 342

(56) References Cited

FOREIGN PATENT DOCUMENTS

| EP | 418845 | 3/1991 |
|----|--------|--------|
| EP | 554829 | 8/1993 |
| WO | 9500501 | 1/1995 |
| WO | 9515315 | 6/1995 |
| WO | 9515316 | 6/1995 |
| WO | 9515317 | 6/1995 |
| WO | 9515318 | 6/1995 |
| WO | 9603387 | 2/1996 |
| WO | 9603392 | 2/1996 |
| WO | 9608482 | 3/1996 |
| WO | 9619469 | 6/1996 |
| WO | 9636623 | 11/1996 |
| WO | 9711704 | 4/1997 |
| WO | 9713755 | 4/1997 |
| WO | 9714691 | 5/1997 |
| WO | 9716435 | 5/1997 |

OTHER PUBLICATIONS

CA 135:33475, Cheng et al. 2001.*
CA 135:19659, Ando et al. 2001.*
Vane, J.R.; Mitchell, J. A.; Appleton, I.; Tomlinson, A.; Bishop–Bailey, D.; Croxtoll, J.;Willoughby, D. A. *Proc. Natl. Acad. Sci. USA*, 1994, 91, 2046.

\* cited by examiner

*Primary Examiner*—Jane Fan
(74) *Attorney, Agent, or Firm*—Peter C. Richardson; Gregg C. Benson; Lance Y. Liu

(57) ABSTRACT

This invention relates to a compound of the formula:

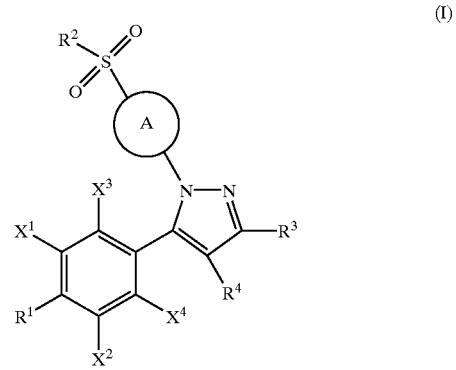

or a pharmaceutically acceptable salt thereof, wherein A and $R^1$ are each an optionally substituted 5 to 6-membered heteroaryl, wherein the heteroaryl is optionally fused to a carbocyclic ring or 5 to 6-heteroaryl; $R^2$ is $NH_2$; $R^3$ and $R^4$ are each hydrogen, halo, $(C_1–C_4)$alkyl optionally substituted with halo and the like; and $X^1$ to $X^4$ are each hydrogen, halo, hydroxy, $(C_1–C_4)$alkyl optionally substituted with halo and the like. These compounds have COX-2 inhibiting activity and thus useful for treating or preventing inflammation or other COX-2 related diseases.

3 Claims, No Drawings

SULFAMOYLHETEROARYL PYRAZOLE COMPOUNDS AS ANTI-INFLAMMATORY/ANALGESIC AGENTS

This application claims the benefit of U.S. Provisional No. 60/168,889, filed on Dec. 3, 1999.

BACKGROUND OF THE INVENTION

This invention relates to sulfamoylheteroaryl pyrazole derivatives and methods of treatment and pharmaceutical compositions for the treatment of cyclooxygenase mediated diseases. The compounds of this invention inhibit the biosynthesis of prostaglandins by intervention of the action of the enzyme cyclooxygenase on arachidonic acid, and are therefore useful in the treatment or alleviation of inflammation and other inflammation associated disorders, such as arthritis, neurodegeneration and colon cancer, in mammals, preferably humans, dogs, cats or livestock.

Nonsteroidal anti-inflammatory drugs (NSAIDs) are widely used in treating pain and the signs and symptoms of arthritis because of their analgesic and anti-inflammatory activity. It is accepted that common NSAIDs work by blocking the activity of cyclooxygenase (COX), also known as prostaglandin G/H synthase (PGHS), the enzyme that converts arachidonic acid into prostanoids. Prostaglandins, especially prostaglandin $E_2$ ($PGE_2$), which is the predominant eicosanoid detected in inflammation conditions, are mediators of pain, fever and other symptoms associated with inflammation. Inhibition of the biosynthesis of prostaglandins has been a therapeutic target of anti-inflammatory drug discovery. The therapeutic use of conventional NSAIDs is, however, limited due to drug associated side effects, including life threatening ulceration and renal toxicity. An alternative to NSAIDs is the use of corticosteriods, however, long term therapy can also result in severe side effects.

The use of NSAIDs in the treatment or alleviation of inflammation and other inflammation associated disorders in dogs and cats has been more limited than that in humans: e.g., only three such NSAIDs have been approved by the Food and Drug Administration, Committee on Veterinary Medicine (FDA/CVM), for use in dogs in the United States, i.e., ETOGESIC® (etodolac), ARQUEL® (meclofenamic acid) and RIMADYL® (carprofen). Consequently, there is less experience and knowledge in veterinary medicine about safety and efficacy issues surrounding the use of NSAIDs in dogs. In veterinary medicine, for example, the most common indication for NSAIDs is the treatment of degenerative joint disease (DJD), which in dogs often results from a variety of developmental diseases, e.g., hip dysplasia and osteochondrosis, as well as from traumatic injuries to joints. In addition to the treatment of chronic pain and inflammation, NSAIDs are also useful in dogs for treating post-surgical acute pain, as well as for treating clinical signs associated with osteoarthritis.

Two forms of COX are now known, a constitutive isoform (COX-1) and an inducible isoform (COX-2) of which expression is upregulated at sites of inflammation (Vane, J. R.; Mitchell, J. A.; Appleton, I.; Tomlinson, A.; Bishop-Bailey, D.; Croxtoll, J.; Willoughby, D. A. *Proc. Natl. Acad. Sci. USA*, 1994, 91, 2046). COX-1 is thought to play a physiological role and to be responsible for gastrointestinal and renal protection. On the other hand, COX-2 appears to play a pathological role and is believed to be the predominant isoform present in inflammation conditions. A pathological role for prostaglandins has been implicated in a number of human disease states including rheumatoid arthritis and osteoarthritis, pyrexia, asthma, bone resorption, cardiovascular diseases, dysmenorrhea, premature labour, nephritis, nephrosis, atherosclerosis, hypotension, shock, pain, cancer, and Alzheimer disease. It is believed that compounds that would selectively inhibit the biosynthesis of prostaglandins by intervention of activity of the enzyme COX-2 on arachidonic acid would provide alternate therapy to the use of conventional NSAIDs or corticosteriods in that such compounds would exert anti-inflammatory effects without the adverse side effects associated with COX-1 inhibition.

A variety of sulfonylbenzene compounds which inhibit COX have been disclosed in patent publications (WO 97/16435, WO 97/14691, WO 96/19469, WO 96/36623, WO 96/03392, WO 96/03387, WO 97/727181, WO 96/936617, WO 96/19469, WO 96/08482, WO 95/00501, WO 95/15315, WO 95/15316, WO 95/15317, WO 95/15318, WO 97/13755, EP 0799523, EP 418845, and EP 554829). Especially, International Publication Number WO 97/11704 discloses pyrazole compounds substituted with optionally substituted aryl.

SUMMARY OF THE INVENTION

The present invention provides a compound of the following formula:

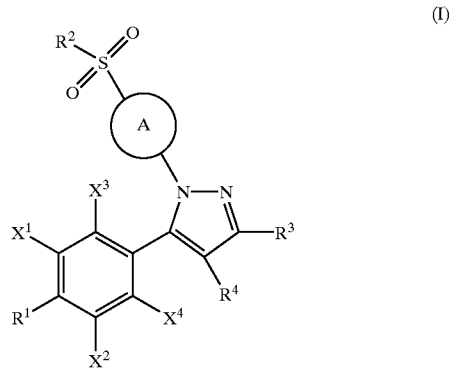

or a pharmaceutically acceptable salt thereof, wherein
A is selected from the group consisting of
a) (5- to 6-membered)-heteroaryl containing 1 to 4 ring heteroatoms independently selected from —N═, —NR'—, —O—, or —S—, wherein said heteroaryl is optionally substituted with 1–3 substituents independently selected from the group consisting of halo, hydroxy, cyano, mercapto, carboxy, nitro, $(C_1-C_4)$ alkyl, $(C_2-C_4)$alkenyl, $(C_2-C_4)$alkynyl, $(C_1-C_4)$ alkoxy, $(C_1-C_4)$alkyl-S—, amino, $(C_1-C_4)$ alkylamino, di[$(C_1-C_4)$alkyl]amino, amido, $(C_1-C_4)$ alkylamido, di[$(C_1-C_4)$alkyl]amido, $(C_1-C_4)$alkyl-(C═O)—O—, $(C_1-C_4)$alkyl-(C═O)—N(R')—, formyl, $(C_1-C_4)$alkyl-(C═O)— and $(C_1-C_4)$ alkoxy-(C═O)—; wherein R' is hydrogen or $(C_1-C_4)$alkyl; wherein each of said $(C_1-C_4)$alkyl may optionally be substituted with 1 to 3 substituents independently selected from the group consisting of halo, hydroxy, cyano, mercapto, carboxy, nitro, $(C_1-C_4)$alkyl, $(C_2-C_4)$alkenyl, $(C_2-C_4)$alkynyl, $(C_1-C_4)$alkoxy, $(C_1-C_4)$alkyl-S—, amino, $(C_1-C_4)$ alkylamino, di[$(C_1-C_4)$alkyl]amino, amido, $(C_1-C_4)$ alkylamido, di[$(C_1-C_4)$alkyl]amido, $(C_1-C_4)$alkyl-(C═O)—O—, $(C_1-C_4)$alkyl-(C═O)—N(R')—, formyl, $(C_1-C_4)$alkyl-(C═O)— and $(C_1-C_4)$ alkoxy-(C═O)—;

b) (5- to 6-membered)-heteroaryl containing 1 to 2 ring heteroatoms independently selected from the group consisting of —N=, —NR'—, —S— or —O—; wherein said heteroaryl is fused to a saturated, partially saturated or aromatic (5- to 7-membered)-carbocyclic ring; wherein either of said (5- to 6-membered)-heteroaryl ring or said fused saturated, partially saturated or aromatic (5- to 7-membered)-carbocyclic ring may optionally be substituted with 1 to 2 substituents per ring, wherein said substituents are independently selected from the group consisting of halo, hydroxy, cyano, mercapto, carboxy, nitro, $(C_1-C_4)$alkyl, $(C_2-C_4)$alkenyl, $(C_2-C_4)$alkynyl, $(C_1-C_4)$alkoxy, $(C_1-C_4)$alkyl-S—, amino, $(C_1-C_4)$alkylamino, di[$(C_1-C_4)$alkyl]amino, amido, $(C_1-C_4)$alkylamido, di[$(C_1-C_4)$alkyl]amido, $(C_1-C_4)$alkyl-(C=O)—O—, $(C_1-C_4)$alkyl-(C=O)—N(R')—, formyl, $(C_1-C_4)$alkyl-(C=O)— and $(C_1-C_4)$alkoxy-(C=O)—; wherein R' is hydrogen or $(C_1-C_4)$alkyl; wherein each of said $(C_1-C_4)$alkyl is optionally substituted with 1 to 3 substituents independently selected from the group consisting of halo, hydroxy, cyano, mercapto, carboxy, nitro, $(C_1-C_4)$alkyl, $(C_2-C_4)$alkenyl, $(C_2-C_4)$alkynyl, $(C_1-C_4)$alkoxy, $(C_1-C_4)$alkyl-S—, amino, $(C_1-C_4)$alkylamino, di[$(C_1-C_4)$alkyl]amino, amido, $(C_1-C_4)$alkylamido, di[$(C_1-C_4)$alkyl]amido, $(C_1-C_4)$alkyl-(C=O)—O—, $(C_1-C_4)$alkyl-(C=O)—N(R')—, formyl, $(C_1-C_4)$alkyl-(C=O)— and $(C_1-C_4)$alkoxy-(C=O)—; and c) (5- to 6-membered)-heteroaryl containing 1 to 2 ring heteroatoms independently selected from the group consisting of —N=, —NR'—, —S—, or —O—; wherein said heteroaryl is fused to a (5- to 6-membered)-heteroaryl containing 1 to 2 ring heteroatoms independently selected from the group consisting of —N=, —NR'—, —S— or —O—; wherein either of said (5- to 6-membered)-heteroaryl or said fused (5- to 6-membered)-heteroaryl is optionally substituted with one to two substituents per ring, wherein said substituents are independently selected from the group consisting of halo, hydroxy, cyano, mercapto, carboxy, nitro, $(C_1-C_4)$alkyl, $(C_2-C_4)$alkenyl, $(C_2-C_4)$alkynyl, $(C_1-C_4)$alkoxy, $(C_1-C_4)$alkyl-S—, amino, $(C_1-C_4)$alkylamino, di[$(C_1-C_4)$alkyl]amino, amido, $(C_1-C_4)$alkylamido, di[$(C_1-C_4)$alkyl]amido, $(C_1-C_4)$alkyl-(C=O)—O—, $(C_1-C_4)$alkyl-(C=O)—N(R')—, formyl, $(C_1-C_4)$alkyl-(C=O)— and $(C_1-,C_4)$alkoxy-(C=O)—; wherein R' is hydrogen or $(C_1-C_4)$alkyl; wherein each of said $(C_1-C_4)$alkyl may optionally be substituted with 1 to 3 substituents independently selected from the group consisting of halo, hydroxy, cyano, mercapto, carboxy, nitro, $(C_1-C_4)$alkyl, $(C_2-C_4)$alkenyl, $(C_2-C_4)$alkynyl, $(C_1-C_4)$alkoxy, $(C_1-C_4)$alkyl-S—, amino, $(C_1-C_4)$alkylamino, di[$(C_1-C_4)$alkyl]amino, amido, $(C_1-C_4)$alkylamido, di[$(C_1-C_4)$alkyl]amido, $(C_1-C_4)$alkyl-(C=O)—O—, $(C_1-C_4)$alkyl-(C=O)—N(R')—, formyl, $(C_1-C_4)$alkyl-(C=O)— and $(C_1-,C_4)$alkoxy-(C=O)—;

$R^1$ is selected from the group consisting of a) (5- to 6-membered)-heteroaryl containing 1 to 4 ring heteroatoms independently selected from —N=, —NR—, —O—, or —S—, wherein said heteroaryl is optionally substituted with 1–3 substituents independently selected from the group consisting of halo, hydroxy, cyano, mercapto, carboxy, nitro, $(C_1-C_4)$alkyl, $(C_2-C_4)$alkenyl, $(C_2-C_4)$alkynyl, $(C_1-C_4)$alkoxy, $(C_1-C_4)$alkyl-S—, amino, $(C_1-C_4)$alkylamino, di[$(C_1-C_4)$alkyl]amino, amido, $(C_1-C_4)$alkylamido, di[$(C_1-C_4)$alkyl]amido, $(C_1-C_4)$alkyl-(C=O)—O—, $(C_1-C_4)$alkyl-(C=O)—N(R')—, formyl, $(C_1-C_4)$alkyl-(C=O)— and $(C_1-C_4)$alkoxy-(C=O)—; wherein R' is hydrogen or $(C_1-C_4)$alkyl; wherein each of said $(C_1-C_4)$alkyl is optionally substituted with 1 to 3 substituents independently selected from the group consisting of halo, hydroxy, cyano, mercapto, carboxy, nitro, $(C_1-C_4)$alkyl, $(C_2-C_4)$alkenyl, $(C_2-C_4)$alkynyl, $(C_1-C_4)$alkoxy, $(C_1-C_4)$alkyl-S—, amino, $(C_1-C_4)$alkylamino, di[$(C_1-C_4)$alkyl]amino, amido, $(C_1-C_4)$alkylamido, di[$(C_1-C_4)$alkyl]amido, $(C_1-C_4)$alkyl-(C=O)—O—, $(C_1-C_4)$alkyl-(C=O)—N(R')—, formyl, $(C_1-C_4)$alkyl-(C=O)— and $(C_1-C_4)$alkoxy-(C=O)—;

b) (5- to 6-membered)-heteroaryl containing 1 to 2 ring heteroatoms independently selected from the group consisting of —N=, —NR'—, —S— or —O—; wherein said heteroaryl is fused to a saturated, partially saturated or aromatic (5- to 7-membered)-carbocyclic ring; wherein either of said (5- to 6-membered)-heteroaryl ring or said fused saturated, partially saturated or aromatic (5- to 7-membered)-carbocyclic ring is optionally substituted with 1 to 2 substituents per ring, wherein said substituents are independently selected from the group consisting of halo, hydroxy, cyano, mercapto, carboxy, nitro, $(C_1-C_4)$alkyl, $(C_2-C_4)$alkenyl, $(C_2-C_4)$alkynyl, $(C_1-C_4)$alkoxy, $(C_1-C_4)$alkyl-S—, amino, $(C_1-C_4)$alkylamino, di[$(C_1-C_4)$alkyl]amino, amido, $(C_1-C_4)$alkylamido, di[$(C_1-C_4)$alkyl]amido, $(C_1-C_4)$alkyl-(C=O)—O—, $(C_1-C_4)$alkyl-(C=O)—N(R')—, formyl, $(C_1-C_4)$alkyl-(C=O)— and $(C_1-C_4)$alkoxy-(C=O)—; wherein R' is hydrogen or $(C_1-C_4)$alkyl; wherein each of said $(C_1-C_4)$alkyl is optionally substituted with 1 to 3 substituents independently selected from the group consisting of halo, hydroxy, cyano, mercapto, carboxy, nitro, $(C_1-C_4)$alkyl, $(C_2-C_4)$alkenyl, $(C_2-C_4)$alkynyl, $(C_1-C_4)$alkoxy, $(C_1-C_4)$alkyl-S—, amino, $(C_1-C_4)$alkylamino, di[$(C_1-C_4)$alkyl]amino, amido, $(C_1-C_4)$alkylamido, di[$(C_1-C_4)$alkyl]amido, $(C_1-C_4)$alkyl-(C=O)—O—, $(C_1-C_4)$alkyl-(C=O)—N(R')—, formyl, $(C_1-C_4)$alkyl-(C=O)— and $(C_1-C_4)$alkoxy-(C=O)—; and c) (5- to 6-membered)-heteroaryl containing 1 to 2 ring heteroatoms independently selected from the group consisting of —N=, —NR'—, —S—, or —O—; wherein said heteroaryl is fused to a (5- to 6-membered)-heteroaryl containing 1 to 2 ring heteroatoms independently selected from the group consisting of —N=, —NR'—, —S— or —O—; wherein either of said (5- to 6-membered)-heteroaryl or said fused (5- to 6-membered)-heteroaryl is optionally substituted with one to two substituents per ring, wherein said substituents are independently selected from the group consisting of halo, hydroxy, cyano, mercapto, carboxy, nitro, $(C_1-C_4)$alkyl, $(C_2-C_4)$alkenyl, $(C_2-C_4)$alkynyl, $(C_1-C_4)$alkoxy, $(C_1-C_4)$alkyl-S—, amino, $(C_1-C_4)$alkylamino, di[$(C_1-C_4)$alkyl]amino, amido, $(C_1-C_4)$alkylamido, di[$(C_1-C_4)$alkyl]amido, $(C_1-C_4)$alkyl-(C=O)—O—, $(C_1-C_4)$alkyl-(C=O)—N(R')—, formyl, $(C_1-C_4)$alkyl-$(C=O)$— and $(C_1-C_4)$alkoxy-$(C=O)$—; wherein R' is hydrogen or $(C_1-C_4)$alkyl; wherein each of said $(C_1-C_4)$alkyl is optionally substituted with 1 to 3 substituents independently selected from the group consisting of halo, hydroxy, cyano, mercapto, carboxy, nitro, $(C_1-C_4)$alkyl, $(C_2-C_4)$alkenyl, $(C_2-C_4)$alkynyl, $(C_1-C_4)$alkoxy, $(C_1-C_4)$alkyl-S—, amino, $(C_1-C_4)$alkylamino, di[$(C_1-C_4)$alkyl]amino, amido, $(C_1-C_4)$alkylamido, di[$(C_1-C_4)$alkyl]amido, $(C_1-C_4)$alkyl-$(C=O)$—O—, $(C_1-C_4)$alkyl-$(C=O)$—N(R')—, formyl, $(C_1-C_4)$alkyl-$(C=O)$— and $(C_1-C_4)$alkoxy-$(C=O)$—;

$R^2$ is $NH_2$;

$R^3$ and $R^4$ are independently selected from the group consisting of hydrogen, halo, $(C_1-C_4)$alkyl, $(C_2-C_4)$alkenyl, $(C_1-C_4)$alkoxy, $(C_1-C_4)$alkyl-$(C=O)$—, cyano, nitro, carboxy, $(C_1-C_4)$alkoxy-$(C=O)$—, amino-$(C=O)$—, $(C_1-C_4)$alkyl-amino-$(C=O)$—, di[$(C_1-C_4)$alkyl]-amino-$(C=O)$—, N-[$(C_1-C_4)$alkyl]—N-phenyl-amino-$(C=O)$—, N-[$(C_1-C_4)$alkyl]-N-[(5- to 6-membered)-heteroaryl]-amino-$(C=O)$—, wherein said (5- to 6—)membered heteroaryl contains 1 to 4 heteroatoms independently selected from —N=, —NR'—, —O— and —S—; wherein each of said $(C_1-C_4)$alkyl is optionally substituted with 1 to 3 substituents independently selected from the group consisting of halo, hydroxy, cyano, phenyl, $(C_1-C_4)$alkoxy and (5- to 6-membered)-heteroaryl containing 1 to 4 heteroatoms independently selected from —N=, —NR'—, —O— and —S—; wherein each of said R' is independently hydrogen or $(C_1-C_4)$alkyl; and $X^1$, $X^2$, $X^3$ and $X^4$ are independently selected from the group consisting of hydrogen, halo, hydroxy, cyano, mercapto, carboxy, nitro, $(C_1-C_4)$alkyl, $(C_1-C_4)$alkoxy, $(C_1-C_4)$alkyl-S—, $(C_1-C_4)$alkyl-amino-, di[$(C_1-C_4)$alkyl]-amino-, $(C_1-C_4)$alkyl-$(C=O)$—, $(C_1-C_4)$alkoxy-$(C=O)$— and amino-C$(=O)$—; wherein each said $(C_1-C_4)$alkyl is optionally substituted with 1 to 3 substituents independently selected from the group consisting of halo, amino, $(C_1-C_4)$alkyl-amino-, di[$(C_1-C_4)$alkyl]-amino-, hydroxy, carboxy, amino-$(C=O)$—, $(C_1-C_4)$alkyl-amino-C$(=O)$—, di[$(C_1-C_4)$alkyl]-amino-C$(=O)$—, mercapto, $(C_1-C_4)$alkyl-S— and $(C_1-C_4)$alkoxy-$(C=O)$—.

The present invention also relates to the pharmaceutically acceptable acid addition salts of compounds of the formula I. The acids which are used to prepare the pharmaceutically acceptable acid addition salts of the aforementioned base compounds of this invention are those which form non-toxic acid addition salts, i.e., salts containing pharmacologically acceptable anions, such as the hydrochloride, hydrobromide, hydroiodide, nitrate, sulfate, bisulfate, phosphate, acid phosphate, acetate, lactate, citrate, acid citrate, tartrate, bitartrate, succinate, maleate, fumarate, gluconate, saccharate, benzoate, methanesulfonate, ethanesulfonate, benzenesulfonate, p-toluenesulfonate and pamoate [i.e., 1,1'-methylene-bis-(2-hydroxy-3-naphthoate)]salts.

The invention also relates to base addition salts of formula I. The chemical bases that may be used as reagents to prepare pharmaceutically acceptable base salts of those compounds of formula I that are acidic in nature are those that form non-toxic base salts with such compounds. Such non-toxic base salts include, but are not limited to those derived from such pharmacologically acceptable cations such as alkali metal cations (e.g., potassium and sodium) and alkaline earth metal cations (e.g., calcium and magnesium), ammonium or water-soluble amine addition salts such as N-methylglucamine-(meglumine), and the lower alkanolammonium and other base salts of pharmaceutically acceptable organic amines.

The compounds of the invention may also exist in different tautomeric forms. This invention relates to all tautomers of formula I.

Certain compounds of the invention described herein contain one or more asymmetric centers and are capable of existing in various stereoisomeric forms. The present invention contemplates all such possible stereoisomers as well as their racemic and resolved, enantiomerically pure forms.

The term "treating", as used herein, refers to reversing, alleviating, inhibiting the progress of, or preventing the disorder or condition to which such term applies or one or more symptoms of such disorder or condition. The term "treatment", as used herein, refers to the act of treating, as "treating" is defined immediately above.

The term "livestock animals" as used herein refers to domesticated quadrupeds, which includes those being raised for meat and various byproducts, e.g., a bovine animal including cattle and other members of the genus Bos, a porcine animal including domestic swine and other members of the genus Sus, an ovine animal including sheep and other members of the genus Ovis, domestic goats and other members of the genus Capra; domesticated quadrupeds being raised for specialized tasks such as use as a beast of burden, e.g., an equine animal including domestic horses and other members of the family Equidae, genus Equus, or for searching and sentinel duty, e.g., a canine animal including domestic dogs and other members of the genes Canis; and domesticated quadrupeds being raised primarily for recreational purposes, e.g., members of Equus and Canis, as well as a feline animal including domestic cats and other members of the family Felidae, genus Felis.

"Companion animals" as used herein refers to cats and dogs. As used herein, the term "dog(s)" denotes any member of the species *Canis familiaris*, of which thee are a large number of different breeds. While laboratory determinations of biological activity may have been carried out using a particular breed, it is contemplated that the inhibitory compounds of the present invention will be found to be useful for treating pain and inflammation in any of these numerous breeds. Dogs represent a particularly prefered class of patients in that they are well known as being very susceptible to chronic inflammatory processes such as osteoarthritis and degenerative joint disease which in dogs often results from a variety of developmental diseases, e.g., hip dysplasia and osteochondrosis, as well as from traumatic injuries to joints Conventional NSAIDs, if used in canine therapy, have the potential for serious adverse gastrointestinal reactions and other adverse reactions including kidney and live toxicity. Gastrointestinal effects such as single or multiple ulcerations, including perforation and hemorrhage of the esophagus, stomach, duodenum or small and large intestine, are usually debilitating, but can often be severe or even fatal.

The subject invention also includes isotopically-labelled compounds, which are identical to those recited in Formula I, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, fluorine and chlorine, such as $^2H$, $^3H$, $^{13}C$, $^{14}C$, $^{15}N$, $^{18}O$, $^{17}O$, $^{31}P$, 32P, $^{35}$S, $^{18}$F, and $^{36}$Cl, respectively. Compounds of the present invention, prodrugs thereof, and pharmaceutically acceptable salts of said compounds or of said prodrugs which contain the aforementioned isotopes and/or other isotopes of other atoms are within the scope of this invention. Certain isotopically-labelled compounds of the present invention, for example those into which radioactive isotopes such as $^3$H and $^{14}$C are incorporated, are useful in drug and/or substrate tissue distribution assays. Tritiated, i.e., $^3$H, and carbon-14, i.e., $^{14}$C, isotopes are particularly preferred for their ease of preparation and detectability. Further, substitution with heavier isotopes such as deuterium, i.e., $^2$H, can afford certain therapeutic advantages resulting from greater metabolic stability, for example increased in vivo half-life or reduced dosage requirements and, hence, may be preferred in some circumstances. Isotopically labelled compounds of Formula I of this invention and prodrugs thereof can generally be prepared by carrying out the procedures disclosed in the Schemes and/or in the Examples and Preparations below, by substituting a readily available isotopically labelled reagent for a non-isotopically labelled reagent.

This invention also encompasses pharmaceutical compositions containing prodrugs of compounds of the formula I. This invention also encompasses methods of treating or preventing disorders that can be treated or prevented by the inhibition of matrix metalloproteinases or the inhibition of mammalian reprolysin comprising administering prodrugs of compounds of the formula I. Compounds of formula I having free amino, amido, hydroxy, hydroxamic acid, sulfonamide or carboxylic groups can be converted into prodrugs. Prodrugs include compounds wherein an amino acid residue, or a polypeptide chain of two or more (e.g., two, three or four) amino acid residues which are covalently joined through peptide bonds to free amino, hydroxy or carboxylic acid groups of compounds of formula I. The amino acid residues include the 20 naturally occurring amino acids commonly designated by three letter symbols and also include, 4-hydroxyproline, hydroxylysine, demosine, isodemosine, 3-methylhistidine, norvalin, beta-alanine, gamma-aminobutyric acid, citrulline, homocysteine, homoserine, ornithine and methionine sulfone. Prodrugs also include compounds wherein carbonates, carbamates, amides and alkyl esters are covalently bonded to the above substituents of formula I through the carbonyl carbon prodrug sidechain.

One of ordinary skill in the art will appreciate that the compounds of the invention are useful in treating a diverse array of diseases. One of ordinary skill in the art will also appreciate that when using the compounds of the invention in the treatment of a specific disease that the compounds of the invention may be combined with various existing therapeutic agents used for that disease.

For the treatment of rheumatoid arthritis, the compounds of the invention may be combined with agents such as TNF-α inhibitors such as anti-TNF monoclonal antibodies and TNF receptor immunoglobulin molecules (such as Enbrel®), low dose methotrexate, lefunimide, hydroxychloroquine, d-penicilamine, auranofin or parenteral or oral gold.

The compounds of the invention can also be used in combination with existing therapeutic agents for the treatment of osteoarthritis. Suitable agents to be used in combination include standard non-steroidal anti-inflammatory agents (hereinafter NSAID's) such as piroxicam, diclofenac, propionic acids such as naproxen, flurbiprofen, fenoprofen, ketoprofen and ibuprofen, fenamates such as mefenamic acid, indomethacin, sulindac; apazone, pyrazolones such as phenylbutazone, salicylates such as aspirin, COX-2 inhibitors such as celecoxib and rofecoxib, analgesics and intraarticular therapies such as corticosteroids and hyaluronic acids such as hyalgan and synvisc.

The active ingredient of the present invention may be administered in combination with inhibitors of other mediators of inflammation, comprising one or more members selected from the group consisting essentially of the classes of such inhibitors and examples thereof which include, matrix metalloproteinase inhibitors, aggrecanase inhibitors, TACE inhibitors, IL-1 processing and release inhibitors, ILra, $H_1$-receptor antagonists; kinin-$B_1$- and $B_2$-receptor antagonists; prostaglandin inhibitors such as PGD-, PGF- $PGI_2$-, and PGE-receptor antagonists; thromboxane $A_2$ (TXA2—) inhibitors; 5- and 12-lipoxygenase inhibitors; leukotriene $LTC_4$-, $LTD_4$/$LTE_4$-, and $LTB_4$-inhibitors; PAF-receptor antagonists; gold in the form of an aurothio group together with various hydrophilic groups; immunosuppressive agents, e.g., cyclosporine, azathioprine, and methotrexate; anti-inflammatory glucocorticoids; penicillamine; hydroxychloroquine; anti-gout agents, e.g., colchicine, xanthine oxidase inhibitors, e.g., allopurinol, and uricosuric agents, e.g., probenecid, sulfinpyrazone, and benzbromarone.

The compounds of the present invention may also be used in combination with anticancer agents such as endostatin and angiostatin or cytotoxic drugs such as adriamycin, daunomycin, cis-platinum, etoposide, taxol, taxotere and alkaloids, such as vincristine, and antimetabolites such as methotrexate.

The compounds of the present invention may also be used in combination with anti-hypertensives and other cardiovascular drugs intended to offset the consequences of atherosclerosis, including hypertension, myocardial ischemia including angina, congestive heart failure, and myocardial infarction, selected from diuretics, vasodilators such as hydralazine, β-adrenergic receptor antagonists such as propranolol, angiotensin-II converting enzyme inhibitors (ACE-inhibitors) such as enalapril used to treat geriatric mammals with mitral insufficiency, and enalapril alone and in combination with neutral endopeptidase inhibitors, angiotensin II receptor antagonists such as losartan, renin inhibitors, calcium channel blockers such as nifedipine, $α_2$-adrenergic agonists such as clonidine, α-adrenergic receptor antagonists such as prazosin, and HMG-CoA-reductase inhibitors (anti-hypercholesterolemics) such as lovastatin or atorvastatin.

The active ingredient of the present invention may also be administered in combination with one or more antibiotic, antifungal, antiprotozoal, antiviral or similar therapeutic agents.

The compounds of the present invention may also be used in combination with CNS agents such as antidepressants (such as sertraline), anti-Parkinsonian drugs (such as L-dopa, requip, miratex, MAOB inhibitors such as selegine and rasagiline, comP inhibitors such as Tasmar, A-2 inhibitors, dopamine reuptake inhibitors, NMDA antagonists, nicotine agonists, dopamine agonists and inhibitors of neuronal nitric oxide synthase), and anti-Alzheimer's drugs such as donepezil, tacrine, COX-2 inhibitors, propentofylline or metryfonate.

The compounds of the present invention may also be used in combination with osteoporosis agents such as roloxifene, droloxifene or fosomax and immunosuppressant agents such as FK-506 and rapamycin.

The present invention also relates to the formulation of the active agents of the present invention alone or with one or more other therapeutic agents which are to form the intended combination, including wherein said different drugs have varying half-lives, by creating controlled-release forms of said drugs with different release times which achieves relatively uniform dosing; or, in the case of non-human patients, a medicated feed dosage form in which said drugs used in the combination are present together in admixture in said feed composition. There is further provided in accordance with the present invention co-administration in which the combination of drugs is achieved by the simultaneous administration of said drugs to be given in combination; including co-administration by means of different dosage forms and routes of administration; the use of combinations in accordance with different but regular and continuous dosing schedules whereby desired plasma levels of said drugs involved are maintained in the mammals being treated, even though the individual mammals making up said combination are not being administered to said dog simultaneously.

This invention also relates to method for treating or preventing diseases or conditions mediated by cyclooxygenase-2 in a mammal including a human, dog, cat or livestock comprising administering an amount of a compound according to claim 1 or a pharmaceutically acceptable salt thereof effective for treating said diseases or conditions to said mammal.

This invention also relates to a pharmaceutical composition comprising an amount of a compound of formula I or a pharmaceutically acceptable salt thereof effective for treating or preventing diseases or conditions mediated by cycloxygenase-2.

More specifically, this invention relates to a pharmaceutical composition for treating a disease or condition selected from the group consisting of diseases or conditions in which prostaglandins are implicated as pathogens, pain, fever, inflammation, rheumatic fever, symptoms associated with influenza and other viral infections, common cold, low back and neck pain, dysmenorrhea, headache, toothache, sprains and strains, myositis, neuralgia, synovitis, arthritis including rheumatoid arthritis, degenerative joint disease or osteoarthritis, gout and ankylosing spondylitis, bursitis, burns, injuries following surgical and dental procedures, disease or conditions associated with cellular neoplastic transformations and metastic tumor growth, cancer, colorectal cancer, breast and skin cancer, familiar adenomatous polyposis, cyclooxygenase-mediated proliferation disorders, cyclooxygenase-mediated proliferation disorders in diabetic retinopathy and tumor angiogenesis, prostaniod-induced smooth muscle contraction mediated by synthesis of contractile prostanoids, dysmenorrhea, premature labor, asthma, eosinophil related disorders, neurodegenerative diseases, Alzheimer's and Parkinson's disease, bone loss, osteoarthritis, peptic ulcers, gastritis, regional enterotis, ulcerative colitis, diverticulitis, recurrent of gastrointestinal lesions, gastrointestinal bleeding, coagulation, anemia, hypoprothrombinemia, haemophilia, bleeding problems; kidney disease and conditions prior to surgery of taking of anticoagulants.

This invention also relates to a method of treating or preventing inflammatory processes and diseases comprising administering a compounds of formula I of this invention or its salt to a mammal including a human, wherein said inflammatory processes and diseases are defind as above, and said inhibitory compound is used in combination with one or more other therapeutically active agents under the following conditions:

A.) where a joint has become seriously inflammed as well as infected at the same time by bacteria, fungi, protozoa, and/or virus, said inhibitory compound is administered in combination with one or more antibiotic, antifungal, antiprotozoal, and/or antiviral therapeutic agents;

B.) where a multi-fold treatment of pain and inflammation is desired, said inhibitory compound is administered in combination with inhibitors of other mediators of inflammation, comprising one or more members independently selected from the group consisting essentially of:
  (1) NSAIDs;
  (2) $H_1$-receptor antagonists;
  (3) kinin-$B_1$- and $B_2$-receptor antagonists;
  (4) prostaglandin inhibitors selected from the group consisting of PGD-, PGF-$PGI_2$-, and PGE-receptor antagonists;
  (5) thromboxane $A_2$ ($TXA_2$—) inhibitors;
  (6) 5-, 12- and 15-lipoxygenase inhibitors;
  (7) leukotriene $LTC_4$-, $LTD_4/LTE_4$-, and $LTB_4$-inhibitors;
  (8) PAF-receptor antagonists;
  (9) gold in the form of an aurothio group together with one or more hydrophilic groups;
  (10) immunosuppressive agents selected from the group consisting of cyclosporine, azathioprine, and methotrexate;
  (11) anti-inflammatory glucocorticoids;
  (12) penicillamine;
  (13) hydroxychloroquine;
  (14) anti-gout agents including coichicine; xanthine oxidase inhibitors including allopurinol; and uricosuric agents selected from probenecid, sulfinpyrazone, and benzbromarone;

C.) where older mammals are being treated for disease conditions, syndromes and symptoms found in geriatric mammals, said inhibitory compound is administered in combination with one or more members independently selected from the group consisting essentially of:
  (1) cognitive therapeutics to counteract memory loss and impairment;
  (2) anti-hypertensives and other cardiovascular drugs intended to offset the consequences of atherosclerosis, hypertension, myocardial ischemia, angina, congestive heart failure, and myocardial infarction, selected from the group consisting of:
    a.) diuretics;
    b.) vasodilators;
    c.) β-adrenergic receptor antagonists;
    d.) angiotensin-II converting enzyme inhibitors (ACE-inhibitors), alone or optionally together with neutral endopeptidase inhibitors;
    e.) angiotensin II receptor antagonists;
    f.) renin inhibitors;
    g.) calcium channel blockers;
    h.) sympatholytic agents;
    i.) $\alpha_2$-adrenergic agonists;
    j.) α-adrenergic receptor antagonists; and
    k.) HMG-CoA-reductase inhibitors (anti-hypercholester-olemics);
  (3) antineoplastic agents selected from:
    a.) antimitotic drugs selected from:
      i. vinca alkaloids selected from:
        [1] vinblastine, and
        [2] vincristine;
  (4) growth hormone secretagogues;
  (5) strong analgesics;
  (6) local and systemic anesthetics; and
  (7) $H_2$-receptor antagonists, proton pump inhibitors, and other gastroprotective agents.

DETAILED DESCRIPTION OF THE INVENTION

The term "alkyl", as used herein, means a straight or branched saturated monovalent hydrocarbon radical including, but not limited to, methyl, ethyl, propyl, isopropyl, n-butyl, sec-butyl, tert-butyl and the like.

The term "alkoxy", as used herein, means an alkyl-O group wherein "alkyl" is defined as above.

The term "halo", as used herein, means fluoro, chloro, bromo or iodo, preferably F or Cl.

The term "(5 to 6-membered)-heteroaryl", as used herein, unless otherwise indicated, means a monocyclic aromatic hydrocarbon group having five to six ring atoms comprising one to four heteroatoms each independently selected from —N═, —NH—, —[N—($C_1$–$C_4$)alkyl]— —O— and —S—. Examples of the monocyclic ring systems are furyl, thienyl, pyrrolyl, pyrazolyl, imidazolyl, triazolyl, tetrazolyl, isoxazolyl, oxazolyl, thiazolyl, isothiazolyl, oxadiazolyl, oxatriazolyl, pyridyl, pyridazinyl, pyrimidinyl, pyrazinyl, triazinyl, and the like.

The term "(5- to 6-membered)-heteroaryl containing 1 to 2 ring heteroatoms independently selected from the group consisting of —N═, —NR', —S— or —O—; wherein said heteroaryl is fused to a saturated, partially saturated or aromatic "(5- to 7-membered)-carbocyclic ring," as used herein, unless otherwise indicated, means a bicyclic aromatic heterocyclic group having a first ring covalently bound to the pyrazole nucleus and containing five to six ring atoms comprising 1 to 2 heteroatoms each independently selected from —N═, —NH—, —[N—($C_1$–$C_4$)alkyl]— —O— and —S—; wherein said first ring is fused to a second ring comprising a (5 to 7 membered)-carbocycle, wherein the 5- to 7-members include the carbon atoms common to both rings. Examples of said bicyclic ring systems are benzofuranyl, isobenzofuranyl, benzothiophenyl, isobenzothiophenyl, indolyl, isoindolyl, cyclopentapyridyl, pyranopyrrolyl, indazolyl, indoxazinyl, benzoxazolyl, quinolinyl, isoquinolinyl, cinnolinyl, quinazolinyl, pyridopyridyl and the like.

The term "(5- to 6-membered)-heteroaryl containing 1 to 2 ring heteroatoms independently selected from the group consisting of —N═, —NR'—, —S—, or —O—; wherein said heteroaryl is fused to a (5- to 6-membered)-heteroaryl containing 1 to 2 ring heteroatoms independently selected from the group consisting of —N═, —NR'—, —S— or —O—" as used herein, unless otherwise indicated, means a bicyclic aromatic heterocyclic group having a first ring covalently bound to the pyrrazole nucleus and containing five to six ring atoms comprising one to two heteroatoms each independently selected from —N═, —NH—, —[N—($C_1$–$C_4$)alkyl]—, —O— and —S—; wherein said first ring is fused to a second ring comprising a 5 to 7 membered heteroaryl, wherein said second 5 to 7 members include the atoms common to both rings. Examples of said bicyclic ring systems are pyridopyridyl or the like.

The term "treating", as used herein, refers to reversing, alleviating, inhibiting the progress of, or preventing the disorder or condition to which such term applies, or one or more symptoms of such disorder or condition. The term "treatment" as used herein refers to the act of treating, as "treating" is defined immediately above.

An embodiment of the present invention includes compounds of formula I, referred to as the A(a) Group compounds, wherein A is (5- to 6-membered)-heteroaryl containing 1 to 4 ring heteroatoms independently selected from —N═, —NR'—, —O—, or —S—, wherein said heteroaryl is optionally substituted with 1 to 3 substituents independently selected from the group consisting of halo, hydroxy, cyano, mercapto, carboxy, nitro, ($C_1$–$C_4$)alkyl, ($C_2$–$C_4$)alkenyl, ($C_2$–$C_4$)alkynyl, ($C_1$–$C_4$)alkoxy, ($C_1$–$C_4$)alkyl-S—, amino, ($C_1$–$C_4$)alkylamino, di[($C_1$–$C_4$)alkyl]amino, amido, ($C_1$–$C_4$)alkylamido, di[($C_1$–$C_4$)alkyl]amido, ($C_1$–$C_4$)alkyl-(C═O)—O—, ($C_1$–$C_4$)alkyl-(C═O)—N(R')—, formyl, ($C_1$–$C_4$)alkyl-(C═O)— and ($C_1$–$C_4$)alkoxy-(C═O)—; wherein R' is hydrogen or ($C_1$–$C_4$)alkyl; wherein each of said ($C_1$–$C_4$)alkyl may optionally be substituted with 1 to 3 substituents independently selected from the group consisting of halo, hydroxy, cyano, mercapto, carboxy, nitro, ($C_1$–$C_4$)alkyl, ($C_2$–$C_4$)alkenyl, ($C_2$–$C_4$)alkynyl, ($C_1$–$C_4$)alkoxy, ($C_1$–$C_4$)alkyl-S—, amino, ($C_1$–$C_4$)alkylamino, di[($C_1$–$C_4$)alkyl]amino, amido, ($C_1$–$C_4$)alkylamido, di[($C_1$–$C_4$)alkyl]amido, ($C_1$–$C_4$)alkyl-(C═O)—O—, ($C_1$–$C_4$)alkyl-(C═O)—N(R')—, formyl, ($C_1$–$C_4$)alkyl-(C═O)— and ($C_1$–$C_4$)alkoxy-(C═O)—; wherein preferred A is selected from the group consisting of (5- to 6-membered)-heteroaryl containing 1 to 4 ring heteroatoms independently selected from —N═, —NR'—, —O—, or —S—, wherein said heteroaryl is optionally substituted with 1 to 3 substituents independently selected from the group consisting of halo, ($C_1$–$C_4$)alkyl, ($C_1$–$C_4$)alkoxy, ($C_1$–$C_4$)alkyl-S—, ($C_1$–$C_4$)alkylamino, di[($C_1$–$C_4$)alkyl]amino; wherein R' is hydrogen or ($C_1$–$C_4$)alkyl; wherein each of said ($C_1$–$C_4$)alkyl may optionally be substituted with 1 to 3 halo.

A subgenus of the embodiment of the A(a) group of compounds are those compounds (designated the subgenus A(a)-$R^1$(a)) wherein A is defined above as A(a) and $R^1$, referred to hereinafter as $R^1$(a), is (5- to 6-membered)-heteroaryl containing 1 to 4 ring heteroatoms independently selected from —N═, —NR'—, —O—, or —S—, wherein said heteroaryl is optionally substituted with 1 to 3 substituents independently selected from the group consisting of halo, hydroxy, cyano, mercapto, carboxy, nitro, ($C_1$–$C_4$)alkyl, ($C_2$–$C_4$)alkenyl, ($C_2$–$C_4$)alkynyl, ($C_1$–$C_4$)alkoxy, ($C_1$–$C_4$)alkyl-S—, amino, ($C_1$–$C_4$)alkylamino, di[($C_1$–$C_4$)alkyl]amino, amido, ($C_1$–$C_4$)alkylamido, di[($C_1$–$C_4$)alkyl]amido, ($C_1$–$C_4$)alkyl-(C═O)—O—, ($C_1$–$C_4$)alkyl-(C═O)—N(R')—, formyl, ($C_1$–$C_4$)alkyl-(C═O)— and ($C_1$–$C_4$)alkoxy-(C═O)—; wherein R' is hydrogen or ($C_1$–$C_4$)alkyl; wherein each of said ($C_1$–$C_4$)alkyl is optionally substituted with 1 to 3 substituents independently selected from the group consisting of halo, hydroxy, cyano, mercapto, carboxy, nitro, ($C_1$–$C_4$)alkyl, ($C_2$–$C_4$)alkenyl, ($C_2$–$C_4$)alkynyl, ($C_1$–$C_4$)alkoxy, ($C_1$–$C_4$)alkyl-S—, amino, ($C_1$–$C_4$)alkylamino, di[($C_1$–$C_4$)alkyl]amino, amido, ($C_1$–$C_4$)alkylamido, di[($C_1$–$C_4$)alkyl]amido, ($C_1$–$C_4$)alkyl-(C═O)—O—, ($C_1$–$C_4$)alkyl-(C═O)—N(R')—, formyl, ($C_1$–$C_4$)alkyl-(C═O)— and ($C_1$–$C_4$)alkoxy-(C═O)—; wherein preferred R' is selected from the group consisting of (5- to 6-membered)-heteroaryl containing 1 to 4 ring heteroatoms independently selected from —N═, —NR'—, —O—, or —S—, wherein said heteroaryl is optionally substituted with 1 to 3 substituents independently selected from the group consisting of halo, ($C_1$–$C_4$)alkyl, ($C_1$–$C_4$)alkoxy, ($C_1$–$C_4$)alkyl-(C═O)—, hydroxy, cyano and amino; wherein R' is hydrogen or ($C_1$–$C_4$)alkyl; wherein each of said ($C_1$–$C_4$)alkyl may optionally be substituted with 1 to 3 halo.

Another subgenus of the embodiment of the A(a) group of compounds are those compounds (designated the subgenus A(a)—R$^1$ (b)) wherein A is defined above as A(a) and R$^1$, referred to hereinafter as R$^1$ (b), is (5- to 6-membered)-heteroaryl containing 1 to 2 ring heteroatoms independently selected from the group consisting of —N=, —NR'—, —S— or —O—; wherein said heteroaryl is fused to a saturated, partially saturated or aromatic (5- to 7-membered)-carbocyclic ring; wherein either of said (5- to 6-membered)-heteroaryl ring or said fused saturated, partially saturated or aromatic (5- to 7-membered)-carbocyclic ring is optionally substituted with 1 to 2 substituents per ring, wherein said substituents are independently selected from the group consisting of halo, hydroxy, cyano, mercapto, carboxy, nitro, (C$_1$–C$_4$)alkyl, (C$_2$–C$_4$)alkenyl, (C$_2$–C$_4$)alkynyl, (C$_1$–C$_4$)alkoxy, (C$_1$–C$_4$)alkyl-S—, amino, (C$_1$–C$_4$)alkylamino, di[(C$_1$–C$_4$)alkyl]amino, amido, (C$_1$–C$_4$)alkylamido, di[(C$_1$–C$_4$)alkyl]amido, (C$_1$–C$_4$)alkyl-(C=O)—O—, (C$_1$–C$_4$)alkyl-(C=O)—N(R')—, formyl, (C$_1$–C$_4$)alkyl-(C=O)— and (C$_1$–C$_4$)alkoxy-(C=O)—; wherein R' is hydrogen or (C$_1$–C$_4$)alkyl; wherein each of said (C$_1$–C$_4$)alkyl is optionally substituted with 1 to 3 substituents independently selected from the group consisting of halo, hydroxy, cyano, mercapto, carboxy, nitro, (C$_1$–C$_4$)alkyl, (C$_2$–C$_4$)alkenyl, (C$_2$–C$_4$)alkynyl, (C$_1$–C$_4$)alkoxy, (C$_1$–C$_4$)alkyl-S—, amino, (C$_1$–C$_4$)alkylamino, di[(C$_1$–C$_4$)alkyl]amino, amido, (C$_1$–C$_4$)alkylamido, di[(C$_1$–C$_4$)alkyl]amido, (C$_1$–C$_4$)alkyl-(C=O)—O—, (C$_1$–C$_4$)alkyl-(C=O)—N(R')—, formyl, (C$_1$–C$_4$)alkyl-(C=O)— and (C$_1$–C$_4$)alkoxy-(C=O)—; wherein preferred R' is selected from the group consisting of (5- to 6-membered)-heteroaryl containing 1 ring heteroatom selected from the group consisting of —N=, —NR'—, —S— or —O—; wherein said heteroaryl is fused to an aromatic (6-membered)-carbocyclic ring; wherein either of said (5- to 6-membered)-heteroaryl ring or said fused aromatic (6-membered)-carbocyclic ring may optionally be substituted with 1 to 2 substituents per ring, wherein said substituents are independently selected from the group consisting of halo and (C$_1$–C$_4$)alkyl; wherein R' is hydrogen or (C$_1$–C$_4$)alkyl.

Another subgenus of the embodiment of the A(a) group of compounds are those compounds (designated the subgenus A(a)—R$^1$ (c)) wherein A is as defined above as A(a) and R$^1$, referred to hereinafter as R$^1$ (c), is (5- to 6-membered)-heteroaryl containing 1 to 2 ring heteroatoms independently selected from the group consisting of —N=, —NR'—, —S—, or —O—; wherein said heteroaryl is fused to a (5- to 6-membered)-heteroaryl containing 1 to 2 ring heteroatoms independently selected from the group consisting of —N=, —NR'—, —S— or —O—; wherein either of said (5- to 6-membered)-heteroaryl or said fused (5- to 6-membered)-heteroaryl is optionally substituted with one to two substituents per ring, wherein said substituents are independently selected from the group consisting of halo, hydroxy, cyano, mercapto, carboxy, nitro, (C$_1$–C$_4$)alkyl, (C$_2$–C$_4$)alkenyl, (C$_2$–C$_4$)alkynyl, (C$_1$–C$_4$)alkoxy, (C$_1$–C$_4$)alkyl-S—, amino, (C$_1$–C$_4$)alkylamino, di[(C$_1$–C$_4$)alkyl]amino, amido, (C$_1$–C$_4$)alkylamido, di[(C$_1$–C$_4$)alkyl]amido, (C$_1$–C$_4$)alkyl-(C=O)—O—, (C$_1$–C$_4$)alkyl-(C=O)—N(R')—, formyl, (C$_1$–C$_4$)alkyl-(C=O)— and (C$_1$–C$_4$)alkoxy-(C=O)—; wherein R' is hydrogen or (C$_1$–C$_4$)alkyl; wherein each of said (C$_1$–C$_4$)alkyl is optionally substituted with 1 to 3 substituents independently selected from the group consisting of halo, hydroxy, cyano, mercapto, carboxy, nitro, (C$_1$–C$_4$)alkyl, (C$_2$–C$_4$)alkenyl, (C$_2$–C$_4$)alkynyl, (C$_1$–C$_4$)alkoxy, (C$_1$–C$_4$)alkyl-S—, amino, (C$_1$–C$_4$)alkylamino, di[(C$_1$–C$_4$)alkyl]amino, amido, (C$_1$–C$_4$)alkylamido, di[(C$_1$–C$_4$)alkyl]amido, (C$_1$–C$_4$)alkyl-(C=O)—O—, (C$_1$–C$_4$)alkyl-(C=O)—N(R')—, formyl, (C$_1$–C$_4$)alkyl-(C=O)— and (C$_1$–C$_4$)alkoxy-(C=O)—.

Another embodiment of the invention of the A(a) group of compounds, including the subgenera A(a)—R$^1$ (a), A(a)—R$^1$ (b) and A(a)—R$^1$ (c), are those compounds wherein A is as defined above as A(a), R$^1$ is as defined above as R$^1$ (a, b or c) and one of R$^3$ or R$^4$ is hydrogen (wherein R$^{3,4a}$ refers to R$^3$ as hydrogen and wherein R$^{3,4b}$ refers to R$^4$ as hydrogen). Such subgenera can be designated A(a)—R$^{3,4a}$ and A(a)—R$^{3,4a}$, and sub-subgenera A(a)—R$^1$(a)—R$^{3,4a}$, A(a)—R$^1$(a)—R$^{3,4b}$, A(a)—R$^1$(b)—R$^{3,4a}$, A(a)—R$^1$(b)—R$^{3,4b}$, A(a)—R$^1$(c)—R$^{3,4a}$ and A(a)—R$^1$(c)—R$^{3,4b}$).

Another embodiment of the invention of compounds of the formula A(a) compounds, including the subgenera A(a)—R$^1$(a), A(a)—R$^1$ (b), A(a)—R$^1$ (c), A(a)—R$^{3,4a}$ and A(a)—R$^{3,4b}$ and sub-subgenera A(a)—R$^1$(a)—R$^{3,4a}$, A(a)—R$^1$(a)—R$^{3,4b}$, A(a)—R$^1$(b)—R$^{3,4a}$, A(a)—R$^1$(b)—R$^{3,4b}$, A(a)—R$^1$(c)—R$^{3,4a}$ and A(a)—R$^1$(c)—R$^{3,4b}$, are those compounds wherein two, three or four of X$^1$, X$^2$, X$^3$ and X$^4$ are hydrogen (wherein X$^{1-4a}$ refers to two of X$^1$–X$^4$ as hydrogen, X$^{1-4b}$ refers to three of X$^1$–X$^4$ as hydrogen and X$^{1-4c}$ refers to four of X$^1$–X$^4$ as hydrogen). Such subgenera can be designated A(a)—X$^{1-4a}$, A(a)—X$^{1-4b}$, A(a)—X$^{1-4c}$. Such sub-subgenera can be designated A(a)—R$^1$(a)—X$^{1-4a}$, A(a)—R$^1$(b)—X$^{1-4a}$, A(a)—R$^1$(c)—X$^{1-4a}$, A(a)—R$^{3,4a}$—X$^{1-4a}$ and A(a)—R$^{3,4b}$—X$^{1-4a}$, A(a)—R$^1$(a)—X$^{1-4b}$, A(a)—R$^1$(b)—X$^{1-4b}$, A(a)—R$^1$(c)—X$^{1-4b}$, A(a)—R$^{3,4a}$—X$^{1-4b}$ and A(a)—R$^{3,4b}$—X$^{1-4b}$, A(a)—R$^1$(a)—X$^{1-4c}$, A(a)—R$^1$(b)—X$^{1-4c}$, A(a)—R$^1$(c)—X$^{1-4c}$, A(a)—R$^{3,4a}$—X$^{1-4c}$ and A(a)—R$^{3,4b}$—X$^{1-4c}$. Sub-sub-subgenera can be designated A(a)—R$^1$(a)—R$^{3,4a}$—X$^{1-4a}$, A(a)—R$^1$(a)—R$^{3,4b}$—X$^{1-4a}$, A(a)—R$^1$(b)—R$^{3,4a}$—X$^{1-4a}$, A(a)—R$^1$(b)—R$^{3,4b}$—X$^{1-4a}$, A(a)—R$^1$(c)—R$^{3,4a}$—X$^{1-4a}$ and A(a)—R$^1$(c)—R$^{3,4b}$—X$^{1-4a}$, A(a)—R$^1$(a)—R$^{3,4a}$—X$^{1-4b}$, A(a)—R$^1$(a)—R$^{3,4b}$—X$^{1-4b}$, A(a)—R$^1$(b)—R$^{3,4a}$—X$^{1-4b}$, A(a)—R$^1$(b)—R$^{3,4b}$—X$^{1-4b}$, A(a)—R$^1$(c)—R$^{3,4a}$—X$^{1-4b}$ and A(a)—R$^1$(c)—R$^{3,4b}$—X$^{1-4b}$, A(a)—R$^1$(a)—R$^{3,4a}$—X$^{1-4c}$, A(a)—R$^1$(a)—R$^{3,4b}$—X$^{1-4c}$, A(a)—R$^1$(b)—R$^{3,4a}$—X$^{1-4c}$, A(a)—R$^1$(b)—R$^{3,4b}$—X$^{1-4c}$, A(a)—R$^1$(c)—R$^{3,4a}$—X$^{1-4c}$ and A(a)—R$^1$(c)—R$^{3,4b}$—X$^{1-4c}$.

A group of compounds which is preferred among the A(a) Group compounds, including subgenera A(a)—R$^1$(a), A(a)—R$^1$(b), A(a)—R$^1$(c), are those compounds designated subgenera A(a)—R$^{3a}$, and sub-subgenera A(a)—R$^1$(a)—R$^{3a}$, A(a)—R$^1$(b)—R$^{3a}$, A(a)—R$^1$(c)—R$^{3a}$ including any preferences) wherein A is as defined above as A(a), R$^1$ is as defined above as R$^1$(a, b or c) and R$^3$ is selected from hydrogen; halo; (C$_1$–C$_4$)alkyl optionally substituted with 1 to 3 halo; (C$_1$–C$_4$)alkoxy; (C$_1$–C$_4$)alkyl-O—C(=O)— and cyano (wherein said preferred R$^3$ is referred to as R$^{3a}$).

Another group of compounds which is preferred among the A(a) Group of compounds, including subgenera A(a)—R$^1$(a), A(a)—R$^1$(b), A(a)—R$^1$(c), A(a)—R$^{3a}$, sub-subgenera A(a)—R$^1$(a)—R$^{3a}$, A(a)—R$^1$(b)—R$^{3a}$, A(a)—R$^1$(c)—R$^{3a}$, are those compounds (designated subgenera A(a)—R$^{4a}$, and sub-subgenera A(a)—R$^1$(a)—R$^{4a}$, A(a)—R$^1$(b)—R$^{4a}$, A(a)—R$^1$(c)—R$^{4a}$, A(a)—R$^1$(a)—R$^{3a}$—R$^{4a}$, A(a)—R$^1$(b)—R$^{3a}$—R$^{4a}$, A(a)—R$^1$(c)—R$^{3a}$—R$^{4a}$), wherein A is as defined above as A(a), R$^1$ is as defined above as R$^1$(a, b or c), R$^3$ is defined above as R$^{3a}$ and R$^4$ is selected from hydrogen; halo; (C$_1$–C$_4$)alkyl optionally substituted with 1 to 3 halo; (C$_1$–C$_4$)alkoxy; (C$_1$–C$_4$)alkyl-O—C(=O)— and cyano (wherein said preferred R$^4$ is R$^{4a}$).

Another group of compounds which is preferred among each A(a) Group of compounds, including subgenera A(a)—R$^1$(a), A(a)—R$^1$(b), A(a)—R$^1$(c), A(a)—R$^{3a}$, A(a)—R$^{4a}$, sub-subgenera A(a)—R$^1$(a)—R$^{3a}$, A(a)—R$^1$(b)—R$^{3a}$, A(a)—R$^1$(c)—R$^{3a}$, A(a)—R$^1$(a)—R$^{4a}$, A(a)—R$^1$(b)—R$^{4a}$, A(a)—R$^1$(c)—R$^4$, and A(a)—R$^{3a}$—R$^{4a}$, and sub-sub-subgenera A(a)—R$^1$(a)—R$^{3a}$—R$^{4a}$, A(a)—R$^1$(b)—R$^{3a}$—R$^{4a}$, A(a)—R$^1$(c)—R$^{3a}$—R$^{4a}$) are those compounds (designated subgenera A(a)—X$^{1-4d}$ and sub-subgenera A(a)—R$^1$(a)—X$^{1-4d}$, A(a)—R$^1$(b)—X$^{1-4d}$, A(a)—R$^1$(c)—X$^{1-4d}$, A(a)—R$^{3a}$—X$^{1-4d}$ and A(a)—R$^{4a}$—X$^{1-4d}$ and sub-sub-subgenera A(a)—R$^1$(a)—R$^{3a}$—X$^{1-4d}$, A(a)—R$^1$(b)—R$^{3a}$—X$^{1-4d}$, A(a)—R$^1$(c)—R$^{3a}$—X$^{1-4d}$, A(a)—R$^1$(a)—R$^{4a}$—X$^{1-4d}$, A(a)—R$^1$(b)—R$^{4a}$—X$^{1-4d}$, A(a)—R$^1$(c)—R$^{4a}$—X$^{1-4d}$, A(a)—R$^{3a}$—R$^{4a}$—X$^{1-4d}$, and sub-sub-sub-subgenera A(a)—R$^1$(a)—R$^{3a}$—R$^{4a}$—X$^{1-4d}$, A(a)—R$^1$(b)—R$^{3a}$—R$^{4a}$—X$^{1-4d}$, A(a)—R$^1$(c)—R$^{3a}$—R$^{4a}$—X$^{1-4d}$) wherein X$^1$ and X$^2$ are each independently selected from hydrogen; halo; (C$_1$–C$_4$)alkyl optionally substituted with 1 to 3 halo; cyano and (C$_1$–C$_4$)alkoxy (wherein X$^{1-4d}$ refers to said preferred X$^1$ and X$^2$).

A group of compounds which is preferred among each A(a) Group of compounds, including subgenera A(a)—R$^1$(a), A(a)—R$^1$(b), A(a)—R$^1$(c), A(a)—R$^{3a}$, A(a)—R$^{4a}$, sub-subgenera A(a)—R$^1$(a)—R$^{3a}$, A(a)—R$^1$(b)—R$^{3a}$, A(a)—R$^1$(c)—R$^{3a}$, A(a)—R$^1$(a)—R$^{4a}$, A(a)—R$^1$(b)—R$^{4a}$, A(a)—R$^1$(c)—R$^{4a}$, A(a)—R$^{3a}$—R$^{4a}$, and sub-sub-subgenera A(a)—R$^1$(a)—R$^{3a}$—R$^{4a}$, A(a)—R$^1$(b)—R$^{3a}$—R$^{4a}$, A(a)—R$^1$(c)—R$^{3a}$—R$^{4a}$) are those compounds (designated subgenera A(a)—X$^{1-4e}$ and sub-subgenera A(a)—R$^1$(a)—X$^{1-4e}$, A(a)—R$^1$(b)—X$^{1-4e}$, A(a)—R$^1$(c)—X$^{1-4e}$, A(a)—R$^{3a}$—X$^{1-4e}$ and A(a)—R$^{4a}$—X$^{1-4e}$ and sub-sub-subgenera A(a)—R$^1$(a)—R$^{3a}$—X$^{1-4e}$, A(a)—R$^1$(b)—R$^{3a}$—X$^{1-4e}$, A(a)—R$^1$(c)—R$^{3a}$—X$^{1-4e}$, A(a)—R$^1$(a)—R$^{4a}$—X$^{1-4e}$, A(a)—R$^1$(b)—R$^{4a}$—X$^{1-4e}$, A(a)—R$^1$(c)—R$^{4a}$—X$^{1-4e}$, A(a)—R$^{3a}$—R$^{4a}$—X$^{1-4e}$, and sub-sub-sub-subgenera A(a)—R$^1$(a)—R$^{3a}$—R$^{4a}$—X$^{1-4e}$, A(a)—R$^1$(b)—R$^{3a}$—R$^{4a}$—X$^{1-4e}$, A(a)—R$^1$(c)—R$^{3a}$—R$^{4a}$—X$^{1-4e}$) wherein X$^3$ and X$^4$ are each independently selected from hydrogen; halo; (C$_1$–C$_4$)alkyl optionally substituted with 1 to 3 halo; cyano and (C$_1$–C$_4$)alkoxy (wherein X$^{1-4e}$ refers to said preferred X$^3$ and X$^4$).

An embodiment of the present invention includes compounds of formula I, referred to as the A(b) Group compounds, wherein A is (5- to 6-membered)-heteroaryl containing 1 to 2 ring heteroatoms independently selected from the group consisting of —N=, —NR'—, —S— or —O—; wherein said heteroaryl is fused to a saturated, partially saturated or aromatic (5- to 7-membered)-carbocyclic ring; wherein either of said (5- to 6-membered)-heteroaryl ring or said fused saturated, partially saturated or aromatic (5- to 7-membered)-carbocyclic ring may optionally be substituted with 1 to 2 substituents per ring, wherein said substituents are independently selected from the group consisting of halo, hydroxy, cyano, mercapto, carboxy, nitro, (C$_1$–C$_4$)alkyl, (C$_2$–C$_4$)alkenyl, (C$_2$–C$_4$)alkynyl, (C$_1$–C$_4$)alkoxy, (C$_1$–C$_4$)alkyl-S—, amino, (C$_1$–C$_4$)alkylamino, di[(C$_1$–C$_4$)alkyl]amino, amido, (C$_1$–C$_4$)alkylamido, di[(C$_1$–C$_4$)alkyl]amido, (C$_1$–C$_4$)alkyl-(C=O)—O—, (C$_1$–C$_4$)alkyl-(C=O)—N(R')—, formyl, (C$_1$–C$_4$)alkyl-(C=O)— and (C$_1$–C$_4$)alkoxy-(C=O)—; wherein R' is hydrogen or (C$_1$–C$_4$)alkyl; wherein each of said (C$_1$–C$_4$)alkyl is optionally substituted with 1 to 3 substituents independently selected from the group consisting of halo, hydroxy, cyano, mercapto, carboxy, nitro, (C$_1$–C$_4$)alkyl, (C$_2$–C$_4$)alkenyl, (C$_2$–C$_4$)alkynyl, (C$_1$–C$_4$)alkoxy, (C$_1$–C$_4$)alkyl-S—, amino, (C$_1$–C$_4$)alkylamino, di[(C$_1$–C$_4$)alkyl]amino, amido, (C$_1$–C$_4$)alkylamido, di[(C$_1$–C$_4$)alkyl]amido, (C$_1$–C$_4$)alkyl-(C=O)—O—, (C$_1$–C$_4$)alkyl-(C=O)—N(R')—, formyl, (C$_1$–C$_4$)alkyl-(C=O)— and (C$_1$–C$_4$)alkoxy-(C=O)—.

A subgenus of the embodiment of the A(b) group of compounds are those compounds (designated the subgenus A(b)—R$^1$(a)) wherein A is defined above as A(b) and R$^1$, referred to hereinafter as R$^1$(a), is (5- to 6-membered)-heteroaryl containing 1 to 4 ring heteroatoms independently selected from —N=, —NR'—, —O—, or —S—, wherein said heteroaryl is optionally substituted with 1 to 3 substituents independently selected from the group consisting of halo, hydroxy, cyano, mercapto, carboxy, nitro, (C$_1$–C$_4$)alkyl, (C$_2$–C$_4$)alkenyl, (C$_2$–C$_4$)alkynyl, (C$_1$–C$_4$)alkoxy, (C$_1$–C$_4$)alkyl-S—, amino, (C$_1$–C$_4$)alkylamino, di[(C$_1$–C$_4$)alkyl]amino, amido, (C$_1$–C$_4$)alkylamido, di[(C$_1$–C$_4$)alkyl]amido, (C$_1$–C$_4$)alkyl-(C=O)—O—, (C$_1$–C$_4$)alkyl-(C=O)—N(R')—, formyl, (C$_1$–C$_4$)alkyl-(C=O)— and (C$_1$–C$_4$)alkoxy-(C=O)—; wherein R' is hydrogen or (C$_1$–C$_4$)alkyl; wherein each of said (C$_1$–C$_4$)alkyl is optionally substituted with 1 to 3 substituents independently selected from the group consisting of halo, hydroxy, cyano, mercapto, carboxy, nitro, (C$_1$–C$_4$)alkyl, (C$_2$–C$_4$)alkenyl, (C$_2$–C$_4$)alkynyl, (C$_1$–C$_4$)alkoxy, (C$_1$–C$_4$)alkyl-S—, amino, (C$_1$–C$_4$)alkylamino, di[(C$_1$–C$_4$)alkyl]amino, amido, (C$_1$–C$_4$)alkylamido, di[(C$_1$–C$_4$)alkyl]amido, (C$_1$–C$_4$)alkyl-(C=O)—O—, (C$_1$–C$_4$)alkyl-(C=O)—N(R')—, formyl, (C$_1$–C$_4$)alkyl-(C=O)— and (C$_1$–C$_4$)alkoxy-(C=O)—; wherein preferred R' is selected from the group consisting of (5- to 6-membered)-heteroaryl containing 1 to 4 ring heteroatoms independently selected from —N=, —NR'—, —O—, or —S—, wherein said heteroaryl is optionally substituted with 1 to 3 substituents independently selected from the group consisting of halo, (C$_1$–C$_4$)alkyl, (C$_1$–C$_4$)alkoxy, (C$_1$–C$_4$)alkyl-(C=O)—, hydroxy, cyano and amino; wherein R' is hydrogen or (C$_1$–C$_4$)alkyl; wherein each of said (C$_1$–C$_4$)alkyl may optionally be substituted with 1 to 3 halo.

Another subgenus of the embodiment of the A(b) group of compounds are those compounds (designated the subgenus A(b)—R$^1$(b)) wherein A is defined above as A(b) and R$^1$, referred to hereinafter as R$^1$(b), is (5- to 6-membered)-heteroaryl containing 1 to 2 ring heteroatoms independently selected from the group consisting of —N=, —NR'—, —S— or —O—; wherein said heteroaryl is fused to a saturated, partially saturated or aromatic (5- to 7-membered)-carbocyclic ring; wherein either of said (5- to 6-membered)-heteroaryl ring or said fused saturated, partially saturated or aromatic (5- to 7-membered)-carbocyclic ring is optionally substituted with 1 to 2 substituents per ring, wherein said substituents are independently selected from the group consisting of halo, hydroxy, cyano, mercapto, carboxy, nitro, (C$_1$–C$_4$)alkyl, (C$_2$–C$_4$)alkenyl, (C$_2$–C$_4$)alkynyl, (C$_1$–C$_4$)alkoxy, (C$_1$–C$_4$)alkyl-S—, amino, (C$_1$–C$_4$)alkylamino, di[(C$_1$–C$_4$)alkyl]amino, amido, (C$_1$–C$_4$)alkylamido, di[(C$_1$–C$_4$)alkyl]amido, (C$_1$–C$_4$)alkyl-(C=O)—O—, (C$_1$–C$_4$)alkyl-(C=O)—N(R')—, formyl, (C$_1$–C$_4$)alkyl-(C=O)— and (C$_1$–C$_4$)alkoxy-(C=O)—; wherein R' is hydrogen or (C$_1$–C$_4$)alkyl; wherein each of said (C$_1$–C$_4$)alkyl is optionally substituted with 1 to 3 substituents independently selected from the group consisting of halo, hydroxy, cyano, mercapto, carboxy, nitro, (C$_1$–C$_4$)alkyl, (C$_2$–C$_4$)alkenyl, (C$_2$–C$_4$)alkynyl, (C$_1$–C$_4$)alkoxy, (C$_1$–C$_4$)alkyl-S—, amino, (C$_1$–C$_4$)alkylamino, di[(C$_1$–C$_4$)alkyl]amino, amido, (C$_1$–C$_4$)alkylamido, di[(C$_1$–C$_4$)alkyl]amido, (C$_1$–C$_4$)alkyl-(C=O)—O—, (C$_1$–C$_4$)alkyl-(C=O)—N(R')—, formnyl, (C$_1$–C$_4$)alkyl-(C=O)— and (C$_1$–C$_4$)alkoxy-(C=O)—; wherein preferred R' is selected from the group consisting of (5- to 6-membered)-heteroaryl containing 1 ring heteroatom selected from the group consisting of —N=, —NR'—, —S— or —O—; wherein said heteroaryl is fused to an aromatic (6-membered)-carbocyclic ring; wherein either of said (5- to 6-membered)-heteroaryl ring or said fused aromatic (6-membered)-carbocyclic ring may optionally be substituted with 1 to 2 substituents per ring, wherein said substituents are independently selected from the group consisting of halo and ($C_1$–$C_4$)alkyl; wherein R' is hydrogen or ($C_1$–$C_4$)alkyl.

Another subgenus of the embodiment of the A(b) group of compounds are those compounds (designated the subgenus A(b)—$R^1$ (c)) wherein A is as defined above as A(b) and $R^1$, referred to hereinafter as $R^1$ (c), is (5- to 6-membered)-heteroaryl containing 1 to 2 ring heteroatoms independently selected from the group consisting of —N═, —NR'—, —S—, or —O—; wherein said heteroaryl is fused to a (5- to 6-membered)-heteroaryl containing 1 to 2 ring heteroatoms independently selected from the group consisting of —N═, —NR'—, —S— or —O—; wherein either of said (5- to 6-membered)-heteroaryl or said fused (5- to 6-membered)-heteroaryl is optionally substituted with one to two substituents per ring, wherein said substituents are independently selected from the group consisting of halo, hydroxy, cyano, mercapto, carboxy, nitro, ($C_1$–$C_4$)alkyl, ($C_2$–$C_4$)alkenyl, ($C_2$–$C_4$)alkynyl, ($C_1$–$C_4$)alkoxy, ($C_1$–$C_4$)alkyl-S—, amino, ($C_1$–$C_4$)alkylamino, di[($C_1$–$C_4$)alkyl]amino, amido, ($C_1$–$C_4$)alkylamido, di[($C_1$–$C_4$)alkyl]amido, ($C_1$–$C_4$)alkyl-(C═O)—O—, ($C_1$–$C_4$)alkyl-(C═O)—N(R')—, formyl, ($C_1$–$C_4$)alkyl-(C═O)— and ($C_1$–$C_4$)alkoxy-(C═O)—; wherein R' is hydrogen or ($C_1$–$C_4$)alkyl; wherein each of said ($C_1$–$C_4$)alkyl is optionally substituted with 1 to 3 substituents independently selected from the group consisting of halo, hydroxy, cyano, mercapto, carboxy, nitro, ($C_1$–$C_4$)alkyl, ($C_2$–$C_4$)alkenyl, ($C_2$–$C_4$)alkynyl, ($C_1$–$C_4$)alkoxy, ($C_1$–$C_4$)alkyl-S—, amino, ($C_1$–$C_4$)alkylamino, di[($C_1$–$C_4$)alkyl]amino, amido, ($C_1$–$C_4$)alkylamido, di[($C_1$–$C_4$)alkyl]amido, ($C_1$–$C_4$)alkyl-(C═O)—O—, ($C_1$–$C_4$)alkyl-(C═O)—N(R'), formyl, ($C_1$–$C_4$)alkyl-(C═O)— and ($C_1$–$C_4$)alkoxy-(C═O)—.

Another embodiment of the invention of the A(b) group of compounds, including the subgenera A(b)—$R^1$(a), A(b)—$R^1$(b) and A(b)—$R^1$(c), are those compounds wherein A is as defined above as A(b), $R^1$is as defined above as $R^1$(a, b or c) and one of $R^3$ or $R^4$ is hydrogen (wherein $R^{3,4a}$, refers to $R^3$ as hydrogen and wherein $R^{3,4b}$ refers to $R^4$ as hydrogen). Such subgenera can be designated A(b)—$R^{3,4a}$ and A(b)—$R^{3,4b}$, and sub-subgenera A(b)—$R^1$(a)—$R^{3,4a}$, A(b)—$R^1$(a)—$R^{3,4b}$, A(b)—$R^1$(b)—$R^{3,4a}$, A(b)—$R^1$(b)—$R^{3,4b}$, A(b)—$R^1$(c)—$R^{3,4a}$ and A(b)—$R^1$(c)—$R^{3,4b}$).

Another embodiment of the invention of compounds of the formula A(b) compounds, including the subgenera A(b)—$R^1$(a), A(b)—$R^1$(b), A(b)—$R^1$(c), A(b)—$R^{3,4a}$ and A(b)—$R^{3,4b}$ and sub-subgenera A(b)—$R^1$(a)—$R^{3,4a}$, A(b)—$R^1$(a)—$R^{3,4b}$, A(b)—$R^1$(b)—$R^{3,4a}$, A(b)—$R^1$(b)—$R^{3,4b}$, A(b)—$R^1$(c)—$R^{3,4a}$ and A(b)—$R^1$(c)—$R^{3,4b}$, are those compounds wherein two, three or four of $X^1$, $X^2$, $X^3$ and $X^4$ are hydrogen (wherein $X^{1-4a}$ refers to two of $X^1$–$X^4$ as hydrogen, $X^{1-4b}$ refers to three of $X^1$–$X^4$ as hydrogen and $X^{1-4c}$ refers to four of $X^1$–$X^4$ as hydrogen). Such subgenera can be designated A(b)—$X^{1-4a}$, A(b)—$X^{1-4b}$, A(b)—$X^{1-4c}$. Such sub-subgenera can be designated A(b)—$R^1$(a)—$X^{1-4a}$, A(b)—$R^1$(b)—$X^{1-4a}$, A(b)—$R^1$(c)—$X^{1-4a}$, A(b)—$R^{3,4a}$—$X^{1-4a}$ and A(b)—$R^{3,4b}$—$X^{1-4a}$, A(b)—$R^1$(a)—$X^{1-4b}$, A(b)—$R^1$(b)—$X^{1-4b}$, A(b)—$R^1$(c)—$X^{1-4b}$, A(b)—$R^{3,4a}$—$X^{1-4b}$ and A(b)—$R^{3,4b}$—$X^{1-4b}$, A(b)—$R^1$(a)—$X^{1-4c}$, A(b)—$R^1$(b)—$X^{1-4c}$, A(b)—$R^1$(c)—$X^{1-4c}$, A(b)—$R^{3,4a}$—$X^{1-4c}$ and A(b)—$R^{3,4b}$—$X^{1-4c}$. Sub-sub-subgenera can be designated A(b)—$R^1$(a)—$R^{3,4a}$—$X^{1-4a}$, A(b)—$R^1$(a)—$R^{3,4b}$—$X^{1-4a}$, A(b)—$R^1$(b)—$R^{3,4a}$—$X^{1-4a}$, A(b)—$R^1$(b)—$R^{3,4b}$—$X^{1-4a}$, A(b)—$R^1$(c)—$R^{3,4a}$—$X^{1-4a}$ and A(b)—$R^1$(c)—$R^{3,4b}$—$X^{1-4a}$, A(b)—$R^1$(a)—$R^{3,4a}$—$X^{1-4b}$, A(b)—$R^1$(a)—$R^{3,4b}$—$X^{1-4b}$, A(b)—$R^1$(b)—$R^{3,4a}$—$X^{1-4b}$, A(b)—$R^1$(b)—$R^{3,4b}$—$X^{1-4b}$, A(b)—$R^1$(c)—$R^{3,4a}$—$X^{1-4b}$ and A(b)—$R^1$(c)—$R^{3,4b}$—$X^{1-4b}$, A(b)—$R^1$(a)—$R^{3,4a}$—$X^{1-4c}$, A(b)—$R^1$(a)—$R^{3,4b}$—$X^{1-4c}$, A(b)—$R^1$(b)—$R^{3,4a}$—$X^{1-4c}$, A(b)—$R^1$(b)—$R^{3,4b}$—$X^{1-4c}$, A(b)—$R^1$(c)—$R^{3,4a}$—$X^{1-4c}$ and A(b)—$R^1$(c)—$R^{3,4b}$—$X^{1-4c}$.

A group of compounds which is preferred among the A(b) Group compounds, including subgenera A(b)—$R^1$ (a), A(b)—$R^1$(b), A(b)—$R^1$(c), are those compounds (designated subgenera A(b)—$R^{3a}$, and sub-subgenera A(b)—$R^1$(a)—$R^{3a}$, A(b)—$R^1$(b)—$R^{3a}$, A(b)—$R^1$(c)—$R^{3a}$ including any preferences) wherein A is as defined above as A(b), $R^1$ is as defined above as $R^1$ (a, b or c) and $R^3$ is selected from hydrogen; halo; ($C_1$–$C_4$)alkyl optionally substituted with 1 to 3 halo; ($C_1$–$C_4$)alkoxy; ($C_1$–$C_4$)alkyl-O—C(═O)— and cyano (wherein said preferred $R^3$ is referred to as $R^{3a}$).

Another group of compounds which is preferred among the A(b) Group of compounds, including subgenera A(b)—$R^1$(a), A(b)—$R^1$(b), A(b)—$R^1$(c), A(b)—$R^{3a}$, sub-subgenera A(b)—$R^1$(a)—$R^{3a}$, A(b)—$R^1$(b)—$R^{3a}$, A(b)—$R^1$(c)—$R^{3a}$, are those compounds (designated subgenera A(b)—$R^{4a}$, and sub-subgenera A(b)—$R^1$(a)—$R^{4a}$, A(b)—$R^1$(b)—$R^{4a}$, A(b)—$R^1$(c)—$R^{4a}$, A(b)—$R^1$(a)—$R^{3a}$—$R^{4a}$, A(b)—$R^1$(b)—$R^{3a}$—$R^{4a}$, A(b)—$R^1$(c)—$R^3$—$R^{4a}$), wherein A is as defined above as A(b), $R^1$ is as defined above as $R^1$(a, b or c), $R^3$ is defined above as $R^{3a}$ and $R^4$ is selected from hydrogen; halo; ($C_1$–$C_4$)alkyl optionally substituted with 1 to 3 halo; ($C_1$–$C_4$)alkoxy; ($C_1$–$C_4$)alkyl-O—C(═O)— and cyano (wherein said preferred $R^4$ is $R^{4a}$).

Another group of compounds which is preferred among each A(b) Group of compounds, including subgenera A(b)—$R^1$(a), A(b)—$R^1$(b), A(b)—$R^1$(c), A(b)—$R^{3a}$, A(b)—$R^{4a}$, sub-subgenera A(b)—$R^1$(a)—$R^{3a}$, A(b)—$R^1$(b)—$R^{3a}$, A(b)—$R^1$(c)—$R^{3a}$, A(b)—$R^1$(a)—$R^{4a}$, A(b)—$R^1$(b)—$R^{4a}$, A(b)—$R^1$(c)—$R^{4a}$, and A(b)—$R^{3a}$—$R^{4a}$, and sub-sub-subgenera A(b)—$R^1$(a)—$R^{3a}$—$R^4$, A(b)—$R^1$(b)—$R^{3a}$—$R^{4a}$, A(b)—$R^1$(c)—$R^{3a}$—$R^{4a}$) are those compounds (designated subgenera A(b)—$X^{1-4d}$ and sub-subgenera A(b)—$R^1$(a)—$X^{1-4d}$, A(b)—$R^1$(b)—$X^{1-4d}$, A(b)—$R^1$(c)—$X^{1-4d}$, A(b)—$R^{3a}$—$X^{1-4d}$ and A(b)—$R^{4a}$—$X^{1-4d}$ and sub-sub-subgenera A(b)—$R^1$(a)—$R^{3a}$—$X^{1-4d}$, A(b)—$R^1$(b)—$R^{3a}$—$X^{1-4d}$, A(b)—$R^1$(c)—$R^{3a}$—$X^{1-4d}$, A(b)—$R^1$(a)—$R^{4a}$—$X^{1-4d}$, A(b)—$R^1$(b)—$R^{4a}$—$X^{1-4d}$, A(b)—$R^1$(c)—$R^{4a}$—$X^{1-4d}$, A(b)—$R^3$—$R^{4a}$—$X^{1-4d}$, and sub-sub-sub-subgenera A(b)—$R^1$(a)—$R^{3a}$—$R^{4a}$—$X^{1-4d}$, A(b)—$R(b)$—$R^{3a}$—$R^{4a}$—$X^{1-4d}$, A(b)—$R^1$(c)—$R^{3a}$—$R^{4a}$—$X^{1-4d}$) wherein $X^1$ and $X^2$ are each independently selected from hydrogen; halo; ($C_1$–$C_4$)alkyl optionally substituted with 1 to 3 halo; cyano and ($C_1$–$C_4$)alkoxy (wherein $X^{1-4d}$ refers to said preferred $X^1$ and $X^2$).

A group of compounds which is preferred among each A(b) Group of compounds, including subgenera A(b)—$R^1$ (a), A(b)—$R^1$(b), A(b)—$R^1$(c), A(b)—$R^{3a}$, A(b)—$R^{4a}$, sub-subgenera A(b)—$R^1$(a)—$R^{3a}$, A(b)—$R^1$(b)—$R^{3a}$, A(b)—$R^1$(c)—$R^{3a}$, A(b)—$R^1$(a)—$R^{4a}$, A(b)—$R^1$(b)—$R^{4a}$, A(b)—$R^1$(c)—$R^{4a}$, A(b)—$R^{3a}$—$R^{4a}$, and sub-sub-subgenera A(b)—$R^1$(a)—$R^{3a}$—$R^{4a}$, A(b)—$R^1$(b)—$R^{3a}$—$R^{4a}$, A(b)—$R^1$(c)—$R^{3a}$—$R^{4a}$) are those compounds (designated subgenera A(b)—$X^{1-4e}$ and sub-subgenera A(b)—$R^1$(a)—$X^{1-4e}$, A(b)—$R^1$(b)—$X^{1-4e}$, A(b)—$R^1$(c)—$X^{1-4e}$, A(b)—$R^{3a}$—$X^{1-4e}$ and A(b)—$R^{4a}$—$X^{1-4e}$ and sub-sub-subgenera A(b)—$R^1$(a)—$R^{3a}$—$X^{1-4e}$, A(b)—$R^1$(b)—$R^{3a}$—$X^{1-4e}$, A(b)—$R^1$(c)—$R^{3a}$—$X^{1-4e}$, A(b)—$R^1$(a)—$R^{4a}$—$X^{1-4e}$, A(b)—$R^1$ (b)—$R^{4a}$—$X^{1-4e}$, A(b)—$R^1$(c)—$R^{4a}$—$X^{1-4e}$, A(b)—$R^{3a}$—$R^4$—$X^{1-4e}$, and sub-sub-sub-subgenera A(b)—$R^1$(a)—$R^{3a}$—$R^{4a}$—$X^{1-4e}$, A(b)—$R^1$(b)—$R^{3a}$—$R^{4a}$—$X^{1-4e}$, A(b)—$R^1$(c)—$R^{3a}$—$R^{4a}$—$X^{1-4e}$) wherein $X^3$ and $X^4$ each independently selected from hydrogen; halo; ($C_1$–$C_4$)alkyl optionally substituted with 1 to 3 halo; cyano and ($C_1$–$C_4$) alkoxy (wherein $X^{1-4e}$ refers to said preferred $X^3$ and $X^4$).

An embodiment of the present invention includes compounds of formula I, referred to as the A(c) Group compounds, wherein A is (5- to 6-membered)-heteroaryl containing 1 to 2 ring heteroatoms independently selected from the group consisting of —N=, —NR'—, —S—, or —O—; wherein said heteroaryl is fused to a (5- to 6-membered)-heteroaryl containing 1 to 2 ring heteroatoms independently selected from the group consisting of —N=, —NR'—, —S— or —O—; wherein either of said (5- to 6-membered)-heteroaryl or said fused (5- to 6-membered)-heteroaryl is optionally substituted with one to two substituents per ring, wherein said substituents are independently selected from the group consisting of halo, hydroxy, cyano, mercapto, carboxy, nitro, ($C_1$–$C_4$)alkyl, ($C_2$–$C_4$)alkenyl, ($C_2$–$C_4$)alkynyl, ($C_1$–$C_4$)alkoxy, ($C_1$–$C_4$)alkyl-S—, amino, ($C_1$–$C_4$)alkylamino, di[($C_1$–$C_4$)alkyl]amino, amido, ($C_1$–$C_4$)alkylamido, di[($C_1$–$C_4$)alkyl]amido, ($C_1$–$C_4$)alkyl-(C=O)—O—, ($C_1$–$C_4$)alkyl-(C=O)—N(R')—, formyl, ($C_1$–$C_4$)alkyl-(C=O)— and ($C_1$–$C_4$)alkoxy-(C=O)—; wherein R' is hydrogen or ($C_1$–$C_4$)alkyl; wherein each of said ($C_1$–$C_4$)alkyl may optionally be substituted with 1 to 3 substituents independently selected from the group consisting of halo, hydroxy, cyano, mercapto, carboxy, nitro, ($C_1$–$C_4$)alkyl, ($C_2$–$C_4$)alkenyl, ($C_2$–$C_4$)alkynyl, ($C_1$–$C_4$) alkoxy, ($C_1$–$C_4$)alkyl-S—, amino, ($C_1$–$C_4$)alkylamino, di[($C_1$–$C_4$)alkyl]amino, amido, ($C_1$–$C_4$)alkylamido, di[($C_1$–$C_4$)alkyl]amido, ($C_1$–$C_4$)alkyl-(C=O)—O—, ($C_1$–$C_4$)alkyl-(C=O)—N(R')—, formyl, ($C_1$–$C_4$)alkyl-(C=O)— and ($C_1$–$C_4$)alkoxy-(C=O)—.

A subgenus of the embodiment of the A(c) group of compounds are those compounds (designated the subgenus A(c)—$R^1$(a)) wherein A is defined above as A(c) and $R^1$, referred to hereinafter as $R^1$(a), is (5- to 6-membered)-heteroaryl containing 1 to 4 ring heteroatoms independently selected from —N=, —NR'—, —O—, or —S—, wherein said heteroaryl is optionally substituted with 1 to 3 substituents independently selected from the group consisting of halo, hydroxy, cyano, mercapto, carboxy, nitro, ($C_1$–$C_4$) alkyl, ($C_2$–$C_4$)alkenyl, ($C_2$–$C_4$)alkynyl, ($C_1$–$C_4$)alkoxy, ($C_1$–$C_4$)alkyl-S—, amino, ($C_1$–$C_4$)alkylamino, di[($C_1$–$C_4$) alkyl]amino, amido, ($C_1$–$C_4$)alkylamido, di[($C_1$–$C_4$)alkyl] amido, ($C_1$–$C_4$)alkyl-(C=O)—O—, ($C_1$–$C_4$)alkyl-(C=O)—N(R')—, formyl, ($C_1$–$C_4$)alkyl-(C=O)— and ($C_1$–$C_4$)alkoxy-(C=O)—; wherein R' is hydrogen or ($C_1$–$C_4$)alkyl; wherein each of said ($C_1$–$C_4$)alkyl is optionally substituted with 1 to 3 substituents independently selected from the group consisting of halo, hydroxy, cyano, mercapto, carboxy, nitro, ($C_1$–$C_4$)alkyl, ($C_2$–$C_4$)alkenyl, ($C_2$–$C_4$)alkynyl, ($C_1$–$C_4$)alkoxy, ($C_1$–$C_4$)alkyl-S—, amino, ($C_1$–$C_4$)alkylamino, di[($C_1$–$C_4$)alkyl]amino, amido, ($C_1$–$C_4$)alkylamido, di[($C_1$–$C_4$)alkyl]amido, ($C_1$–$C_4$)alkyl-(C=O)—O—, ($C_1$–$C_4$)alkyl-(C=O)—N(R')—, formyl, ($C_1$–$C_4$)alkyl-(C=O)— and ($C_1$–$C_4$)alkoxy-(C=O)—; wherein preferred R' is selected from the group consisting of (5- to 6-membered)- heteroaryl containing 1 to 4 ring heteroatoms independently selected from —N=, —NR'—, —O—, or —S—, wherein said heteroaryl is optionally substituted with 1 to 3 substituents independently selected from the group consisting of halo, ($C_1$–$C_4$)alkyl, ($C_1$–$C_4$) alkoxy, ($C_1$–$C_4$)alkyl-(C=O)—, hydroxy, cyano and amino; wherein R' is hydrogen or ($C_1$–$C_4$)alkyl; wherein each of said ($C_1$–$C_4$)alkyl may optionally be substituted with 1 to 3 halo.

Another subgenus of the embodiment of the A(c) group of compounds are those compounds (designated the subgenus A(c)—$R^1$(b)) wherein A is defined above as A(c) and $R^1$, referred to hereinafter as $R^1$(b), is (5- to 6-membered)-heteroaryl containing 1 to 2 ring heteroatoms independently selected from the group consisting of —N=, —NR'—, —S— or —O—; wherein said heteroaryl is fused to a saturated, partially saturated or aromatic (5- to 7-membered)-carbocyclic ring; wherein either of said (5- to 6-membered)-heteroaryl ring or said fused saturated, partially saturated or aromatic (5- to 7-membered)-carbocyclic ring is optionally substituted with 1 to 2 substituents per ring, wherein said substituents are independently selected from the group consisting of halo, hydroxy, cyano, mercapto, carboxy, nitro, ($C_1$–$C_4$)alkyl, ($C_2$–$C_4$)alkenyl, ($C_2$–$C_4$)alkynyl, ($C_1$–$C_4$)alkoxy, ($C_1$–$C_4$)alkyl-S—, amino, ($C_1$–$C_4$)alkylamino, di[($C_1$–$C_4$)alkyl]amino, amido, ($C_1$–$C_4$)alkylamido, di[($C_1$–$C_4$)alkyl]amido, ($C_1$–$C_4$)alkyl-(C=O)—O—, ($C_1$–$C_4$)alkyl-(C=O)—N(R')—, formyl, ($C_1$–$C_4$)alkyl-(C=O)— and ($C_1$–$C_4$)alkoxy-(C=O)—; wherein R' is hydrogen or ($C_1$–$C_4$)alkyl; wherein each of said ($C_1$–$C_4$)alkyl is optionally substituted with 1 to 3 substituents independently selected from the group consisting of halo, hydroxy, cyano, mercapto, carboxy, nitro, ($C_1$–$C_4$)alkyl, ($C_2$–$C_4$)alkenyl, ($C_2$–$C_4$)alkynyl, ($C_1$–$C_4$) alkoxy, ($C_1$–$C_4$)alkyl-S—, amino, ($C_1$–$C_4$)alkylamino, di[($C_1$–$C_4$)alkyl]amino, amido, ($C_1$–$C_4$)alkylamido, di[($C_1$–$C_4$)alkyl]amido, ($C_1$–$C_4$)alkyl-(C=O)—O—, ($C_1$–$C_4$)alkyl-(C=O)—N(R')—, formyl, ($C_1$–$C_4$)alkyl-(C=O)— and ($C_1$–$C_4$)alkoxy-(C=O)—; wherein preferred R' is selected from the group consisting of (5- to 6-membered)-heteroaryl containing 1 ring heteroatom selected from the group consisting of —N=, —NR'—, —S— or —O—; wherein said heteroaryl is fused to an aromatic (6-membered)-carbocyclic ring; wherein either of said (5- to 6-membered)-heteroaryl ring or said fused aromatic (6-membered)-carbocyclic ring may optionally be substituted with 1 to 2 substituents per ring, wherein said substituents are independently selected from the group consisting of halo and ($C_1$–$C_4$)alkyl; wherein R' is hydrogen or ($C_1$–$C_4$)alkyl.

Another subgenus of the embodiment of the A(c) group of compounds are those compounds (designated the subgenus A(c)—$R^1$(c)) wherein A is as defined above as A(c) and $R^1$, referred to hereinafter as $R^1$(c), is (5- to 6-membered)-heteroaryl containing 1 to 2 ring heteroatoms independently selected from the group consisting of —N=, —NR'—, —S—, or —O—; wherein said heteroaryl is fused to a (5- to 6-membered)-heteroaryl containing 1 to 2 ring heteroatoms independently selected from the group consisting of —N=, —NR'—, —S— or —O—; wherein either of said (5- to 6-membered)-heteroaryl or said fused (5- to 6-membered)-heteroaryl is optionally substituted with one to two substituents per ring, wherein said substituents are independently selected from the group consisting of halo, hydroxy, cyano, mercapto, carboxy, nitro, ($C_1$–$C_4$)alkyl, ($C_2$–$C_4$)alkenyl, ($C_2$–$C_4$)alkynyl, ($C_1$–$C_4$)alkoxy, ($C_1$–$C_4$) alkyl-S—, amino, ($C_1$–$C_4$)alkylamino, di[($C_1$–$C_4$)alkyl] amino, amido, ($C_1$–$C_4$)alkylamido, di[($C_1$–$C_4$)alkyl]amido, ($C_1$–$C_4$)alkyl-(C=O)—O—, ($C_1$–$C_4$)alkyl-(C=O)—N (R')—, formyl, ($C_1$–$C_4$)alkyl-(C=O)— and ($C_1$–$C_4$)alkoxy-(C=O)—; wherein R' is hydrogen or ($C_1$–$C_4$)alkyl; wherein each of said ($C_1$–$C_4$)alkyl is optionally substituted with 1 to 3 substituents independently selected from the group consisting of halo, hydroxy, cyano, mercapto, carboxy, nitro, $(C_1-C_4)$alkyl, $(C_2-C_4)$alkenyl, $(C_2-C_4)$alkynyl, $(C_1-C_4)$alkoxy, $(C_1-C_4)$alkyl-S—, amino, $(C_1-C_4)$alkylamino, di[$(C_1-C_4)$alkyl]amino, amido, $(C_1-C_4)$alkylamido, di[$(C_1-C_4)$alkyl]amido, $(C_1-C_4)$alkyl-(C=O)—O—, $(C_1-C_4)$alkyl-(C=O)—N(R')—, formyl, $(C_1-C_4)$alkyl-(C=O)— and $(C_1-C_4)$alkoxy-(C=O)—.

Another embodiment of the invention of the A(c) group of compounds, including the subgenera A(c)—$R^1$(a), A(c)—$R^1$(b) and A(c)—$R^1$(c), are those compounds wherein A is as defined above as A(c), $R^1$ is as defined above as $R^1$(a, b or c) and one of $R^3$ or $R^4$ is hydrogen (wherein $R^{3,4a}$ refers to $R^3$ as hydrogen and wherein $R^{3,4b}$ refers to $R^4$ as hydrogen). Such subgenera can be designated A(c)—$R^{3,4a}$ and A(c)—$R^{3,4b}$, and sub-subgenera A(c)—$R^1$(a)—$R^{3,4a}$, A(c)—$R^1$(a)—$R^{3,4a}$, A(c)—$R^1$(b)—$R^{3,4a}$, A(c)—$R^1$(b)—$R^{3,4b}$, A(c)—$R^1$(c)—$R^{3,4a}$ and A(c)—$R^1$(c)—$R^{3,4b}$).

Another embodiment of the invention of compounds of the formula A(c) compounds, including the subgenera A(c)—$R^1$(a), A(c)—$R^1$(b), A(c)—$R^1$(c), A(c)—$R^{3,4a}$ and A(c)—$R^{3,4b}$ and sub-subgenera A(c)—$R^1$(a)—$R^{3,4b}$, A(c)—$R^1$(a)—$R^{3,4b}$, A(c)—$R^1$(b)—$R^{3,4a}$, A(c)—$R^1$(b)—$R^{3,4b}$, A(c)—$R^1$(c)—$R^{3,4a}$ and A(c)—$R^1$(c)—$R^{3,4b}$, are those compounds wherein two, three or four of $X^1$, $X^2$, $X^3$ and $X^4$ are hydrogen (wherein $X^{1-4a}$ refers to two of $X^1$–$X^4$ as hydrogen, $X^{1-4b}$ refers to three of $X^1$–$X^4$ as hydrogen and $X^{1-4c}$ refers to four of $X^1$–$X^4$ as hydrogen). Such subgenera can be designated A(c)—$X^{1-4a}$, A(c)—$X^{1-4b}$ A(c)—$X^{1-4c}$. Such sub-subgenera can be designated A(c)—$R^1$(a)—$X^{1-4a}$, A(c)—$R^1$(b)—$X^{1-4a}$, A(c)—$R^1$(c)—$X^{1-4a}$, A(c)—$R^{3,4a}$—$X^{1-4a}$ and A(c)—$R^{3,4b}$—$X^{1-4a}$, A(c)—$R^1$(a)—$X^{1-4b}$, A(c)—$R^1$(b)—$X^{1-4b}$, A(c)—$R^1$(c)—$X^{1-4b}$, A(c)—$R^{3,4a}$—$X^{1-4b}$ and A(c)—$R^{3,4b}$—$X^{1-4b}$, A(c)—$R^1$(a)—$X^{1-4c}$, A(c)—$R^1$(b)—$X^{1-4c}$, A(c)—$R^1$(c)—$X^{1-4c}$, A(c)—$R^{3,4a}$—$X^{1-4c}$ and A(c)—$R^{3,4b}$—$X^{1-4c}$. Sub-sub-subgenera can be designated A(c)—$R^1$(a)—$R^{3,4a}$—$X^{1-4a}$, A(c)—$R^1$(a)—$R^{3,4b}$—$X^{1-4a}$, A(c)—$R^1$(b)—$R^{3,4a}$—$X^{1-4a}$, A(c)—$R^1$(b)—$R^{3,4b}$—$X^{1-4a}$, A(c)—$R^1$(c)—$R^{3,4a}$—$X^{1-4a}$ and A(c)—$R^1$(c)—$R^{3,4b}$—$X^{1-4a}$, A(c)—$R^1$(a)—$R^{3,4a}$—$X^{1-4b}$, A(c)—$R^1$(a)—$R^{3,4b}$—$X^{1-4b}$, A(c)—$R^1$(b)—$R^{3,4a}$—$X^{1-4b}$, A(c)—$R^1$(b)—$R^{3,4b}$—$X^{1-4b}$, A(c)—$R^1$(c)—$R^{3,4a}$—$X^{1-4b}$ and A(c)—$R^1$(c)—$R^{3,4b}$—$X^{1-4b}$, A(c)—$R^1$(a)—$R^{3,4a}$—$X^{1-4c}$, A(c)—$R^1$(a)—$R^{3,4b}$—$X^{1-4c}$, A(c)—$R^1$(b)—$R^{3,4a}$—$X^{1-4c}$, A(c)—$R^1$(b)—$R^{3,4b}$—$X^{1-4c}$, A(c)—$R^1$(c)—$R^{3,4a}$—$X^{1-4c}$ and A(c)—$R^1$(c)—$R^{3,4b}$—$X^{1-4c}$.

A group of compounds which is preferred among the A(c) Group compounds, including subgenera A(c)—$R^1$(a), A(c)—$R^1$(b), A(c)—$R^1$(c), are those compounds (designated subgenera A(c)—$R^{3a}$, and sub-subgenera A(c)—$R^1$(a)—$R^{3a}$, A(c)—$R^1$(b)—$R^{3a}$, A(c)—$R^1$(c)—$R^{3a}$ including any preferences) wherein A is as defined above as A(c), $R^1$ is as defined above as $R^1$ (a, b or c) and $R^3$ is selected from hydrogen; halo; $(C_1-C_4)$alkyl optionally substituted with 1 to 3 halo; $(C_1-C_4)$alkoxy; $(C_1-C_4)$alkyl-O—C(=O)— and cyano (wherein said preferred $R^3$ is referred to as $R^{3a}$).

Another group of compounds which is preferred among the A(c) Group of compounds, including subgenera A(c)—$R^1$(a), A(c)—$R^1$(b), A(c)—$R^1$(c), A(c)—$R^{3a}$, sub-subgenera A(c)—$R^1$(a)—$R^{3a}$, A(c)—$R^1$(b)—$R^{3a}$, A(c)—$R^1$(c)—$R^{3a}$, are those compounds (designated subgenera A(c)—$R^{4a}$, and sub-subgenera A(c)—$R^1$(a)—$R^{4a}$, A(c)—$R^1$(b)—$R^{4a}$, A(c)—$R^1$(c)—$R^{4a}$, A(c)—$R^1$(a)—$R^{3a}$—$R^{4a}$, A(c)—$R^1$(b)—$R^{3a}$—$R^{4a}$, A(c)—$R^1$(c)—$R^{3a}$—$R^{4a}$), wherein A is as defined above as A(c), $R^1$ is as defined above as $R^1$(a, b or c), $R^3$ is defined above as $R^3$ and $R^4$ is selected from hydrogen; halo; $(C_1-C_4)$alkyl optionally substituted with 1 to 3 halo; $(C_1-C_4)$alkoxy; $(C_1-C_4)$alkyl-O—C(=O)— and cyano (wherein said preferred $R^4$ is $R^{4a}$).

Another group of compounds which is preferred among each A(c) Group of compounds, including subgenera A(c)—$R^1$(a), A(c)—$R^1$ (b), A(c)—$R^1$(c), A(c)—$R^{3a}$, A(c)—$R^{4a}$, sub-subgenera A(c)—$R^1$(a)—$R^{3a}$, A(c)—$R^1$(b)—$R^{3a}$, A(c)—$R^1$(c)—$R^{3a}$, A(c)—$R^1$(a)—$R^{4a}$, A(c)—$R^1$(b)—$R^{4a}$, A(c)—$R^1$(c)—$R^{4a}$, and A(c)—$R^{3a}$—$R^{4a}$, and sub-sub-subgenera A(c)—$R^1$(a)—$R^{3a}$—$R^{4a}$, A(c)—$R^1$(b)—$R^{3a}$—$R^{4a}$, A(c)—$R^1$(c)—$R^{3a}$—$R^4$,) are those compounds (designated subgenera A(c)—$X^1$ and sub-subgenera A(c)—$R^1$(a)—$X^{1-4d}$, A(c)—$R^1$(b)—$X^{1-4d}$, A(c)—$R^1$(c)—$X^{1-4d}$, A(c)—$R^{3a}$—$X^{1-4d}$ and A(c)—$R^{4a}$—$X^{1-4d}$ and sub-sub-subgenera A(c)—$R^1$(a)—$R^{3a}$—$X^{1-4d}$, A(c)—$R^1$(b)—$R^{3a}$—$X^{1-4d}$, A(c)—$R^1$(c)—$R^{3a}$—$X^{1-4d}$, A(c)—$R^1$(a)—$R^{4a}$—$X^{1-4d}$, A(c)—$R^1$(b)—$R^{4a}$—$X^{1-4d}$, A(c)—$R^1$(c)—$R^{4a}$—$X^{1-4d}$, A(c)—$R^{3a}$—$R^{4a}$—$X^{1-4d}$, and sub-sub-sub-subgenera A(c)—$R^1$(a)—$R^{3a}$—$R^{4a}$—$X^{1-4d}$, A(c)—$R^1$(b)—$R^{3a}$—$R^{4a}$—$X^{1-4d}$, A(c)—$R^1$(c)—$R^{3a}$—$R^{4a}$—$X^{1-4d}$) wherein $X^1$ and $X^2$ are each independently selected from hydrogen; halo; $(C_1-C_4)$alkyl optionally substituted with 1 to 3 halo; cyano and $(C_1-C_4)$alkoxy (wherein $X^{1-4d}$ refers to said preferred $X^1$ and $X^2$).

A group of compounds which is preferred among each A(c) Group of compounds, including subgenera A(c)—$R^1$ (a), A(c)—$R^1$(b), A(c)—$R^1$(c), A(c)—$R^{3a}$, A(c)—$R^{4a}$, sub-subgenera A(c)—$R^1$(a)—$R^{3a}$, A(c)—$R^1$(b)—$R^{3a}$, A(c)—$R^1$(c)—$R^{3a}$, A(c)—$R^1$(a)—$R^{4a}$, A(c)—$R^1$(b)—$R^{4a}$, A(c)—$R^1$(c)—$R^{4a}$, A(c)—$R^{3a}$—$R^{4a}$, and sub-subgenera A(c)—$R^1$(a)—$R^{3a}$—$R^{4a}$, A(c)—$R^1$(b)—$R^{3a}$—$R^{4a}$, A(c)—$R^1$(c)—$R^{3a}$—$R^{4a}$) are those compounds (designated subgenera A(c)—$X^{1-4e}$ and sub-subgenera A(c)—$R^1$(a)—$X^{1-4e}$, A(c)—$R^1$(b)—$X^{1-4e}$, A(c)—$R^1$(c)—$X^{1-4e}$, A(c)—$R^{3a}$—$X^{1-4e}$ and A(c)—$R^{4a}$—$X^{1-4e}$ and sub-sub-subgenera A(c)—$R^1$(a)—$R^{3a}$—$X^{1-4e}$, A(c)—$R^1$(b)—$R^{3a}$—$X^{1-4e}$, A(c)—$R^1$(c)—$R^{3a}$—$X^{1-4e}$, A(c)—$R^1$(a)—$R^{4a}$—$X^{1-4e}$, A(c)—$R^1$(b)—$R^{4a}$—$X^{1-4e}$, A(c)—$R^1$(c)—$R^{4a}$—$X^{1-4e}$, A(c)—$R^{3a}$—$R^{4a}$—$X^{1-4e}$, and sub-sub-sub-subgenera A(c)—$R^1$(a)—$R^3$a-$R^{4a}$—$X^{1-4e}$, A(c)—$R^1$(b)—$R^{3a}$—$R^{4a}$—$X^{1-4e}$, A(c)—$R^1$(c)—$R^{3a}$—$R^{4a}$—$X^{1-4e}$) wherein $X^3$ and $X^4$ are each independently selected from hydrogen; halo; $(C_1-C_4)$alkyl optionally substituted with 1 to 3 halo; cyano and $(C_1-C_4)$alkoxy (wherein $X^{1-4e}$ refers to said preferred $X^3$ and $X^4$).

A preferred group of compounds of this invention consists of those compounds of formula I, wherein

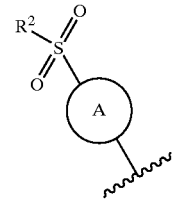

is selected from the group consisting of

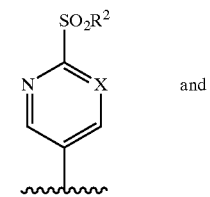

A1 and

-continued

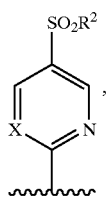
A2 wherein X is CH or N, and the heteroaryl moiety is unsubstituted, mono-, di- or tri-substituted with substituents independently selected from the group consisting of halo and $(C_1-C_4)$alkyl;

a) $R^1$ is heteroaryl selected from the group consisting of furyl, thiazolyl, oxazolyl, thienyl, tetrazolyl, triazolyl, imidazolyl, benzofuranyl and benzothienyl, wherein said heteroaryl is unsubstituted, mono-, di- or tri-substituted with substituents independently selected from the group consisting of halo and $(C_1-C_4)$alkyl;

$R^2$ is $NH_2$;

$R^3$ and $R^4$ are independently selected from the group consisting of hydrogen, halo and $(C_1-C_4)$alkyl optionally substituted with 1 to 3 halo; and $X^1$, $X^2$, $X^3$ and $X^4$ are independently selected from the group consisting of hydrogen, halo, methyl, ethyl, methoxy, trifluoromethyl, amino-C(=O)— and cyano.

A more preferred group of compounds of this invention consists of those compounds of formula I, wherein

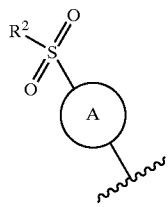

is selected from the group consisting of

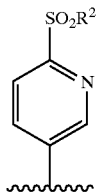 and 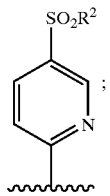;

$R^1$ is selected from furyl, thiazolyl and oxazoleyl;
$R^2$ is $NH_2$;
$R^3$ and $R^4$ are each independently selected from hydrogen, chloro, fluoro, ethyl, and trifluoromethyl; and
$X^1$, $X^2$, $X^3$ and $X^4$ are independently selected from hydrogen, chloro, fluoro and methyl.

Preferred compounds of this invention include
6-[5-[4-(2-Furyl)phenyl]-3-(trifluoromethyl)-1H-pyrazol-1-yl]-3-pyrdinesulfonamide;
5-[5-[4-(2-Furyl)phenyl]-3-(trifluoromethyl)-1H-pyrazol-1-yl]-2-pyridinesulfonamide;
5-[5-[3-Chloro-4-(1,3-oxazol-2-yl)phenyl]-3-(trifluoromethyl)-1H-pyrazol-1-yl]-2-pyridinesulfonamide;
5-{4-Chloro-5-[4-(1,3-thiazol-4-yl)phenyl]-3-(trifluoromethyl)-1H-pyrazol-1-yl}-2-pyridinesulfonamide;
5-{5-[4-(1,3-Thiazol-4-yl)phenyl]-3-(trifluoromethyl)-1H-pyrazol-1-yl}-2-pyridinesulfonamide;
5-{5-Ethyl-[4-(1,3-thiazol-4-yl)phenyl]-3-(trifluoromethyl)-1H-pyrazol-1-yl}-2-pyridinesulfonamide;
5-[4-Ethyl-5-[4-(1,3-thiazol-5-yl)phenyl]-3-(trifluoromethyl)-1H-pyrazol-1-yl]-2-pyridinesulfonamide;
5-{4-Fluoro-5-[4-(1,3-thiazol-4-yl)phenyl]-3-(trifluoromethyl)-1H-pyrazol-1-yl}-2-pyridinesulfonamide;
5-[5-[4-(1,3-Thiazol-5-yl)phenyl]-3-(trifluoromethyl)-1H-pyrazol-1-yl]-2-pyridinesulfonamide;
5-{4-Fluoro-5-[4-(1,3-thiazol-5-yl)phenyl]-3-(trifluoromethyl)-1H-pyrazol-1-yl}-2-pyridinesulfonamide;
5-[5-Chloro-4-(1,3-thiazole-4-yl)phenyl]-3-(trifluoromethyl)-1H-pyrazol-1-yl]-2-pyridinesulfonamide;
5-[5-Chloro-4-(1,3-thiazole-5-yl)phenyl]-3-(trifluoromethyl)-1H-pyrazol-1-yl]-2-pyridinesulfonamide;
5-[4-Chloro-5-[3-chloro-4-(1,3-thiazol-5-yl)phenyl]-3-trifluoromethyl-1H-pyrazol-1-yl]-2-pyridinesulfonamide;
6-[5-[3-Methyl-4-(1,3-thiazol-4-yl)phenyl]-3-(trifluoromethyl)-1H-pyrazol-1-yl]-3-pyridinesulfonamide hydrochloride;
5-[5-[3-Methyl-4-(1,3-thiazol-4-yl)phenyl]-3-trifluoromethyl-1H-pyrazol-1-yl]-2-pyridinesulfonamide;
5-(4-Ethyl-5-(3-fluoro-4-(1,3-thiazol-5-yl)phenyl)-3-trifluoromethyl-1H-pyrazol-1-yl)-2-pyridinesulfonamide; and
5-(5-(3-Chloro-4-(2-furyl)phenyl)-3-(trifluoromethyl)-1H-pyrazol-1-yl)-2-pyridinesulfonamide; or its salts.

An even more preferred compounds of this invention are those compounds of formula I wherein

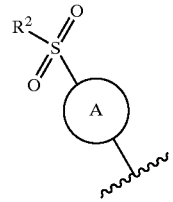

is selected from the group consisting of

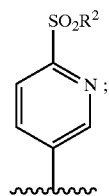;

$R^1$ is selected from furyl, thiazolyl and oxazolyl;
$R^2$ is $NH_2$;
$R^3$ is trifluoromethyl;

$R^4$ is selected from hydrogen, fluoro and ethyl;

$X^1$ and $X^2$ are each independently selected from hydrogen and chloro; and $X^3$ and $X^4$ are both hydrogen.

Individual preferred compounds in the group are

5-[5-[4-(2-Furyl)phenyl]-3-(trifluoromethyl)-1H-pyrazol-1-yl]-2-pyridinesulfonamide;

5-[5-[3-Chloro-4-(1,3-oxazol-2-yl)phenyl]-3-(trifluoromethyl)-1H-pyrazol-1-yl]-2-pyridinesulfonamide;

5-[4-Ethyl-5-[4-(1,3-thiazol-5-yl)phenyl]-3-(trifluoromethyl)-1H-pyrazol-1-yl]-2-pyridinesulfonamide;

5-{4-Fluoro-5-[4-(1,3-thiazol-4-yl)phenyl]-3-(trifluoromethyl)-1H-pyrazol-1-yl}-2-pyridinesulfonamide hydrochloride;

5-[5-[4-(1,3-Thiazol-5-yl)phenyl]-3-(trifluoromethyl)-1H-pyrazol-1-yl]-2-pyridinesulfonamide;

5-[5-Chloro-4-(1,3-thiazole-4-yl)phenyl]-3-(trifluoromethyl)-1H-pyrazol-1-yl]-2-pyridinesulfonamide;

5-[5-Chloro-4-(1,3-thiazole-5-yl)phenyl]-3-(trifluoromethyl)-1H-pyrazol-1-yl]-2-pyridinesulfonamide;

5-[5-[3-Methyl-4-(1,3-thiazol-4-yl)phenyl]-3-trifluoromethyl-1H-pyrazol-1-yl]-2-pyridinesulfonamide;

5-(4-Ethyl-5-(3-fluoro-4-(1,3-thiazol-5-yl)phenyl)-3-trifluoromethyl-1H-pyrazol-1-yl)-2-pyridinesulfonamide; and 5-(5-(3-Chloro-4-(2-furyl)phenyl)-3-(trifluoromethyl)-1H-pyrazol-1-yl)-2-pyridinesulfonamide; or its salts.

This invention also relates to method of treating or preventing diseases or conditions in a mammal, comprising administering a compound of formula I to the mammal, wherein the disease or condition is selected from the group consisting of diseases or conditions in which prostaglandins are implicated as pathogens, pain, fever, inflammation, rheumatic fever, symptoms associated with influenza and other viral infections, common cold, low back and neck pain, dysmenorrhea, headache, toothache, sprains and strains, myositis, neuralgia, synovitis, arthritis including rheumatoid arthritis, degenerative joint disease or osteoarthritis, gout and ankylosing spondylitis, bursitis, burns, injuries following surgical and dental procedures, disease or conditions associated with cellular neoplastic transformations and metastic tumor growth, cancer, colorectal cancer, breast and skin cancer, familiar adenomatous polyposis, cyclooxygenase-mediated proliferation disorders, cyclooxygenase-mediated proliferation disorders in diabetic retinopathy and tumor angiogenesis, prostaniod-induced smooth muscle contraction mediated by synthesis of contractile prostanoids, dysmenorrhea, premature labor, asthma, eosinophil related disorders, neurodegenerative diseases, Alzheimer's and Parkinson's disease, bone loss, osteoarthritis, peptic ulcers, gastritis, regional enterotis, ulcerative colitis, diverticulitis, recurrent of gastrointestinal lesions, gastrointestinal bleeding, coagulation, anemia, hypoprothrombinemia, haemophilia, bleeding problems; kidney disease and conditions prior to surgery of taking of anticoagulants.

This invention relates to a method for treating or preventing a disease or condition wherein the disease or condition is selected from the group consisting of diseases or conditions in which prostaglandins are implicated as pathogens, pain, fever, inflammation, rheumatic fever, symptoms associated with influenza and other viral infections, common cold, low back and neck pain, dysmenorrhea, headache, toothache, sprains and strains, myositis, neuralgia, synovitis, arthritis including rheumatoid arthritis, degenerative joint disease or osteoarthritis, gout and ankylosing spondylitis, bursitis, burns, injuries following surgical and dental procedures, disease or conditions associated with cellular neoplastic transformations and metastic tumor growth, cancer, colorectal cancer, breast and skin cancer, familiar adenomatous polyposis, cyclooxygenase-mediated proliferation disorders, cyclooxygenase-mediated proliferation disorders in diabetic retinopathy and tumor angiogenesis, prostaniod-induced smooth muscle contraction mediated by synthesis of contractile prostanoids, dysmenorrhea, premature labor, asthma, eosinophil related disorders, neurodegenerative diseases, Alzheimer's and Parkinson's disease, bone loss, osteoarthritis, peptic ulcers, gastritis, regional enterotis, ulcerative colitis, diverticulitis, recurrent of gastrointestinal lesions, gastrointestinal bleeding, coagulation, anemia, hypoprothrombinemia, haemophilia, bleeding problems; kidney disease and conditions prior to surgery of taking of anticoagulants.

This invention also relates to a pharmaceutical composition for treating or preventing a disease or condition selected from the group consisting of diseases or conditions in which prostaglandins are implicated as pathogens, pain, fever, inflammation, rheumatic fever, symptoms associated with influenza and other viral infections, common cold, low back and neck pain, dysmenorrhea, headache, toothache, sprains and strains, myositis, neuralgia, synovitis, arthritis including rheumatoid arthritis, degenerative joint disease or osteoarthritis, gout and ankylosing spondylitis, bursitis, burns, injuries following surgical and dental procedures, disease or conditions associated with cellular neoplastic transformations and metastic tumor growth, cancer, colorectal cancer, breast and skin cancer, familiar adenomatous polyposis, cyclooxygenase-mediated proliferation disorders, cyclooxygenase-mediated proliferation disorders in diabetic retinopathy and tumor angiogenesis, prostaniod-induced smooth muscle contraction mediated by synthesis of contractile prostanoids, dysmenorrhea, premature labor, asthma, eosinophil related disorders, neurodegenerative diseases, Alzheimer's and Parkinson's disease, bone loss, osteoarthritis, peptic ulcers, gastritis, regional enterotis, ulcerative colitis, diverticulitis, recurrent of gastrointestinal lesions, gastrointestinal bleeding, coagulation, anemia, hypoprothrombinemia, haemophilia, bleeding problems; kidney disease and conditions prior to surgery of taking of anticoagulants.

General Synthesis

Compounds of general formula (I) may be prepared by a variety of synthetic routes. Representative preparation procedures are outlined below. Unless otherwise indicated, A, $R^1$, $R^2$, $R^3$, $R^4$, $X^1$, $X^2$, $X^3$ and $X^4$ are as defined herein above.

In a desired reaction step of the processes described hereafter, NH or hydroxy protections and removals of the protecting groups used may be carried out according to known procedures such as those described in Protective Groups in Organic Synthesis edited by T. W. Greene et al. (John Wiley & Sons, 1991). Isolated hydroxy groups can generally be protected as ethers including t-butyldimethylsilyl ethers, acetals and esters. In general, benzyl-type protecting groups are removed by hydrogenolysis, silyl esthers by reaction with fluoride ions or under slightly acidic conditions and several 2-substituted ethyl ethers can be cleaved by beta-elimination reactions.

Scheme 1 illustrates preparation methods of compounds of formula I through pyrazole ring formation.

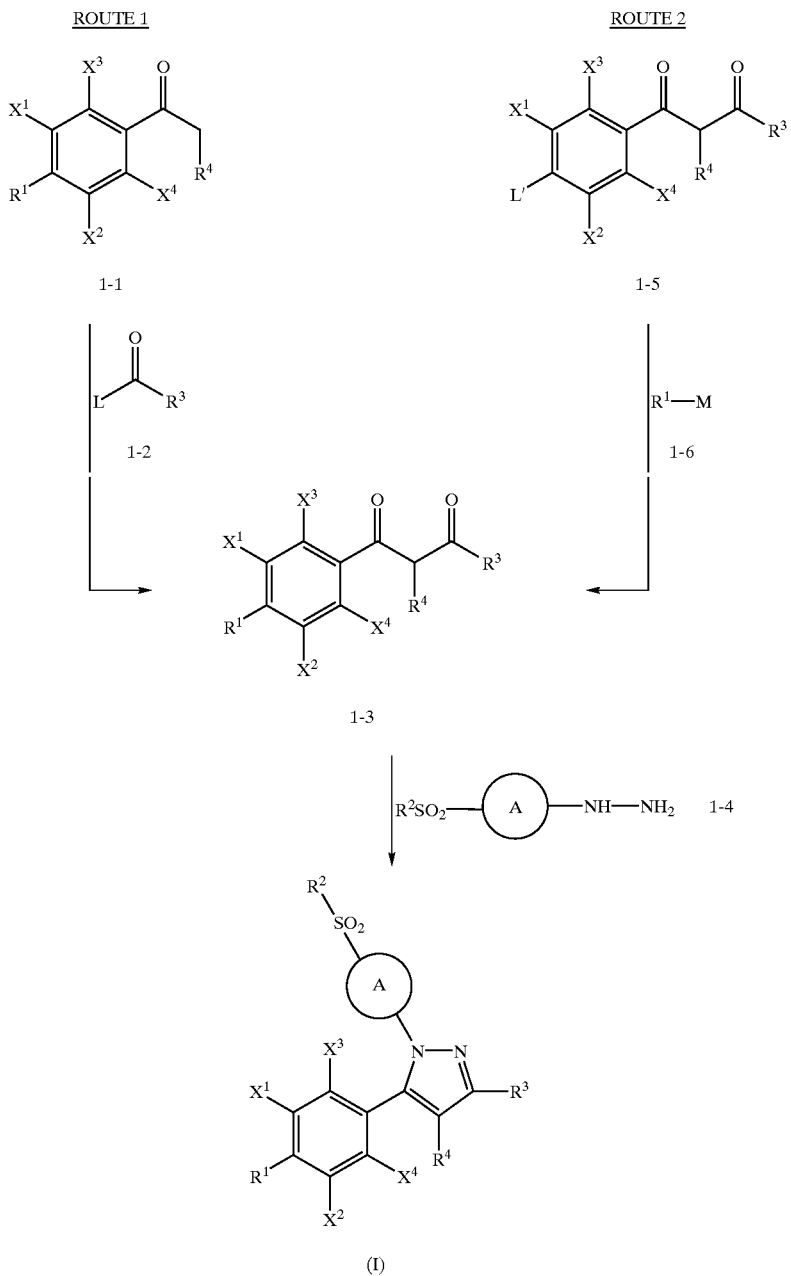

Route 1 (Acylation and Pyrazole-ring Formation):
Referring to Route 1, a compound of the formula I may be prepared by reacting a diketone compound of formula 1-3 with a hydrazine compound of the formula 1-4 in a reaction inert solvent. Suitable solvents used in this reaction include alcohols such as ethanol, trifluoroethanol, methanol, propanol, isopropanol and butanol; dimethyl sulfoxide (DMSO); N,N-dimethylformamide (DMF); acetic acid; N,N-dimethylacetamide (DMA) and N-methyl-2-pyrrolidinone (NMP). Preferred solvents used in this reaction are methanol, ethanol and acetic acid. This reaction may be conducted in the presence of a stoichiometric or catalytic amount of acid such as hydrochloric acid, acetic acid, trifluoroacetic acid, p-toluenesulfonic acid or sulfuric acid, preferably acetic acid. Alternatively, a compound of formula 1-4 may be subjected to the reaction as an acid addition salt such as hydrochloride. This reaction is generally carried out at a temperature from about 0° C. to about 140° C., preferably at about the reflux temperature of the solvent for from about 2 to about 20 hours.

A compound of formula 1-3 is prepared from a compound of formula 1-1 by reaction with a compound of the formula 1-2 wherein L is a suitable leaving group in the presence of a suitable base and a reaction inert solvent. Compounds of formula 1-2 may be subjected to the reaction as esters; or ester equivalents such as acylimidazole; dialkylamide;

halides; thioesters or acid anhydride. A compound of formula 1-2 is preferably used in this reaction as an acylimidazole or ester. Suitable bases used in this reaction include n-butyl lithium, potassium carbonate ($K_2CO_3$), sodium carbonate ($Na_2CO_3$), cesium carbonate ($Cs_2CO_3$), sodium hydride (NaH), sodium methoxide, potassium-tert-butoxide, lithium diisopropylamide (LDA), pyrrolidine, piperidine, lithium 1,1,1,3,3,3-hexamethyldisilazane (($Me_3Si_2)_2NLi$) and the like. A preferred base is sodium methoxide. This reaction can be carried out in a solvent such as a di-(alkyl) ether (preferred is methyl tert-butyl ether), tetrahydrofuran (THF), dimethoxyethane (DME), 1,4-dioxane, methanol, dichloromethane, dimethylformamide (DMF), dimethylacetamide (DMA), or DMSO. Reaction temperature ranges from about –100° to about 150° C. preferably from about 0° C. to about 50° C., more preferably at about room temperature (i.e., from about 20° C. to about 25° C.) for from about 0.5 to 20 hours.

Route 2 ($R^1$-moiety Introduction and Pyrazole-ring Formation):

As illustrated in Route 2, a compound of formula I may also be prepared by (1) a cross-coupling-reaction of a compound of formula 1-5, wherein L' is a suitable leaving group, with a compound of formula 1-6 followed by (2) pyrazole ring formation with a hydrazine compound of formula 1-4 as described herein above. In the cross-coupling reaction, a compound of formula 1-5 may be coupled with compounds of formula 1-6 under reaction conditions known to those skilled in the art. Typical compounds of formula 1-6 used in this reaction include boronic acid (so called Suzuki reaction), zinc halide (so called Negishi reaction), and tin (IV) derivatives (so called Stille reaction) and the like (for examples refer to Tetrahedron, Vol. 54, pp. 263–303, 1998; S. P. Stanforth). A suitable leaving group L' includes halogen, such as chloro, bromo or iodo, preferably iodo, or trifluorosulfonyloxy ($CF_3SO_3$—).

When a compound of formula 1-6 is a boronic acid derivative the reaction is typically run in the presence of a suitable base and a palladium catalyst. A suitable base includes, but is not limited to, potassium hydroxide, thallium hydroxide, sodium or potassium bicarbonate, or an alkyl amine such as, but not limited to, triethylamine. Palladium catalysts typically employed include, for example, tetrakis(triphenylphosphine)palladium and dichlorobis(triphenylphosphine)palladium. Suitable solvents used in this reaction include, but is not limited to, benzene, toluene, dimethoxyethane (DME), 1,4-dioxane and dimethylformamide (DMF), preferably DME. Alternatively, the reaction may be conducted in biphasic media, for example, DME/water or 1,4-dioxane/water, preferably DME/water. The reaction is usually carried out at reflux temperature of solvent, however, lower or higher temperatures may be employed. Reaction time is typically for from 10 minutes to several days, usually for from 30 minutes to 15 hours.

When a compound of formula 1-6 is a zinc halide derivative the reaction is typically run in a suitable reaction inert solvent in the presence of a palladium or nickel catalyst. Suitable catalysts include, for example, tetrakis(triphenylphosphine)palladium, tetrakis(triphenylphosphine)nickel, dichlorobis(triphenylphosphine)palladium, dichlorobis(1,1-bis(diphenylphosphino)ferrocene)palladium, or dichlorobis(1,4-bis(diphenylphosphino)butane)palladium. Suitable solvents used in this reaction include, but is not limited to, tetrahydrofuran (THF), diethylether and dimethoxyethane (DME), preferably THF. The reaction is usually carried out at reflux temperature of solvent, however, lower or higher temperatures may be employed. Reaction time is typically for from about 10 minutes to several days, usually for from about 30 minutes to 15 hours.

When a compound of formula 1-6 is a tin (IV) derivative, for example, $Me_3Sn—R^1$ or $Bu_3Sn—R^1$, the reaction is typically run in a suitable reaction inert solvent in the presence a palladium catalyst. Palladium catalysts typically employed include, for example, tetrakis(triphenylphosphine)palladium and dichlorobis(triphenylphosphine)palladium. If necessary, a co-catalyst such as lithium chloride, ammonium hydroxide or copper(I) bromide may be used. Suitable solvents used in this reaction include, but is not limited to, benzene, toluene, dimethoxyethane (DME), 1,4-dioxane, tetrahydrofuran (THF) and dimethylformamide (DMF), preferably DME or 1,4-dioxane. The reaction is usually carried out at reflux temperature of solvent, however, lower or higher temperatures may be employed. Reaction time is typically for from 10 minutes to several days, usually for from 30 minutes to 15 hours.

Alternatively, compounds of formula 1-3 may also be prepared by heteroaryl-ring formation on a corresponding acyl phenol, acyl halobenzene or N-formylmethylbenzamide compounds and acylation at para-position on the phenyl ring. The ring formations include (a) thiazole ring formation; (b) oxazole ring formation; (c) triazole ring formation; and (d) imidazole ring formation.

(a) Thiazole Ring Formation:

The thiazole ring formation can typically be carried out by first introducing a leaving group such as halo into the acyl moiety then reacting the compound thus obtained with either phosphorus pentasulfide in the presence of formamide, or thioacetoamide. These reactions can be carried out in a reaction inert solvent such as dioxane under reflux.

(b) Oxazole Ring Formation:

The oxazole ring formation can typically be carried out by treating a 2-halo-1-phenyl-butanone compound in the presence of ammonium formate in formic acid under reflux. The oxazole ring formation may also be carried out treating an N-formylmethylbenzamide compound in the presence of triphenylphosphine, iodine and triethylamine.

(c) Triazole Ring Formation:

Compounds of formula 1-1 wherein $R^1$ is triazolyl may be prepared by reacting a cyano benzene compound with trimethylsilyldiazomethane in the presence of n-butyl lithium in a mixture of hexane and diethyl ether at about 0° C.

(d) Imidazole Ring Formation:

Compounds of formula I wherein $R^1$ is imidazolyl may be prepared by reacting a known halomethyl-carbonyl-benzene compound (e.g., those compounds described in *Justus Liebigs Ann. Chem.*, 1941, 546, 277 by Herbert) with formamide in water at about 140° C.

The latter acylation may be carried out by methods known to those skilled in the art or methods illustrated in Route 1 of Scheme 1.

Starting materials used in the processes in Scheme 1 are known compounds or readily prepared by methods known to those skilled in the art (e.g., *Collection Czechoslov. Chem. Common.* Vol. 37, p. 1721, 1972 by J. Vavrina et al.).

Scheme 2 illustrates an alternate method for preparing compounds of formula I.

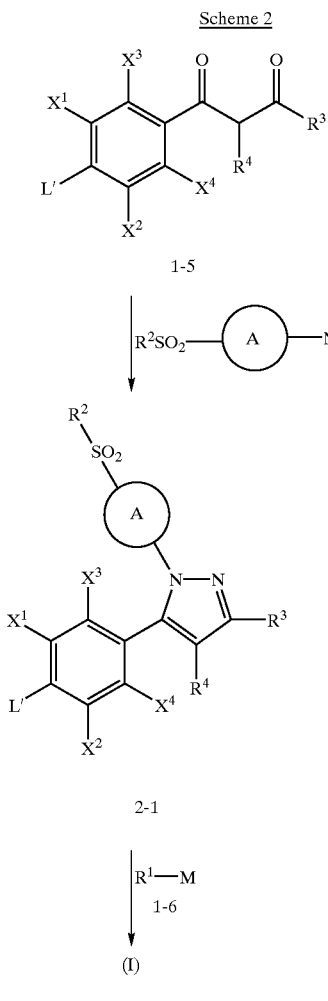

Thus, a compound of formula I may also be prepared by a cross-coupling reaction of a compound of formula 2-1, wherein L' is a suitable leaving group, with a compound of formula 1-6. In the cross-coupling reaction, a compound of formula 2-1 may be coupled with compounds of formula 1-6 under reaction conditions known to those skilled in the art. Typical compounds of formula 1-6 used in this reaction include boronic acid (so called Suzuki reaction), zinc halide (so called Negishi reaction), and tin (IV) derivatives (so called Stille reaction) and the like (for examples refer to Tetrahedron, Vol. 54, pp. 263–303, 1998; S. P. Stanforth). A suitable leaving group L' includes halogen, such as chloro, bromo or iodo, preferably iodo, or trifluorosulfonyloxy ($CF_3SO_3-$). Procedures typically employed are analogous to those described herein before in route 2 (Scheme 1).

A compound of formula 2-1 is readily prepared from a compound of formula 1-5 and a compound of formula 1-4 according to analogous procedures illustrated in Scheme 1 described herein before.

In another embodiment, compounds of formula I may be prepared as illustrated in Scheme 3.

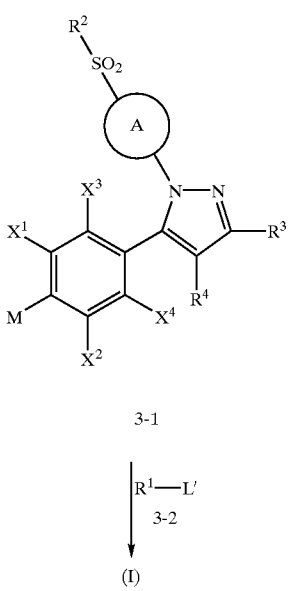

Thus, a compound of formula I may also be prepared by a cross-coupling reaction of a compound of formula 3-1, wherein M is a boronic acid (e.g., $-B(OH)_2$), a zinc halide (e.g., $-ZnCl$) or a tin (IV) (e.g., $-Sn(n-Bu)_3$) derivative, with a compound of formula 3-2, wherein L' is a suitable leaving group, such as chloro, bromo or iodo, preferably iodo, or trifluorosulfonyloxy ($CF_3SO_3-$). In the cross-coupling reaction, a compound of formula 3-1 may be coupled with compounds of formula 3-2 under reaction conditions known to those skilled in the art. Compounds of formula 3-1 are readily prepared from compounds of formula 2-1 (Scheme 2) by standard metal-halogen exchange reactions known to those skilled in the art.

Alternatively, compounds of formula I may be prepared as illustrated in Scheme 4.

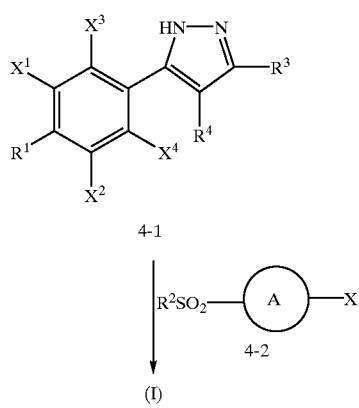

According to Scheme 4, a pyrazole compound of formula 4-1 may be coupled with a compound of formula 4-2 wherein X is halo, for example, fluoro, bromo or iodo, to yield a compound of formula I. The coupling reaction is usually carried out in the presence of a suitable base such as n-butyllithium (n-BuLi) sodium hydride, potassium carbonate, cesium carbonate, potassium tert-butoxide, triethylamine, pyridine, or the like. A suitable reaction inert solvent includes, but is not limited to, tetrahydrofuran (THF), dimethoxyethane (DME), dimethyl sulfoxide (DMSO), dimethylformamide (DMF) or toluene. The reaction is usually carried out at reflux temperature of solvent, however, lower or higher temperatures may be employed. Reaction time is typically for from 10 minutes to several days, usually for from 30 minutes to 15 hours. If desired, a catalyst such as copper (II) oxide or copper (II) bromide may be added to the reaction mixture. Compounds of formula 4-1 may be prepared according to similar procedures illustrated in Scheme 1 described herein before.

Compounds of formula I may also be prepared according to the procedures illustrated in Scheme 5 through oxidation.

to the reflux temperature of the reaction mixture for from about 10 minutes to about 30 hours. Preferably, the reaction may be carried out at a temperature in the range of 0° to 50° C. for from about 1 to 20 hours. Suitable oxidizing reagents include mCPBA (m-chloroperoxybenzoic acid), peracetic acid, hydrogen peroxide and oxone. Preferred is mCPBA. Compounds of formula 5-1 may be prepared according to the procedures of Scheme 1 except that a sulfide hydrazine compound of formula 5-2 is used instead of a sulfonyl hydrazine compound of formula 1-4.

Route 2 (Oxidation and $R^1$-moiety Introduction):

According to Route 2, compounds of formula 5-4 may be oxidized to compounds of formula 5-5 (2-1) and then converted to compounds of formula I by introducing $R^1$ group. The oxidization of compounds of formula 5-4 may be carried out according to the similar procedures as illustrated in Route 1 (Scheme 5). Compounds of formula 5-5 (2-1)

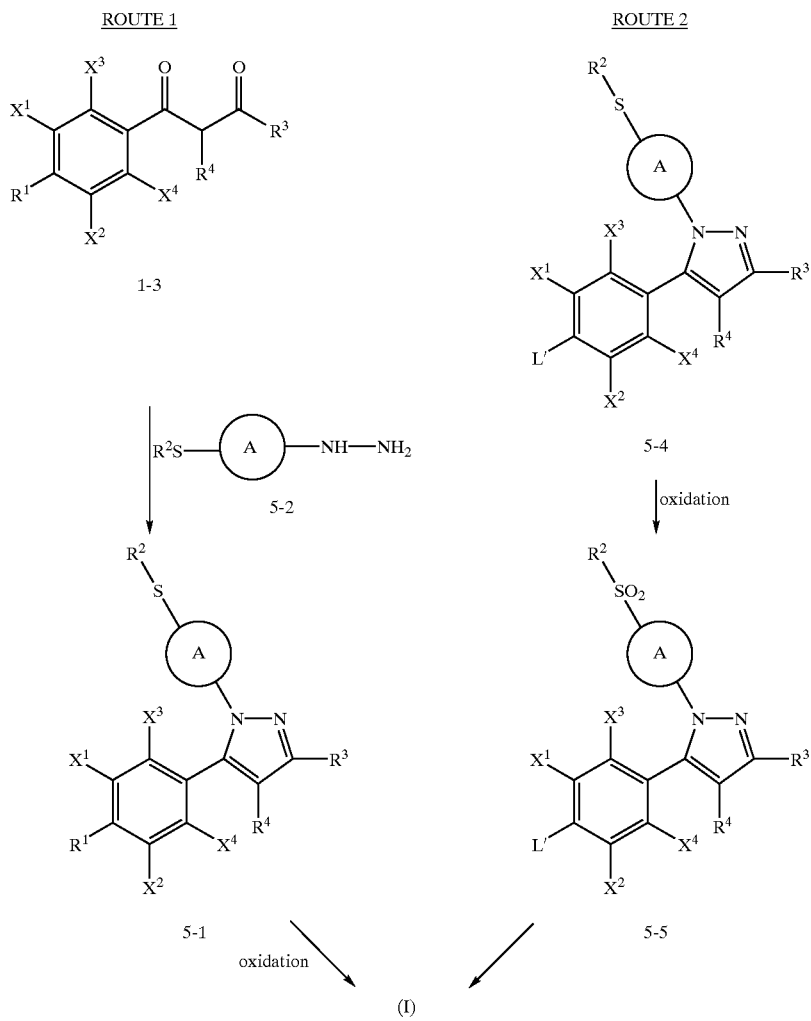

Route 1 (Pyrazole-ring Formation and Oxidation):

According to Route 1, a sulfide compound of formula 5-1 may be oxidized to the compound of formula I using a suitable oxidizing reagent in a reaction inert solvent. This reaction is usually carried out at a temperature from −20° C.

may be converted to compounds of formula I by coupling reaction with a desired coupling reagent comprising $R^1$ group according to procedures known to those skilled in the art or similar procedures as illustrated in Scheme 1 and the discussed herein before.

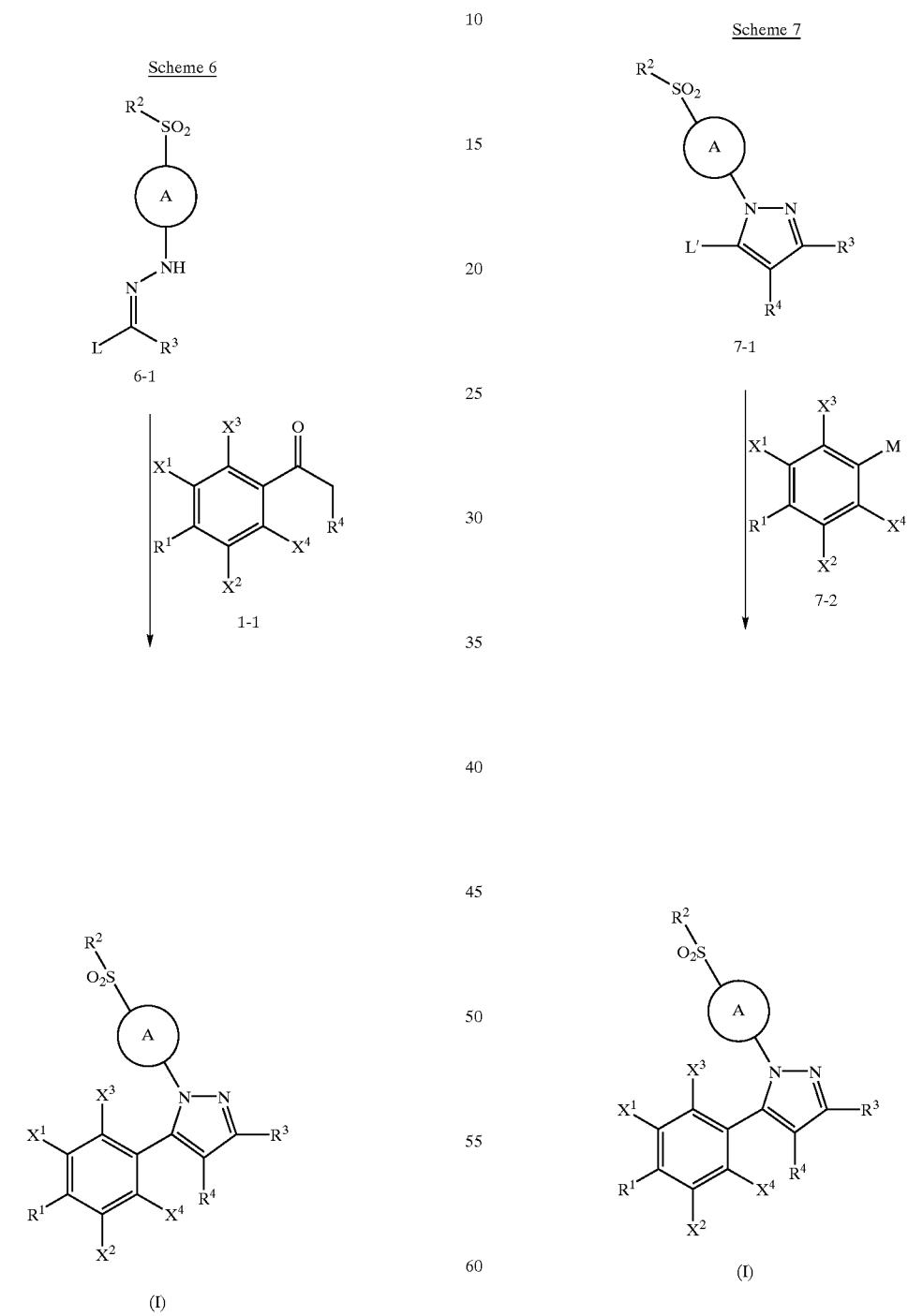
Scheme 6 illustrates another preparation methods of compounds of formula I (Heterocycles, 1990, 31, 1041).
Referring to Scheme 7, a compound of formula I may also be prepared by a coupling reaction of compound of formula 7-1 and a compound of formula 7-2 under similar conditions illustrated in Scheme 1 or 2.

Scheme 8

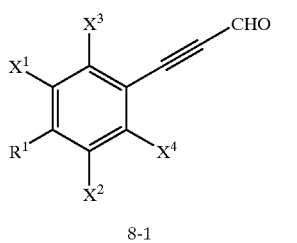

8-1

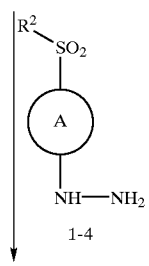

1-4

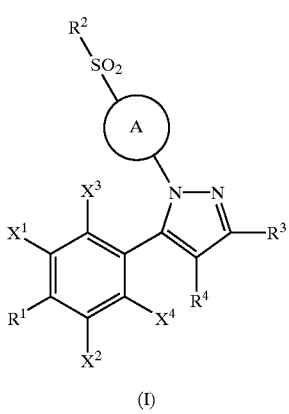

(I)

Formation of Hydrazine Compounds of Formula 4-1:

Scheme 9 illustrates preparation methods of hydrazine compounds formula 4-1 which can be used in the preparation process illustrated in Scheme 1.

Scheme 9

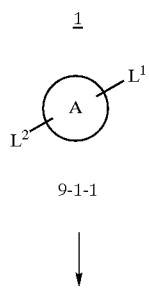

9-1-1

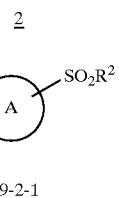

9-2-1

9-1-2

9-1-3

1-4

Route 1 (Thioalkylation and Oxidation):

As illustrated in Route 1, compounds of formula 1-4 can be prepared by subjecting a compound of the formula 9-1-1 wherein $L^1$ and $L^2$ are leaving groups to thioalkylation, oxidation and reaction with hydrazine or anhydrous hydrazine. Suitable leaving groups of the compounds used in this reaction are halo. In this process, compounds of the formula 1-4 are prepared from compounds of the formula 9-1-3 by reaction with hydrazine or anhydrous hydrazine in the presence of a polar solvent. Suitable solvents used in this reaction include alcohol, such as ethanol, methanol, propanol or butanol; dimethyl sulfoxide (DMSO), N,N-dimethylformamide (DMF), N,N-dimethylacetamide (DMA) or N-methyl-2-pyrrolidinone (MP), preferably an alcohol, most preferably ethanol. This reaction is generally carried out at a temperature from about 0° C. to about 140° C., preferably at about the reflux temperature of the polar solvent. Preferably the product is isolated as a salt, such as a hydrochloride salt. The reaction time ranges from about 1 hour to about 1 day. The compound of formula 9-1-3 is prepared from a compound of formula 9-1-2 by reaction with an oxidizing reagent in the presence of a solvent. Suitable oxidants include meta-chloroperbenzoic acid, hydrogen peroxide, sodium perborate, or Oxone® (Oxone® is preferred). Suitable solvents or solvent mixtures used in this reaction include methanol-water, dioxane-water, tetrahydrofuran-water, methylene chloride, or chloroform, preferably methanol-water. Suitable temperatures for the aforesaid reaction range from about 0° C. to about 60° C., preferably the temperature may range from about 20° C. to about 25° C. (i.e. room temperature). The reaction is complete within about 0.5 hours to about 24 hours, preferably about 16 hours. The compound of the formula 9-1-2 is prepared from a compound of formula 9-1-1 by nucleophilic substitution reaction using a sulfur nucleophilic reagent such as alkylthiol, dialkyldisulfide, sodium alkylsulfinate, sodium thioalkoxide or potassium Fthioalkoxide, in the presence or absence of a base in a polar solvent. Suitable bases used in this reaction include sodium hydroxide, triethylamine; alkyllithiums such as n-butyllithium, sec-butyllithium, and tert-butyllithium; and lithium diisopropylamide, and suitable solvents include ethers such as dimethylether; alkanols such as methanol, ethanol and tert-butanol; a mixture of an alkanol and water; THF; benzene; toluene; xylene; DMF; DMSO; dioxane; and 1,2-dimethoxyethane. This reaction is generally carried out at a temperature from about −78° C. to 200° C. for from about 1 minute to 3 days.

Route 2 (Hydrazine Formation):

Referring to Route 2, compound of the formula 1-4 may be prepared by reaction of a compound the formula 9-2-1 with a suitable reagent followed by reduction in an inert solvent or by catalytic hydrogenation. Typical reagents used in the first step include sodium nitrite in an aqueous medium (e.g., hydrochloric acid in water); nitrosyl chloride, nitrogen oxides and nitrile ethers. This reaction is typically carried out at about 0° C. for from about 1 minute to about 10 hours. Suitable reducing agents used in the subsequent reduction include zinc powder-acetic acid, metal halides such as $TiCl_3$ or $SnCl_2$, sodium-ethanol, sodium-aqueous ammonia, lithium aluminum hydride and the like. Catalytic hydrogenation may be carried out using a catalyst such as palladium on carbon (Pd/C), palladium on barium sulfate (Pd/BaSO$_4$), platinum on carbon (Pt/C), or tris(triphenylphosphine) rhodium chloride (Wilkinson's catalyst), in an appropriate solvent such as methanol, ethanol, THF, dioxane or ethyl acetate, at a pressure from about 1 to about 5 atmospheres and a temperature from about 10° C. to about 60° C. The following conditions are preferred: Pd on carbon, methanol at 25° C. and 50 psi of hydrogen gas pressure. This method also provides for introduction of hydrogen isotopes (i.e., deuterium, or tritium) by replacing $^1H_2$ with $^2H_2$ or $^3H_2$ in the above procedure. Compounds of formula 1-4 thus obtained may be isolated as an acid addition salt such as the hydrochloride salt. Compounds of formula 9-1-1 and 9-2-1 are commercially available or can be prepared by methods well known to those of ordinary skill in the art (e.g., F. Walker et al., J. Chem. Soc. 1939, 1948).

Triazine compounds of formula 1-4 can be prepared according to the methods illustrated in Scheme 10. In Scheme 10, triazine compounds of formula 1-4 are represented as compounds of formula 10-5.

Scheme 10

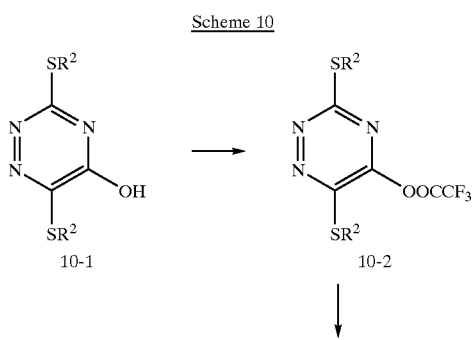

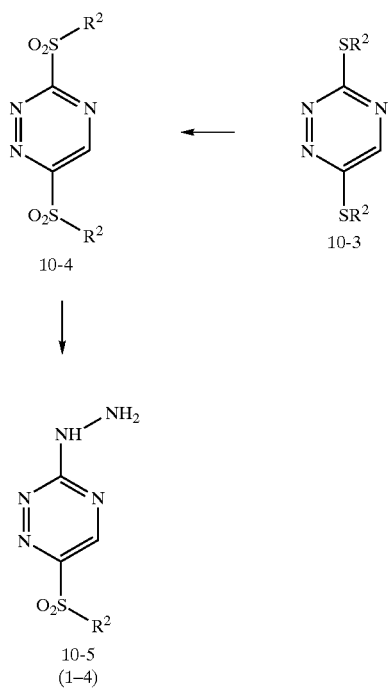

Scheme 10 illustrates preparation methods of compounds of formula 10-5 from compounds of formula 10-1 by substitution reaction with triflate to compounds of formula 10-2; reduction to compounds of formula 10-3; oxidation to compounds of formula 10-4; and substitution reaction with hydrazine. Substitution reaction of compounds of formula 10-1 with triflate can be carried out using trifle anhydride in the presence of pyridine. Reduction of compounds of formula 10-2 may be carried out using a suitable reducing reagent such as sodium borohydride or lithium aluminum hydride. Oxidation of compounds of formula 10-3 may be carried out by using mCPBA or Oxone as described in Scheme 5 and its discussion. Reaction with compounds of formula 10-4 and hydrazine can be carried out in an alcoholic solvent. Compounds of formula 10-5 thus obtained may be subjected to reactions with diketone compounds as illustrated in Scheme 1 using a acid catalyst such as sulfuric acid in 2,2,2-trifluoroethanol under reflux to yield compounds of formula I. In the process illustrated in Scheme 10, halogen can be also introduced to compounds of formula 10-2 instead of triflate under known conditions such as chlorination using phosphoryl oxychloride. Compounds of formula 10-1 may be prepared by known procedures described in literature such as J. Org. Chem., Vol. 63, p. 6329, 1998.

Scheme 11 illustrates preparation methods for synthesizing compounds of formula 11-3, which can be subjected to reactions illustrated in Scheme 9.

Scheme 11

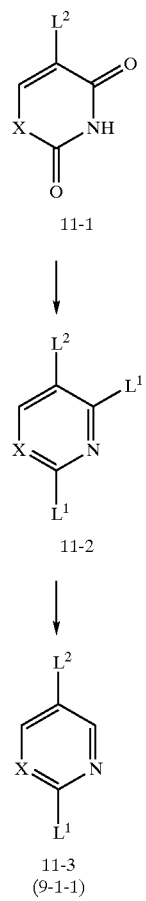

11-1

11-2

11-3
(9-1-1)

Referring to Scheme 11, a dicarbonyl compound of formula 11-1, wherein X is NH (i.e., pyrimidine compounds) or CH (i.e., pyridine compounds) and $L^2$ is a leaving group, may be subjected to substitution reaction to introduce $L^1$ to give the compound of formula 11-2 followed by reduction to give the compound of formula 11-3. Typical leaving groups $L^1$ and $L^2$ are halo, which can be introduced by halogenation according to methods known for those skilled in the art. For example, chlorination of a compound of formula 11-1 can be carried out using a chlorinating reagent such as an excess amount of phosphoryl chloride in the presence or absence of a base such as N,N-diethylaniline. This reaction can typically be carried out under reflux for from about 30 minutes to about 10 hours. The subsequent reduction of compounds of formula 11-2 may be carried out using a reducing reagent such as a metal catalyst in the presence of a base in a reaction inert solvent according to known methods in the art. For example, this reaction can typically be carried out using zinc powder in the presence of ammonia in a reaction inert solvent such as benzene at about room temperature for from about 1 hour to about 1 day. Then, compounds of formula 11-3 thus obtained can be subjected to the reactions illustrated in Scheme 9.

Scheme 12 illustrates the other hydrazine preparation methods.

Scheme 12

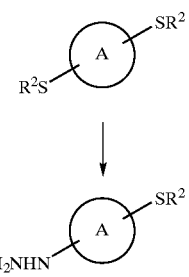

The starting materials in the aforementioned general syntheses may be obtained by conventional methods known to those skilled in the art. The preparation of such starting materials is described within the accompanying non-limiting examples which are provided for the purpose of illustration only. Alternatively, requisite starting materials may be obtained by analogous procedures, or modifications thereof, to those described hereinafter.

In each reaction described above, unless indicated otherwise, the reaction pressure is not critical. Generally, the reactions will be conducted at a pressure of about one to about three atmospheres, preferably at ambient pressure (about one atmosphere).

The starting materials in the aforementioned general syntheses may be obtained by conventional methods known to those skilled in the art. The preparation of such starting materials is described within the accompanying non-limiting examples which are provided for the purpose of illustration only. Alternatively, requisite starting materials may be obtained by analogous procedures, or modifications thereof, to those described hereinafter.

The products which are addressed in the aforementioned general syntheses and illustrated in the experimental examples described herein after may be isolated by standard methods and purification can be achieved by conventional means known to those skilled in the art, such as distillation, crystallization or chromatography techniques.

Certain compounds described herein contain one or more asymmetric centers and are capable of existing in various stereoisomeric forms. The present invention contemplates all such possible stereoisomers as well as their racemic and resolved, enantiomerically pure forms and pharmaceutically acceptable salts thereof.

In addition, when the compounds of this invention form hydrates or solvates they are also within the scope of this invention.

The compounds of the formula I which are basic in nature are capable of forming a wide variety of different salts with various inorganic and organic acids. Although such salts must be pharmaceutically acceptable for administration to animals, it is often desirable in practice to initially isolate a compound of the formula I from the reaction mixture as a pharmaceutically unacceptable salt and then simply convert the latter back to the free base compound by treatment with an alkaline reagent, and subsequently convert the free base to a pharmaceutically acceptable acid addition salt. The acid addition salts of the base compounds of this invention are readily prepared by treating the base compound with a substantially equivalent amount of the chosen mineral or organic acid in an aqueous solvent medium or in a suitable organic solvent such as methanol or ethanol. Upon careful evaporation of the solvent, the desired solid salt is obtained.

The acids which are used to prepare the pharmaceutically acceptable acid addition salts of the base compounds of this invention are those which form non-toxic acid addition salts, i.e., salts containing pharmacologically acceptable anions, such as hydrochloride, hydrobromide, hydroiodide, nitrate, sulfate or bisulfate, phosphate or acid phosphate, acetate, lactate, citrate or acid citrate, tartrate or bitartrate, succinate, maleate, fumarate, gluconate, saccharate, benzoate, methanesulfonate and pamoate [i.e., 1,1'-methylene-bis-(2-hydroxy-3-naphthoate)] salts.

Those compounds of the formula I which are also acidic in nature, e.g., where $R^3$ includes a COOH or tetrazole moiety, are capable of forming base salts with various pharmacologically acceptable cations. Examples of such salts include the alkali metal or alkaline-earth metal salts and particularly, the sodium and potassium salts. These salts are all prepared by conventional techniques. The chemical bases which are used as reagents to prepare the pharmaceutically acceptable base salts of this invention are those which form non-toxic base salts with the herein described acidic compounds of formula I. These non-toxic base salts include those derived from such pharmacologically acceptable cations as sodium, potassium, calcium and magnesium, etc. These salts can easily be prepared by treating the corresponding acidic compounds with an aqueous solution containing the desired pharmacologically acceptable cations, and then evaporating the resulting solution to dryness, preferably under reduced pressure. Alternatively, they may also be prepared by mixing lower alkanolic solutions of the acidic compounds and the desired alkali metal alkoxide together, and then evaporating the resulting solution to dryness in the same manner as before. In either case, stoichiometric quantities of reagents are preferably employed in order to ensure completeness of reaction and maximum product yields.

Also included within the scope of this invention are bioprecursors (also called pro-drugs) of the compounds of the formula I. A bioprecursor of a compound of the formula I is a chemical derivative thereof which is readily converted back into the parent compound of the formula I in biological systems. In particular, a bioprecursor of a compound of the formula I is converted back to the parent compound of the formula I after the bioprecursor has been administered to, and absorbed by, a mammalian subject, e.g., a human subject.

The subject invention also includes isotopically-labelled compounds, which are identical to those recited in formula I, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorus, fluorine and chlorine, such as $^2H$, $^3H$, $^{13}C$, $^{14}C$, $^{15}N$, $^{18}O$, $^{17}O$, $^{31}P$, $^{32}P$, $^{35}S$, $^{18}F$, and $^{36}Cl$, respectively. Compounds of the present invention, prodrugs thereof, and pharmaceutically acceptable salts of said compounds or of said prodrugs which contain the aforementioned isotopes and/or other isotopes of other atoms are within the scope of this invention. Certain isotopically-labelled compounds of the present invention, for example those into which radioactive isotopes such as $^3H$ and $^{14}C$ are incorporated, are useful in drug and/or substrate tissue distribution assay. Tritiated, i.e., $^3H$, and carbon-14, i.e., $^{14}C$, isotopes are particularly preferred for their ease of presentation and detectability. Further, substitution with heavier isotopes such as deutrium, i.e., $^2H$, can afford therapeutic advantage resulting from greater metabolic stability, for example increased in vivo half-life or reduced dosage requirement and, hence, may be preferred in some circumstances. Isotopically labelled compounds of formula I of this invention and prodrugs thereof can generally be prepared by carrying out the procedure disclosed in above-disclosed Schemes and/or Examples and Preparations below, by submitting a readily available isotopically labelled reagent for a non-isotopically labeled reagent.

The compounds of the formula I of this invention can be administered via either the oral, parenteral or topical routes to mammals. In general, these compounds are most desirably administered to humans in doses ranging from 0.01 mg to 100 mg per kg of body weight per day, although variations will necessarily occur depending upon the weight, sex and condition of the subject being treated, the disease state being treated and the particular route of administration chosen. However, a dosage level that is in the range of from 0.1 mg to 10 mg per kg of body weight per day, single or divided dosage is most desirably employed in humans for the treatment of abovementioned diseases.

These compounds are most desirably administered to said non-human mammals, e.g. dogs, cats, horses or livestock in an amount, expressed as mg per kg of body weight of said member per day, ranging from about 0.01 mg/kg to about 20.0 mg/kg/day, preferably from about 0.1 mg/kg to about 12.0 mg/kg/day, more preferably from about 0.5 mg/kg to about 10.0 mg/kg/day, and most preferably from about 0.5 mg/kg to about 8.0 mg/kg/day.

The compounds of the present invention may be administered alone or in combination with pharmaceutically acceptable carriers or diluents by either of the above routes previously indicated, and such administration can be carried out in single or multiple doses. More particularly, the novel therapeutic agents of the invention can be administered in a wide variety of different dosage forms, i.e., they may be combined with various pharmaceutically acceptable inert carriers in the form of tablets, capsules, lozenges, trochees, hard candies, powders, sprays, creams, salves, suppositories, jellies, gels, pastes, lotions, ointments, aqueous suspensions, injectable solutions, elixirs, syrups, and the like. Such carriers include solid diluents or fillers, sterile aqueous media and various nontoxic organic solvents, etc. Moreover, oral pharmaceutical compositions can be suitably sweetened and/or flavored. In general, the therapeutically-effective compounds of this invention are present in such dosage forms at concentration levels ranging 5% to 70% by weight, preferably 10% to 50% by weight.

For oral administration, tablets containing various excipients such as microcrystalline cellulose, sodium citrate, calcium carbonate, dipotassium phosphate and glycine may be employed along with various disintegrants such as starch and preferably corn, potato or tapioca starch, alginic acid and certain complex silicates, together with granulation binders like polyvinylpyrrolidone, sucrose, gelatin and acacia. Additionally, lubricating agents such as magnesium stearate, sodium lauryl sulfate and talc are often very useful for tabletting purposes. Solid compositions of a similar type may also be employed as fillers in gelatine capsules; preferred materials in this connection also include lactose or milk sugar as well as high molecular weight polyethylene grycols. When aqueous suspensions and/or elixirs are desired for oral administration, the active ingredient may be combined with various sweetening or flavoring agents, coloring matter or dyes, and, if so desired, emulsifying and/or suspending agents as well, together with such diluents as water, ethanol, propylene glycol, glycerin and various combinations thereof.

For parenteral administration, solutions of a compound of the present invention in either sesame or peanut oil or in aqueous propylene glycol may be employed. The aqueous solutions should be suitably buffered (preferably pH>8) if necessary and the liquid diluent first rendered isotonic. These aqueous solutions are suitable for intravenous injection purposes. The oily solutions are suitable for intra-articular, intramuscular and subcutaneous injection purposes. The preparation of all these solutions under sterile conditions is readily accomplished by standard pharmaceutical techniques well-known to those skilled in the art. Additionally, it is also possible to administer the compounds of the present invention topically when treating inflammatory conditions of the skin and this may preferably be done by way of creams, jellies, gels, pastes, ointments and the like, in accordance with standard pharmaceutical practice.

The compounds of formula I may also be administered in the form of suppositories for rectal or vaginal administration of the active ingredient. These compositions can be prepared by mixing the active ingredient with a suitable non-irritating excipient which is solid at room temperature (for example, 10° C. to 32° C.) but liquid at the rectal temperature and will melt in the rectum or vagina to release the active ingredient. Such materials are polyethylene glycols, cocoa butter, suppository and wax.

For buccal administration, the composition may take the form of tablets or lozenges formulated in conventional manner.

Combination With Other Drugs:

Compounds of formula I would be useful for, but not limited to, the treatment of inflammation in a subject, and for treatment of other inflammation-associated disorders, such as, as an analgesic in the treatment of pain and headaches, or as an antipyretic for the treatment of fever. For example, combinations of the invention would be useful to treat arthritis, including but not limited to rheumatoid arthritis, spondyloarthopathies, gouty arthritis, osteoarthritis, systemic lupus erythematosus and juvenile arthritis. Such combinations of the invention would be useful in the treatment of asthma, bronchitis, inmenstrual cramps, tendinitis, bursitis, and skin related conditions such as psoriasis, eczema, burns and dermatitis. Combinations of the invention also would be useful to treat gastrointestinal conditions such as inflammatory bowel disease. Crohn's disease, gastritis, irritable bowel syndrome and ulcerative colitis and for the prevention of colorectal cancer. Combinations of the invention would be useful in creating inflammation in such diseases as vascular diseases, migraine headaches, periarteritis nodosa, thyroiditis, aplastic anemia, Hodgkin's disease, sclerodoma, rheumatic fever, type I diabetes, myasthenia gravis, multiple sclercsis, sarcoidosis, nephrotic syndrome, Behcet's syndrome, polymyositis, gingivitis, hypersensitivity, Conjunctivitis, swelling occurring after injury, myocardial ischemia, and the like. The combinations would also be useful for the treatment of certain central nervous system disorders such as Alzheimer's disease and dimentia. The combinations of the invention are useful as anti-inflammatory agents, such as for the treatment of arthritis, with the additional benefit of having significantly less harmful side effects. These compositions would also be useful in the treatment of allergic rhinitis, respiratory distress syndrome, endotoxin shock syndrome, atherosclerosis and central nervous system damage resulting from stroke, ischemia and trauma.

Compounds of formula I will be useful as a partial or complete substitute for conventional NSAID's in preparations wherein they are presently co-administered with other agents or ingredients. Thus, the invention encompasses pharmaceutical compositions for treating COX-2 mediated diseases as defined above comprising a non-toxic therapeutically effective amount of the compound of formula I and one or more ingredients such as another pain reliever including acetaminophen or phenacetin; a potentiator including caffeine; an $H_2$-antagonist, aluminom or magnesium hydroxide, simethicone, a decongestant including phenylephrine, phenylproanolamine, psuedophedrine, oxymetazoline, ephinephrine, naphazoline, xylometazoline, propylhexedrine, or levodesoxyephedrine; an antiitussive including codeine, hydrocodone, caramiphen, carbetapentane, or dextramethorphan; a prostaglandin including misoprostol, enprostil, rioprostil, ornoprotol or rosaprostol; a diuretic; a sedating or non-sedating antihistamine; anticancer agents such as angiostatin and endostatin; anti-Alzheimers such as Doepezil and Tacrine hydrochloride; and TNF alpha inhibitors such as Etanercept.

These cyclooxygenase inhibitors can further be used in combination with nitric oxide inhibitors disclosed in WO 96/28145.

Also, the invention encompasses pharmaceutical compositions for treating COX-2 mediated diseases as defined above comprising a non-toxic therapeutically effective amount of the compound of formula I and one or more anti-ulcer agent and/or prostaglandins, which are disclosed in WO 97/11701.

The useful prostaglandins include misoprostol, plusminus methyl 11α, 16-dihydroxy-16-methyl-9-oxoprost 13E-en-1-oate; enisoprost and methyl-7-[2B-[6-(1-cyclopenten-1-yl)-4-hydroxy-4-methyl-1E, 5E-hexadienyl]-3cc-hydroxy-5-oxo 1R, 1α-cyclopentyl]-4Z-heptenoate. Prostaglandins within the scope of the invention also include arbaprostil, enprostil, rioprostol, nocloprost, mexiprostil, omoprostol, dimoxaprost, tiprostanide and rosaprostol.

The present compounds may also be used in co-therapies, partially or completely, in place of other conventional antiinflammatories, such as together with steroids, 5-lipoxygenase inhibitors, $LTB_4$ antagonists and $LTA_4$ hydrolase inhibitor's.

An example of LTB$_4$ is disclosed in WO97/29774. Suitable LTB$_4$ inhibitors include, among others, ebselen, Bayer Bay-x-1005, Ciba Geigy compound CGS-25019C, Leo Denmark compound ETH-615, Lilly compound LY-293111, Ono compound ONO-4057, Terumo compound TMK-688, Lilly compounds LY-213024, 264086 and 292728, Ono compound ONO-LB457, Searle compound SC-S3228, calcitrol, Lilly compounds LY-210073, LY223982, LY233469, and LY255283, Ono compound ONO-LB-448, Searle compounds SC-41930, SC-50605 and SC-51146, and SK&F compound SKF-104493. Preferably, the LTB$_4$ inhibitors are selected from ebselen, Bayer Bay-x-1005, Ciba Geigy compound CGS-25019C, Leo Denmark compound ETH-61S, Lilly compound LY-293111, Ono compound ONO-4057 and Terumo compound TMK-688.

An example of 5-LO inhibitors is disclosed in WO97/29776. Suitable 5-LO inhibitors include, among others, masoprocol, tenidap, zileuton, pranlukast, tepoxalin, rilopirox, flezelastine hydrochloride, enazadrem phosphate and bunaprolast.

An example of LTA$_4$ hydrolase inhibitors is disclosed in WO97/29774. Suitable LTA$_4$ hydrolase inhibitors include, among others, Rhone-Poulenc Rorer RP-64966.

The administration of the present invention may be for either prevention or treatment purposes. The methods and compositions used herein may be used alone or in conjunction with additional therapies known to those skilled in the art in the prevention or treatment of angiogenesis. Alternatively, the methods and compositions described herein may be used as adjunct therapy. By way of example, the cyclooxygenase-2 inhibitor may be administered alone or in conjunction with other antineoplastic agents or other growth inhibiting agents or other drugs or nutrients.

There are large numbers of antineoplastic agents available in commercial use, in clinical evaluation and in pre-clinical development, which could be selected for treatment of angiogenesis by combination drug chemotherapy. Such antineoplastic agents fall into several major categories, namely, antibiotic-type agents, alkylating agents, antimetabolite agents, hormonal agents, immunological agents, interferon-type agents and a category of miscellaneous agents. Alternatively, other anti-neoplalstic agents, such as metallomatrix proteases inhibitors (MMP), such as MMP-13 inhibitors including batiastat, marimastat. Agouron Pharmaceuticals AG-3340, and Roche RQ-32–3555, or alpha,beta, inhibitors may be used.

A first family of antineoplastic agents which may be used in combination with a selective cyclooxygenase-2 inhibitor consists of antimetabolite-type antineoplastic agents. Suitable antimetabolite antineoplastic agents may be selected from the group consisting of 5-FU-fibrinogen, acanthifolic acid, aminothiadiazole, brequinar sodium, carmofur, Ciba-Geigy CGP-30694, cyclopentyl cytosine, cytarabine phosphate stearate, cytarabine conjugates, Lilly DATHF, Merrel Dow DDFC, dezaguanine, dideoxycytidine, dideoxyguanosine, didox, Yoshitomi DMDC, doxifluridine, Wellcome EHNA, Merck & Co. EX-015, fazarabine, floxuridine, fludarabine phosphate, 5-fluorouracil, N-(2'-furanidyl)-5-fluorouracil, Daiichi Seiyaku FQ-152, isopropyl pyrrolizine, Lilly LY-188011, Lilly LY-264618, methobenzaprim, methotrexate, Wellcome MZPES, norspermidine, NCI NSC-127716, NCI NSC-264880, NCI NSC-39661, NCI NSC-612567, Warner-Lambert PALA, pentostatin, piritrexim, plicamycin, Asahi Chemical PL-AC, Takeda TAC-788, thioguanine, tiazofurin, Erbamont TIF, trimetrexate, tyrosine kinase inhibitors, tyrosine protein kinase inhibitors, Taiho UFT and uricytin.

A second family of antineoplastic agents which may be used in combination with a selective cyclooxygenase-2 inhibitor consists of alkylating-type antineoplastic agents. Suitable alkylating-type antineoplastic agents may be selected from the group consisting of Shionogi 254-S, aldo-phosphamide analogues, altretamine, anaxirone, Boehringer Mannheim BBR-2207, bestrabucil, budotitane, Wakunaga CA-102, carboplatin, carmustine, Chinoin-139, Chinoin-153, chlorambucil, cisplatin, cyclophosphamide, American Cyanamid CL-286558, Sanofi CY-233, cyplatate, Degussa D-19-384, Sumimoto DACHP(Myr)2, diphenylspiromustine, diplatinum cytostatic. Erba distamycin derivatives, Chugai DWA-2114R, ITI E09, elmustine, Erbamont FCE-24517, estramustine phosphate sodium, fotemustine, Unimed G-6-M, Chinoin GYKI-17230, hepsulfam, ifosfamide, iproplatin, lomustine, mafosfamide, mitolactol, Nippon Kayaku NK-121, NCI NSC-264395, NCI NSC-342215, oxaliplatin, Upjohn PCNU, prednimustine, Proter PTT-119, ranimustine, semustine, SmithKline SK&F-101772, Yakult Honsha SN-22, spiromus-tine, Tanabe Seiyaku TA-077, tauromustine, temozolomide, teroxirone, tetraplatin and trimelamol.

A third family of antineoplastic agents which may be used in combination with a selective cyclooxygenase-2 inhibitor consists of antibiotic-type antineoplastic agents. Suitable antibiotic-type antineoplastic agents may be selected from the group consisting of Taiho 4181-A, aclarubicin, actinomycin D, actinoplanone, Erbamont ADR-456, aeroplysinin derivative, Ajinomoto AN-201-II. Ajinomoto AN-3, Nippon Soda anisomycins, anthracycline, azino-mycin-A, bisucaberin, Bristol-Myers BL-6859, Bristol-Myers BMY-25067. Bristol-Myers BMY-25551, Bristol-Myers BMY-26605, Bristol-Myers BMY-27557, Bristol-Myers BMY-28438, bleomycin sulfate, bryostatin-1, Taiho C-1027, calichemycin, chromoximycin, dactinomycin, daunorubicin, Kyowa Hakko DC-102, Kyowa Hakko DC-79, Kyowa Hakko DC-88A, Kyowa Hakko DC89-A1, Kyowa Hakko DC92-B, ditrisarubicin B, Shionogi DOB-41, doxorubicin, doxorubicin-fibrinogen, elsamicin-A, epirubicin, erbstatin, esorubicin, esperamicin-A1, esperamicin-A1b. Erbamont FCE-21954, Fujisawa FK-973, fostriecin, Fujisawa FR-900482, glidobactin, gregatin-A, grincamycin, herbimycin, idarubicin, illudins, kazusamycin, kesarirhodins, Kyowa Hakko KM-5539, Kirin Brewery KRN-8602, Kyowa Hakko KT-5432, Kyowa Hakko KT-5594, Kyowa Hakko KT-6149, American Cyanamid LL-D49194, Meiji Seika ME 2303, menogaril, mitomycin, mitoxantrone, SmithKline M-TAG, neoenactin, Nippon Kayaku NK-313, Nippon Kayaku NKT-OI, SRI International NSC-357704, oxalysine, oxaunomycin, peplomycin, pilatin, pirarubicin, porothramycin, pyrindamycin A, Tobishi RA-I, rapamycin, rhizoxin, rodorubicin, sibanomicin, siwenmycin, Sumitomo SM-5887, Snow Brand SN-706, Snow Brand SN-07, sorangicin-A, sparsomycin, SS Pharmaceutical SS-21020, SS Pharmaceutical SS-7313B, SS Pharmaceutical SS-9816B, steffimycin B, Taiho 4181-2, talisomycin, Takeda TAN-868A, terpentecin, thrazine, tricrozarin A, Upjohn U-73975, Kyowa Hakko UCN-10028A, Fujisawa WF-3405, Yoshitomi Y-2S024 and zorubicin.

A fourth family of antineoplastic agents which may be used in combination with the selective cyclooxygenase-2 inhibitor consists of a miscellaneous family of antineoplastic agents selected from the group consisting of alpha-carotene, alpha-difluoromethyl-arginine, acitretin, Biotec AD-5, Kyorin AHC-52, alstonine, amonafide, amphethinile. amsacrine, Angiostat, ankinomycin, anti-neoplaston AIO, antineoplaston A2, antineoplaston A3, antineoplaston A5, antineoplaston AS2-1, Henkel APD, aphidicolin glycinate, asparaginase, Avarol, baccharin, batracylin, benfluron, benzotript, Ipsen-Beaufour BIM-23015, bisantrene, Bristo-Myers BMY-40481, Vestar boron-1O, bromofosfamide, Wellcome BW-502, Wellcome BW-773, caracemide, carmethizole hydrochloride, Ajinomoto CDAF, chlorsulfaquinoxalone, Chemes CHX-2053, Chemex CHX-1OO, Warner-Lambert CI-921, Warner-Lambert CI-937, Warner-Lambert CI-941, Warner-Lambert CI-958, clanfenur, claviridenone, ICN compound 1259, ICN compound 4711, Contracan, Yakult Honsha CPT-11, crisnatol, curaderm, cytochalasin B, cytarabine, cytocytin, Merz D-609, DABIS maleate, dacarbazine, datelliptinium, didemnin-B, dihaematoporphyrin ether, dihydrolenperone, dinaline, distamycin, Toyo Pharmar DM-341, Toyo Pharmar DM-75, Daiichi Seiyaku DN-9693, elliprabin, elliptinium acetate, Tsumura EPMTC, ergotamine, etoposide, etretinate, fenretinide, Fujisawa FR-57704, gallium nitrate, genkwadaphnin, Chugai GLA-43, Glaxo GR-63178, grifolan NMF-5N, hexadecylphosphocholine, Green Cross H0-221, homoharringtonine, hydroxyurea, BTG ICRF-187, ilmofosine, isoglutamine, isotretinoin. Otsuka JI-36, Ramot K-477, Otsuak K-76COONa, Kureha Chemical K-AM, MECT Corp KI-8110, American Cyanamid L-623, leukoregulin, lonidamine, Lundbeck LU-23-112, Lilly LY-186641, NCI (US) MAP, marycin, Merrel Dow MDL-27048, Medco MEDR-340, merbarone, merocyanine derivatives, methylanilinoacridine, Molecular Genetics MGI-136, minactivin, mitonafide, mitoquidone, mopidamol, motretinide, Zenyaku Kogyo MST-16, N-(retinoyl)amino acids, Nisshin Flour Milling N-021, N-acylated-dehydroalanines, nafazatrom, Taisho NCU-190, nocodazole derivative, Normosang, NCI NSC-145813, NCI NSC-361456, NCI NSC-604782, NCI NSC-95580, octreotide, Ono ONO-112, oquizanocine, Akzo Org-10172, pancratistatin, pazelliptine, Warner-Lambert PD-111707, Warner-Lambert PD-115934, Warner-Lambert PD-131141, Pierre Fabre PE-1OO1, ICRT peptide D, piroxantrone, polyhaematoporphyrin, polypreic acid, Efamol porphyrin, probimane, procarbazine, proglumide, Invitron protease nexin I, Tobishi RA-700, razoxane, Sapporo Breweries RBS, restrictin-P, retelliptine, retinoic acid, Rhone-Poulenc RP-49532, Rhone-Poulenc RP-56976, SmithKline SK&F-104864, Sumitomo SM-108, Kuraray SMANCS, SeaPharm SP-10094, spatol, spirocyclopropane derivatives, spirogermanium, Unimed, SS Pharmaceutical SS-554, strypoldinone, Stypoldione, Suntory SUN 0237, Suntory SUN 2071, superoxide dismutase, Toyama T-506, Toyama T-680, taxol, Teijin TEI-0303, teniposide, thaliblastine, Eastman Kodak TJB-29, tocotrienol, Topostin, Teijin TT-82, kyowa Hakko UCN-O1, Kyowa Hakko UCN-1028, ukrain, Eastman Kodak USB-006, vinblastine sulfate, vincristine, vindesine, vinestramide, vinorelbine, vintriptol, vinzolidine, withanolides and Yamanouchi YM-534.

Examples of radioprotective agents which may be used in the combination chemotherapy of this invention are AD-5, adchnon, amifostine analogues, detox, dimesna, 1-102, MN-159, N-acylated-dehydroalanines, TGF-Genentech, tiprotimod, amifostine, WR-151327, FUT-187, ketoprofen transdermal, nabumetone, superoxide dismutase (Chiron) and superoxide disrrtutase Enzon.

Methods for preparation of the antineoplastic agents described above may be found in the literature. Methods for preparation of doxorubicin, for example, are described in U.S. Pat. No. 3,590,028 and U.S. Pat. No. 4,012,448. Methods for preparing metallomatrix protease inhibitors are described in EP 780386, WO97/20824. WO96/15096. Methods for preparing SOD mimics are described in EP 524,101. Methods for preparing alpha,beta, inhibitors are described in W097/08174.

In addition, the selective COX-2 inhibitor may be administered in conjunction with other antiinflammatory agents for maximum safety and efficacy, including NSAID's, selective COX-1 inhibitors and inhibitors of the leukotriene pathway, including 5-lipoxygenase inhibitors. Examples of NSAID's include indomethacin, naproxen, ibruprofen, salicylic acid derivatives such as aspirin, diclofenac, ketorolac, piroxicam, meloxicam, mefenamic acid, sulindac, tolmetin sodium, zomepirac, fenoprofen, phenylbutazone, oxyphenbutazone, nimesulide, zaltoprofen and letodolac.

Methods of Assessing Biological Activities:

Activities of the compounds of the formula I of the present invention may be demonstrated by the following assays.

In vitro Assays:

Human Cell Based COX-1 Assay:

Human peripheral blood obtained from health volunteers is diluted to 1/10 volume with 3.8% sodium citrate solution. The platelet-rich plasma immediately obtained is washed with 0.14M sodium chloride solution containing 12 mM Tris-HCl (pH 7.4) and 1.2 mM EDTA. Platelets are then washed with platelet buffer (Hanks buffer (calcium free) containing 0.2% BSA and 20 mM Hepes buffer). Finally, the human washed platelets (HWP) are suspended in platelet buffer at the concentration of $2.85 \times 10^8$ cells/ml and stored at room temperature until used. The HWP suspension (70 $\mu$l aliquots, final $2.0 \times 10^7$ cells/ml) is placed in a 96-well U bottom plate and 10 $\mu$l aliquots of 12.6 mM $CaCl_2$ is added. Platelets are incubated with A23187 (final 10 $\mu$M, Sigma) with a test compound (0.1–100 $\mu$M) dissolved in DMSO (final concentration; less than 0.01%) at 37° C. for 15 minutes. The reaction is quenched by adding EDTA (final 7.7 mM), and TxB2 in the supernatant quantitated by using a radioimmunoassay kit (supplied by Amersham) according to the manufacture's procedure.

Human Cell Based COX-2 Assay:

The human sell based COX-2 assay is carried as previously reported by Moore et al., *Inflam. Res.*, Vol. 45, pp. 54-, 1996. Confluent human umbilical vein endothelial cells (HUVECs, Morinaga) in a 96-well U bottom plate are washed with 100 μl of RPMI1640 containing 2% FCS and incubation with hIL-1β (final concentration 300 U/ml, R & D Systems) at 37° C. for 24 hours. After washing, the activated HUVECs are stimulated with A23187 (final concentration 30 μM) in Hanks buffer containing 0.2% BSA, 20 mM Hepes and a test compound (0.1 nM–100 μM) dissolved in DMSSO (final concentration; less than 0.01%) 37° C. for 15 minutes. 6-Keto-PGF$_{1\alpha}$, stable metabolite of PGI$_2$, in the supernatant is quantitated after adequate dilution by using a radioimmunoassay kit (supplied by Amersham) according to the manufacture's procedures.

Canine In Vitro Assays

The following canine cell based COX 1 and COX-2 assays have been reported in Ricketts et al., Evaluation of Selective Inhibition of Canine Cyclooxygenase 1 and 2 by Carprofen and Other Nonsteroidal Anti-inflammatory Drugs, American Journal of Veterinary Research, 59 (11), 1441–1446.

Protocol for Evaluation of Canine COX-1 Activity

Test drug compounds were solubilized and diluted the day before the assay was to be conducted with 0.1 mL of DMSO/9.9 mL of Hank's balanced salts solution (HBSS), and stored overnight at 4° C. On the day that the assay was carried out, citrated blood was drawn from a donor dog, centrifuged at 190×g for 25 min at room temperature, and the resulting platelet-rich plasma was then transferred to a new tube for further procedures. The platelets were washed by centrifuging at 1500×g for 10 min at room temperature. The platelets were washed with platelet buffer comprising Hank's buffer (Ca free) with 0.2% bovine serum albumin (BSA) and 20 mM HEPES. The platelet samples were then adjusted to $1.5 \times 10^7$/mL, after which 50 μl of calcium ionophore (A23187) together with a calcium chloride solution were added to 50 μl of test drug compound dilution in plates to produce final concentrations of 1.7 μM A23187 and 1.26 mM Ca. Then, 100 μl of canine washed platelets were added and the samples were incubated at 37° C. for 15 min, after which the reaction was stopped by adding 20 μl of 77 mM EDTA. The plates were then centrifuged at 2000×g for 10 min at 4° C., after which 50 μl of supernatant was assayed for thromboxane B$_2$ (TXB$_2$) by enzyme-immunoassay (EIA). The pg/mL of TXB$_2$ was calculated from the standard line included on each plate, from which it was possible to calculate the percent inhibition of COX-1 and the IC$_{50}$ values for the test drug compounds.

Protocol for Evaluation of Canine COX-2 Activity

A canine histiocytoma (macrophage-like) cell line from the American Type Culture Collection designated as DH82, was used in setting up the protocol for evaluating the COX-2 inhibition activity of various test drug compounds. There was added to flasks of these cells 10 μg/mL of LPS, after which the flask cultures were incubated overnight. The same test drug compound dilutions as described above for the COX-1 protocol were used for the COX-2 assay and were prepared the day before the assay was carried out. The cells were harvested from the culture flasks by scraping, and were then washed with minimal Eagle's media (MEM) combined with 1% fetal bovine serum, centrifuged at 1500 rpm for 2 min, and adjusted to a concentration of $3.2 \times 10^5$ cells/mL. To 50 μl of test drug dilution there was added 50 μl of arachidonic acid in MEM to give a 10 μM final concentration, and there was added as well 100 μl of cell suspension to give a final concentration of $1.6 \times 10^5$ cells/mL. The test sample suspensions were incubated for 1 hr and then centrifuged at 1000 rpm for 10 min at 4° C., after which 50 μl aliquots of each test drug sample were delivered to EIA plates. The EIA was performed for prostaglandin E$_2$ (PGE$_2$), and the pg/mL concentration of PGE$_2$ was calculated from the standard line included on each plate. From this data it was possible to calculate the percent inhibition of COX-2 and the IC$_{50}$ values for the test drug compounds. Repeated investigations of COX-1 and COX-2 inhibition were conducted over the course of several months. The results are averaged, and a single COX-1:COX-2 ratio is calculated.

Whole blood assays for COX-1 and COX-2 are known in the art such as the methods described in C. Brideau, et al., A Human Whole Blood Assay for Clinical Evaluation of Biochemical Efficacy of Cyclooxygenase Inhibitors, Inflammation Research, 45, 68–74, (1996). These methods may be applied with feline, canine or human blood as needed.

In Vivo Assays:

Canine Whole Blood ex Vivo Determinations of COX-1 and COX-2 Activity Inhibition The in vivo inhibitory potency of a test compound against COX-1 and COX-2 activity may be evaluated using an ex vivo procedure on canine whole blood. Three dogs were dosed with 5 mg/kg of the test compound administered by oral gavage in 0.5% methylcellulose vehicle and three dogs were untreated. A zero-hour blood sample was collected from all dogs in the study prior to dosing, followed by 2- and 8-hour post-dose blood sample collections. Test tubes were prepared containing 2 μL of either (A) calcium ionophore A23187 giving a 50 μM final concentration, which stimulates the production of thromboxane B$_2$ (TXB$_2$) for COX-1 activity determination; or of (B) lipopolysaccharide (LPS) to give a 10 μg/mL final concentration, which stimulates the production of prostaglandin E$_2$ (PGE$_2$) for COX-2 activity determination. Test tubes with unstimulated vehicle were used as controls. A 500 μL sample of blood was added to each of the above-described test tubes, after which they were incubated at 37° C. for one hr in the case of the calcium ionophore-containing test tubes, and overnight in the case of the LPS-containing test tubes. After incubation, 10 μL of EDTA was added to give a final concentration of 0.3%, in order to prevent coagulation of the plasma which sometimes occurs after thawing frozen plasma samples. The incubated samples were centrifuged at 4° C. and the resulting plasma sample of ~200 μL was collected and stored at −20° C. in polypropylene 96-well plates. In order to determine endpoints for this study, enzyme immunoassay (EIA) kits available from Cayman were used to measure production of TXB$_2$ and PGE$_2$, utilizing the principle of competitive binding of tracer to antibody and endpoint determination by colorimetry. Plasma samples were diluted to approximate the range of standard amounts which would be supplied in a diagnostic or research tools kit, i.e., 1/500 for TXB$_2$ and 1/750 for PGE$_2$.

The data set out in Table 2 below show how the percent inhibition of COX-1 and COX-2 activity is calculated based on their zero hour values. The data is expressed as treatment group averages in pg/ml of TXB$_2$ and PGE$_2$ produced per sample. Plasma dilution was not factored in said data values.

The data in Table 2 show that, in this illustration, at the 5 mg/kg dose there was significant COX-2 inhibition at both timepoints. The data in Table 2 also show that at the 5 mg/kg dose there was no significant inhibition of COX-1 activity at the timepoints involved. Accordingly, the data in Table 2 clearly demonstrates that at the 5 mg/kg dosage concentration this compound possesses good COX-2 selectivity.

TABLE 2

| COX-1 ACTIVITY INHIBITION — Group Averages | | | | |
|---|---|---|---|---|
| | $TXB_2$ Pg/mL/Well | | Percent Inhibition | |
| Hour | 0-hour | 2-hour | 8-hour | 2-hour | 8-hour |
| Untreated | 46 | 45 | 140 | 2% | 0% |
| 5 mg/kg | 41 | 38 | 104 | 7% | 0% |

| COX-2 ACTIVITY INHIBITION — Group Averages | | | | |
|---|---|---|---|---|
| | $PGE_2$ Pg/mL/Well | | Percent Inhibition | |
| Hour | 0-hour | 2-hour | 8-hour | 2-hour | 8-hour |
| Untreated | 420 | 486 | 501 | 0% | 0% |
| 5 mg/kg | 711 | 165 | 350 | 77% | 51% |

COX inhibition is observed when the measured percent inhibition is greater than that measured for untreated controls. The percent inhibition in the above table is calculated in a straightforward manner in accordance with the following equation:

$$(PGE_2 \text{ at } t=0)-(PGE_2 \text{ at } t=2)\% \text{ Inhibition (2-hour)}=(PGE_2 \text{ at } t=0)$$

Carrageenan Induced Foot Edema in Rats

Male Sprague-Dawley rats (5 weeks old, Charles River Japan) are fasted overnight. A line is drawn using a marker above the ankle on the right hind paw and the paw volume (V0) is measured by water displacement using a plethysmometer (Murromachi). Animals are given orally either vehicle (0.1% methyl cellulose or 5% Tween 80) or a test compound (2.5 ml per 100 g body weight). One hour later, the animals are then injected intradermally with λ-carrageenan (0.1 ml of 1% w/v suspension in saline, Zushikagaku) into right hind paw (Winter et al., *Proc. Soc. Exp. Biol. Med.*, Vol. 111, p. 544-, 1962; Lombaridino et al., Arzneim. Forsch., Vol. 25, p. 1629-, 1975) and three hours later, the paw volume (V3) is measured and the increase in volume (V3-V0) calculated. Since maximum inhibition attainable with classical NSAIDs is 60–70%, $ED_{30}$ values are calculated.

Gastric Ulceration in Rats

The gastric ulcerogenicity of a test compound is assessed by a modification of the conventional method (Ezer et al.,*J. Pharm. Pharmacol.*, Vol. 28, p. 655-, 1976; Cashin et al, *J. Pharm. Pharmacol.*, Vol. 29, pp. 330–336, 1977). Male Sprague-Dawley rats (5 weeks old, Chales River Japan), fated overnight, were given orally either vehicle (0.1% methyl cellulose or 5% Tween 80) or a test compound (1 ml per 100 g body weight). Six hours after, the animals are sacrificed by cervical dislocation. The stomachs are removed, inflated with 1% formalin solution (10 ml), opened by cutting along the grater curvature. From the number of rats that show at least gastric ulcer or haemorrhaging erosion (including ecchymosis), the incidence ulceration is calculated. Animals do not have access to either food or water during the experiment.

Data Analysis:

Statistical program packages, SYSTANT (SYSTANT, INC.) and StatView (Abacus Cencepts, Inc.) for Macintosh are used. Difference between test compound treated groups and control group are tested for using ANOVA. The $IC_{50}$ ($ED_{30}$) values are calculated from the equation for the log-linear regression of concentration (dose) versus percent inhibition.

Most compounds prepared in the Working Examples as described hereinafter were tested by at least one of the methods described above, and showed $IC_{50}$ values of 0.001 $\mu M$ to 3 $\mu M$ with respect to inhibition of COX-2 in either the canine or human assays.

The following examples contain detailed descriptions of the methods of the preparation of compounds of formula I. These detailed descriptions fall within the scope of the invention and serve to exemplify the above described general synthetic procedures which form part of the invention. These detailed descriptions are presented for illustrative purposes only and are not intended to restrict the scope of the present invention.

EXAMPLES AND PREPARATIONS

The invention is illustrated in the following non-limiting examples in which, unless stated otherwise: all operations were carried out at room or ambient temperature, that is, in the range of 18–25° C.; evaporation of solvent was carried out using a rotary evaporator under reduced pressure with a bath of up to 60° C.; reactions were monitored by thin layer chromatography (tic) and reaction times are given for illustration only; melting points (m.p.) given are uncorrected (polymorphism may result in different melting points); structure and purity of all isolated compounds were assured by at least one of the following techniques: tlc (Merck silica gel 60 F-254 precoated plates), mass spectrometry, nuclear magnetic resonance (NMR) or infrared spectroscopy (IR). IR data were obtained on a FTIR 8200 (SHIMAZU Spectrometer). Yields are given for illustrative purposes only. Flash column chromatography was carried out using Merck silica gel 60 (230–400 mesh ASTM). Low-resolution mass spectral data (EI) were obtained on a Automass 120 (JEOL) mass spectrometer. Liquid Chromatography data was collected on a Hewlett Packard 1100 Liquid Chromatography/Mass Selective Detector (LC/MSD). Analysis was performed on a Luna C-18 column with dimensions of 3.0×150 mm. The flow rate was 0.425 ml/min running a gradient of 50% 0.1% aqueous formic acid and 50% acetonitrile to 100% acetonitrile in 15 minutes. The ionization type for the mass detector of the Mass Spectrophotometer was atmospheric pressure electrospray in the positive ion mode with a fragmentor voltage of 50 volts. NMR data was determined at 270 MHz (JEOL JNM-LA 270 spectrometer) using deuterated chloroform (99.8% D), methanol (99.8% D) or dimethylsulfoxide (99.9% D) as solvent unless indicated otherwise, relative to tetramethylsilane (TMS) as internal standard in parts per million (ppm); conventional abbreviations used are: s=singlet, d=doublet, t=triplet, q=quartet, m=multiplet, br=broad, etc.

The following abbrevation are used:

| | |
|---|---|
| THF: | tetrahydrofuran |
| $CH_2Cl_2$: | dichloromethane |
| $NaHCO_3$: | sodium bicarbonate |
| HCl: | hydrogen chloride |
| $MgSO_4$: | magnesium sulfate |
| $Na_2SO_4$: | sodium sulfate |
| DME: | dimethoxyethane |
| n-BuLi: | n-butyllithium |
| DMF: | dimethylformamide |

Example 1

6-[5-[4-(2-Furyl)phenyl]-3-(trifluoromethyl)-1H-pyrazol-1-yl]-3-pyrdinesulfonamide 6-Hydrazino-3-pyridinesulfonamide Dihydrochloride. (Step 1)

To a solution of 6-chloro-3-pyridinesulfonamide (0.64 g, 3.32 mmol) in ethanol (20 mL) was added hydrazine anhydrous (0.128 g, 3.99 mmol). After the reaction mixture was heated at reflux temperature for 5 hours, the solvent was removed. The residue was washed with methylene chloride to give the subtitle compound (0.494 g, 79.0% yield).

$^1$H-NMR (DMSO-$d_6$) δ: 8.33 (d, J=2 Hz, 1H), 8.26 (brs, 1H), 7.75 (dd, J=2, 9 Hz, 1H), 7.12–7.07 (brs, 2H), 6.76 (d, J=9 Hz, 1H), 4.34 (brs, 2H).

The solid (0.49 g, 2.6 mmol) was dissolved in 10% methanolic HCl (3 mL), and volatiles were removed by evaporation. The residue was recrystallized from methylene chloride-ether to give the subtitle compound (0.574 g, 84.5% yield)

4,4,4-Trifluoro-1-[4-(2-furyl)phenyl]butane-1,3-dione. (Step 2)

To a stirred solution of 4,4,4-trifluoro-1-(4-bromophenyl)butane-1,3-dione (1 g, 3.39 mmol, *J.Med.Chem.*, 1997, 40, 1347) in DME.(40 mL) was added furan-2-boronic acid (0.455 g, 4.07 mmol), bis(triphenylphosphine) palladium(.) chloride (0.271 g, 0.386 mmol) and saturated NaHCO3 solution (12 mL) at room temperature under nitrogen. The mixture was heated at reflux temperature for 5 hours, and cooled down to room temperature. The reaction mixture was filtered through celite, the filtrate was poured into water and the whole was extracted with ethyl acetate (30 mL×3). The organic layer was washed with brine, dried over sodium sulfate, and concentrated in vacuo. The residue was purified by flash chromatography eluting with hexane/ethyl acetate (3/1) to give the subtitle compound (0.586 g, 61.2% yield). MS (EI): m/z 282 (M$^+$).

[5-[4-(2-Furyl)phenyl]-1-[2-(5-sulfamoyl)pyridyl]-3-trifluoromethyl-1H-pyrazole. (Step 3)

A mixture of 4,4,4-trifluoro-1-[4-(2-furyl)phenyl]butane-1,3-dione (0.282 g, 1 mmol) and 6-hydrazino-3-pyridinesulfonamide dihydrochloride (0.287 g, 1.1 mmol) in ethanol (10 mL) was heated at reflux temperature for 18 hours. The reaction mixture was cooled and the solvent removed under reduced pressure. The residue was redissolved in ethyl acetate (30 mL) and washed with saturated aqueous NaHCO3 (20 mL), brine. The organic layer was dried over sodium sulfate, and concentrated in vacuo. The residue was purified by flash chromatography on silica eluting with hexane/ethyl acetate (3/1). The resulting solid was recrystallized from dichloromethane/hexane to give the title compound (0.05 g, 11.5% yield).

mp: 157.2° C. $^1$H-NMR (CDCl$_3$) δ: 8.79 (d, J=2 Hz, 1H), 8.31 (dd, J=3, 9 Hz, 1H), 7.91 (d, J=9 Hz, 1H), 7.68 (d, J=8 Hz, 2H), 7.51 (d, J=2 Hz, 2H), 7.30 (d, J=8 Hz, 2H), 6.79 (s, 1H), 6.73 (d, J=4 Hz, 1H), 6.51 (dd, J=2, 4 Hz, 1H), 5.00 (brs, 2H). Anal.Calcd.for.$C_{19}H_{13}F_3N_4O_3S$, 0.2H$_2$O: C, 52.10; H, 3.08; N, 12.79. Found: C, 52.01; H, 3.19; N, 12.44. MS (EI): m/z 434 (M$^+$).

Example 2

5-[5-[4-(2-Furyl)phenyl]-3-(trifluoromethyl)-1H-pyrazol-1-yl]-2-pyridinesulfonamide 5-Hydrazino-2-pyridinesulfonamide Hydrochloride (Step 1)

To a suspension of 5-amino-2-pyridinesulfonamide (7.0 g, 0.040 mol, C. Komfeld, *J. Amer. Chem. Soc.* 1695 (1942)) in conc HCl (60 mL) and H$_2$O (20 mL), sodium nitrite (3.6 g, 0.052 mol) in H$_2$O (50 mL) was added dropwise at 0° C. and the mixture was stirred for 30 min. The mixture changed to yellow brown solution and tin(II) chloride dihydrate (36 g, 0.16 mol) in conc HCl (30 mL) was added dropwise below 5° C. and stirred for 1 hour at 0° C. The mixture was made basic by addition of aqueous NaOH (pH=8). The resultant suspension was added THF (400 mL) and stirred for 10 min. The white precipitate was separated by celite filtration and washed with THF (100 mL×3). The filtrate was separated in two phase and organic phase was separated. Water phase was extracted with THF (150 mL×2), dried (MgSO$_4$), and concentrated in vacuo gave brown oil. The oil was disolved in 10% HCl-MeOH (50 mL) and concentrated in vacuo gave brown amorphous solid. Crystallization from CH$_2$Cl$_2$ gave the titled compound as a brown solid (5.0 g, 56%).

$^1$H-NMR (DMSO-$d_6$) δ: 10.74 (br s, 2H), 8.35 (d, J=2.3 Hz, 1H), 7.82 (d, J=8.6 Hz, 1H), 7.49 (dd, J=2.3, 8.6 Hz, 1H), 7.30 (br s, 1H).

5-[5-[4-(2-Furyl)phenyl]-3-(trifluoromethyl)-1H-pyrazol-1-yl]-2-pyridinesulfonamide (Step 2)

The title compound was prepared according to the procedure of Example 1 (step 2) using 5-hydrazino-2-pyridinesulfonamide hydrochloride instead of 2-hydrazino-5-pyridine sulfonamide dihydrochloride.

mp: 140–170° C. $^1$H-NMR (CDCl$_3$) δ: 8.69 (d, J=2.3 Hz, 1H), 8.02 (d, J=8.6 Hz, 1H), 7.90 (dd, J=2.3, 8.6 Hz, 1H), 7.70 (d, J=8.2 Hz, 2H), 7.51 (d, J=1.6 Hz, 1H), 7.25 (d, J=8.2 Hz, 2H), 6.84 (s, 1H), 6.75 (d, J=3.5 Hz, 1H), 6.51 (dd, J=2.0, 3.5 Hz, 1H), 5.07 (br 2H). Anal. Calcd. for $C_{19}H_{13}N_4O_3F_3S$: C, 52.53; H, 3.02; N, 12.90. Found: C, 52.43; H, 3.03; N, 12.66.

Example 3

5-[5-[3-Chloro-4-(1,3-oxazol-2-yl)phenyl]-3-(trifluoromethyl)-1H-pyrazol-1-yl]-2-pyridinesulfonamide 4-Bromo-2-chloro-N-(2,2-diethoxyethyl)benzamide (Step 1).

To a suspension of 2-chloro-4-bromobenzoic acid (10.0 g, 42.47 mmol) in CH2Cl2 (1000 mL) was added aminoacetaldehyde diethyl acetal (5.1 mL, 46.72 mmol) and WSC (9.77 g, 50.96 mmol) at room temperature, and stirred for 4 hours. The mixture was washed with water (100 mL), dried over MgSO$_4$. Removal of the solvent, gave title compound (14.88 g, 100% yield).

$^1$H-NMR (CDCl$_3$) δ 7.56–7.59 (m, 2H), 7.47 (dd, J=1.8, 8.2 Hz, 2H), 6.51 (br s, 1H), 4.64 (t, J=5.4 Hz, 1H), 3.53–3.80 (m, 6H), 1.23 (t, J=6.9 Hz, 3H).

4-Bromo-2-chloro-N-(2-oxoethyl)benzamide (Step 2).

To a solution of 4-bromo-2-chloro-N-(2,2-diethoxyethyl) benzamide (14.88 g, 42.44 mmol) in THF (50 mL) was added 2N HCl (50 mL) at room temperature. After 24 hours, water (100 mL) was added to the mixture, then the mixture was extracted with ethyl acetate (100 mL×2), the organic layer was washed with water (50 mL), dried over MgSO4. Removal of the solvent, gave a title compound (6.98 g, 60% yield).

$^1$H-NMR (CDCl$_3$) δ 9.77 (s, 1H), 7.61–7.65 (m, 2H), 7.47–7.51 (m, 1H), 7.07 (br s, 1H), 4.43–4.45 (m, 2H).

2-(4-Bromo-2-chlorophenyl)-1,3-oxazole (Step 3).

To a stirred solution of 4-bromo-2-chloro-N-(2-oxoethyl) benzamide (1.00 g, 3.617 mmol) in CH2Cl2 (30 mL) were added triphenylphosphine (1.90 g, 7.234 mmol), iodine (1.84 g, 7.234 mmol) and triethylamine (2.0 mL, 14.47 mmol) at room temperature. After 24 hour, the mixture was washed with water (20 mL), dried over MgSO4. Removal of the solvent, gave an oily recidue, which was purified by flash chromatography eluting with ethyl acetate/hexane (1/5) to give title compound (0.185 g, 20% yield).

$^1$H-NMR (CDCl$_3$) δ 7.88 (d, J=8.4 Hz, 1H), 7.80 (d, J=0.8 Hz, 2H), 7.70 (d, J=1.6 Hz, 1H), 7.51 (dd, J=2.0, 8.4 Hz, 1H), 7.32 (d, J=0.7 Hz, 2H).

1-[3-Chloro-4-(1,3-oxazol-2-yl)phenyl]-1-ethanone (Step 4).

To a stirred solution of 2-(4-bromo-2-chlorophenyl)-1,3-oxazole (2.88 g, 11.14 mmol) in 1,4-dioxane (70 mL) were added tributyl(1-ethoxyvinyl)tin (4.5 mL, 13.37 mmol), LiCl (1.18 g, 27.85 mmol) and tetrakis(triphenylphosphine) palladium(0) (1.28 g, 1.11 mmol) at room temperature under nitrogen. The mixture was heated at reflux temperature for 4 hours, and cooled down to room temperature, the solvent was removed under reduced pressure and the residue was dissolved in ethyl acetate (50 mL), washed with water (20 mL), dried over MgSO4 and concentrated in vacuo. The residue was dissolved in THF (30 mL) then 2N HCl (30 ml) was added at room temperature. After 2 hours, saturated NaHCO3 (100 mL) was added to the mixture. The mixture was extracted with ethyl acetate (300 mL) dried over MgSO4. Removal of the solvent, gave an oily residue, which was purified by flash chromatography eluting with ethyl acetate/hexane (1/4) to give title compound (1.891 g, 77% yield).

$^1$H-NMR (CDCl$_3$) δ 8.15 (d, J=8.1 Hz, 1H), 8.08 (d, J=1.6 Hz, 1H), 7.92 (dd, J=1.8, 8.2 Hz, 1H), 7.84 (d, J=0.7 Hz, 1H), 7.38 (d, J=0.7 Hz, 1H), 2.64 (s, 3H).

1-[3-Chloro-4-(1,3-oxazol-2-yl)phenyl]-4,4,4-trifluoro-1,3-butanedione (Step 5)

To a solution of 1-[3-chloro-4-(1,3-oxazol-2-yl)phenyl]-1-ethanone (1.89 g, 8.572 mmol) in t-butyl methyl ether (100 mL) were added ethyl trifluoroacetate (1.1 mL, 9.38 mmol) and 28%wt sodium methoxide in MeOH (2.6 ml) at 0° C. and stirred at room temperature for 4 hours. Water (100 mL) was added to the mixture, the mixture was neutralized with 2N HCl, extracted with ethyl acetate (100 mL×2) and dried over MgSO4. Removal of the solvent, gave a title compound (3.08 g).

5-[5-[3-Chloro-4-(1,3-oxazol-2-yl)phenyl]-3-(trifluoromethyl)-1H-pyrazol-1-yl]-2-pyridinesulfonamide (Step 6)

The subtitle compound was prepared according to the procedure of Example 1 (Step 2) using 1-[3-chloro-4-(1,3-oxazol-2-yl)phenyl]-4,4,4-trifluoro-1,3-butanedione, instead of 4,4,4-trifluoro-1-[4-(2-furyl)phenyl]butane-1,3-dione and 5-hydrazino-2-pyridinesulfonamide hydrochloride instead of 2-hydrazino-5-sulfamoylpyridine dihydrochloride.

mp: 156° C. $^1$H-NMR (CDCl$_3$) δ: 8.69 (dd, J=0.8, 2.5 Hz, 1H), 8.08 (d, J=0.8 Hz, 1H), 8.05 (d, J=8.0 Hz, 1H), 7.92 (dd, J=2.5, 8.4 Hz, 1H), 7.84 (d, J=0.8 Hz, 1H), 7.53 (d, J=1.5 Hz, 1H), 7.36 (d, J=0.8 Hz, 1H), 7.16 (dd, J=1.8, 8.2 Hz, 1H), 6.92 (s, 1H), 5.14 (br s, 2H). Anal. Calcd. for C$_{18}$H$_{11}$ClF$_3$N$_5$O$_3$S.0.2H$_2$O: C, 45.67; H, 2.43; N, 14.79. Found: C, 46.01; H, 2.59; N, 14.48.

Example 4

5-{4-Chloro-5-[4-(1,3-thiazol-4-yl)phenyl]-3-(trifluoromethyl)-1H-pyrazol-1-yl}-2-pyridinesulfonamide Hydrochloride 5-[5-(4-Bromophenyl)-3-(trifluoromethyl)-1H-pyrazol-1-yl]-2-pyridinesulfonamide (Step 1).

A mixture of 1-(4-bromophenyl)-4,4,4-trifluoro-1,3-butanedione (prepared according to the method of J.Med.Chem., 1997, 40, 1347. 1.09 g, 3.71 mmol) and 5-hydrazino-2-pyridinesulfonamide hydrochloride (1.00 g, 4.45 mmol) in ethanol (50 ml) was refluxed for 18 hr. After evaporation, the obtained residue was chromatographed on a column of silica gel (200 g) eluting with ethyl acetate/hexane (1:2) to afford 1.44 g (87%) of the title compound as a white solid.

$^1$H-NMR (DMSO-d6) δ: 8.71 (1H, d, J=2.3 Hz), 8.08 (1H, dd, J=2.3 and 8.4 Hz), 8.02 (1H, d, J=8.4 Hz), 7.70–7.64 (2H, m), 7.63 (2H, br s), 7.37–7.31 (2H, m), 7.36 (1H, s).

5-[5-(4-Bromophenyl)-4-chloro-3-(trifluoromethyl)-1H-pyrazol-1-yl]-2-pyridinesulfonamide (Step 2)

To a solution of 5-[5-(4-bromophenyl)-3-(trifluoromethyl)-1H-pyrazol-1-yl]-2-pyridinesulfonamide (350 mg, 0.783 mmol) in N,N-dimethylformamide (12 ml) was added N-chlorosuccinimide (1.05 g, 7.83 mmol) at room temperature. After the mixture was stirred for 18 hr, 1.05 g of N-chlorosuccinimide was added. The resulting mixture was stirred for further 36 hr. 20 ml of saturated aqueous sodium thiosulfate and 50 ml of diethyl ether were added and the two-phase-mixture was stirred for 0.5 hr. The separated organic layer was washed with water (20 ml×3) and dried over magnesium sulfate. Removal of solvent gave a pale yellow gum, which was chromatographed on a column of silica gel (50 g) eluting with ethyl acetate/hexane (1:3) to afford 236 mg (63%) of the title compound as a white solid.

$^1$H-NMR (CDCl$_3$) δ: 8.59 (1H, d, J=2.5 Hz), 8.03 (1H, d, J=8.4 Hz), 7.83 (1H, dd, J=2.5 and 8.6 Hz), 7.67–7.61 (2H, m), 7.21–7.16 (2H, m), 5.11 (2H, br s). MS (EI): 480 and 482 (M$^+$).

5-{4-Chloro-5-[4-(1,3-thiazol-4-yl)phenyl]-3-(trifluoromethyl)-1H-pyrazol-1-yl}-2-pyridinesulfonamide (Step 3)

A mixture of 5-[5-(4-bromophenyl)-4-chloro-3-(trifluoromethyl)-1H-pyrazol-1-yl]-2-pyridinesulfonamide (236 mg, 0.489 mmol), 4-(tributylstannyl)-1,3-thiazole 238 mg, 0.636 mmol), lithium chloride (27 mg, 0.636 mmol) and tetrakis(triphenyphosphine)palladium (57 mg, 0.0489 mmol) in 1,4-dioxane (10 ml) was refluxed for 5 hr under nitrogen atmosphere. After evaporation, the residue obtained was chromatographed on a column of silica gel (50 g) eluting with ethyl acetate/hexane (3:4) to afford 200 mg (84%) of the title compound as a pale brown gum.

$^1$H-NMR (CDCl$_3$) δ: 8.89 (1H, d, J=2.0 Hz), 8.62 (1H, d, J=1.6 Hz), 8.05–7.98 (2H, m), 7.94 (1H, dd, J=2.8 and 8.6 Hz), 7.83–7.76 (1H, m), 7.65 (1H, d, J=2.0 Hz), 7.39–7.33 (2H, m), 5.55 (2H, br s).

5-[4-Chloro-5-[4-(1,3-thiazol-4-yl)phenyl]-3-(trifluoromethyl)-1H-pyrazol-1-yl]-2-pyridinesulfonamide Hydrochloride (Step 4)

To a solution of 5-{4-chloro-5-[4-(1,3-thiazol-4-yl)phenyl]-3-(trifluoromethyl)-1H-pyrazol-1-yl}-2-pyridinesulfonamide (200 mg, 0.412 mmol) in dichloromethane (6 ml) was added methanolic hydrochloric acid (2 ml) at room temperature. The solution stood for a while and a formed solid was collected to give 160 mg (74%) of the title compound as a white solid.

m.p.: 157° C. (recrystallized from dichloromethane/methanol); $^1$H-NMR (DMSO-d6) δ: 9.24 (1H, d, J=2.0 Hz), 8.70 (1H, d, J=2.3 Hz), 8.33 (1H, d, J=1.8 Hz), 8.16–8.08 (3H, m), 8.02 (1H, d, J=8.4 Hz), 7.62 (2H, br s), 7.56–7.50 (2H, m). MS (EI): 485 (M$^+$).

Example 5

5-{5-[4-(1,3-Thiazol-4-yl)-3-(trifluoromethyl)phenyl]-3-(trifluoromethyl)-1H-pyrazol-1-yl}-2-pyridinesulfonamide 1-[4-Nitro-3-(trifluoromethyl)phenyl]-1-ethanone (Step 1)

A mixture of 4-bromo-1-nitro-2-(trifluoromethyl)benzene (1.87 g, 6.93 mmol), tributyl(1-ethoxyvinyl)tin (3.00 g, 8.31 mmol), Pd(PPh$_3$)$_4$ (801 mg, 0.693 mmol), and LiCl (734 mg, 17.3 mmol) in 1,4-dioxane (50 ml) was heated to reflux for 7 hours. The mixture was filtered through a pad of Celite with ethyl acetate. The filtrate was washed with water (100 ml) and brine (100 ml), dried over MgSO$_4$, and evaporated in vacuo. To the obtained residue were added 2N HCl (20 ml) and THF (60 ml). The mixture was stirred at room temperature for 1.5 hours. Saturated aqueous NaHCO$_3$ (60 ml) was added and the aqueous layer was extracted with ethyl acetate (100 ml×2). The combined organic layer was dried over MgSO$_4$, and evaporated in vacuo. The resulting residue was chromatographed over silica gel with hexane/ethyl acetate (3:1) to give 1.51 g (94%) of the title compound as a white solid.

$^1$H-NMR (CDCl$_3$) δ: 8.39 (1H, d, J=1.9 Hz), 8.28 (1H, dd, J=1.9, 8.4 Hz), 7.96 (1H, d, J=8.4 Hz), 2.71 (3H, s).

1-[4-Amino-3-(trifluoromethyl)phenyl]-1-ethanone (Step 2)

A mixture of 1-[4-nitro-3-(trifluoromethyl)phenyl]-1-ethanone (1.41 g, 6.05 mmol), Fe powder (1.69 g, 30.2 mmol), and NH$_4$Cl (324 mg, 6.05 mmol) in EtOH (24 ml) and water (9 ml) was heated to reflux for 2.5 hours. After cooling to room temperature, the mixture was filtered through a pad of Celite and the filtrate was concentrated. And the residue was dissolved with ethyl acetate (100 ml), washed with water (100 ml), dried over MgSO$_4$, and concentrated in vacuo to give 1.22 g (quant.) of the title compound as a pale yellow oil.

$^1$H-NMR (CDCl$_3$) δ: 8.07 (1H, d, J=1.9 Hz), 7.92 (1H, dd, J=1.6, 8.4 Hz), 6.75 (1H, d, J=8.4 Hz), 2.53 (3H, s).

1-[4-Bromo-3-(trifluoromethyl)phenyl]-1-ethanone (Step s3)

To a solution of t-butyl nitrite (936 mg, 9.08 mmol) and CuBr$_2$ (1.62 g, 7.26 mmol) in MeCN (35 ml) was added a solution of 1-[4-amino-3-(trifluoromethyl)phenyl]-1-ethanone (1.30 g, 6.40 mmol) in MeCN (15 ml) at 0° C. The mixture was stirred at 0° C. for 30 minutes, poured into 2N HCl (100 ml), and extracted with ethyl acetate (100 ml). The organic layer was washed with 2N HCl (50 ml), dried over MgSO$_4$, and concentrated in vacuo to give 1.34 g (78%) of the title compound as a white solid.

$^1$H-NMR (CDCl$_3$) δ: 8.25 (1H, d, J=2.2 Hz), 7.95 (1H, dd, J=2.2, 8.4 Hz), 7.84 (1H, d, J=8.4 Hz), 2.63 (3H, s).

1-[4-Bromo-3-(trifluoromethyl)phenyl]-4,4,4-trifluoro-1,3-butanedione (Step 4)

To a solution of 1-[4-bromo-3-(trifluoromethyl)phenyl]-1-ethanone (1.34 g, 5.65 mmol) in THF (30 ml) was added lithium bis(trimethylsilyl)amide (1.0 M THF solution, 6.8 ml, 6.8 mmol) at −78° C. The mixture was stirred at 0° C. for 15 minutes and the solution was again cooled to −78° C. N-trifluoroacetylimidazole (1.15 g, 6.78 mmol) was added to the solution at the same temperature. The resulting mixture was stirred at −78° C. for 15 minutes and at room temperature for 2.5 hours. The reaction was quenched with 2N HCl (100 ml). The organic layer was separated and the aqueous layer was extracted with ethyl acetate (100 ml×2). The combined organic layer was washed with brine (200 ml), dried over MgSO$_4$, and concentrated in vacuo to give 1.80 g (88%) of the title compound as a pale yellow solid.

$^1$H-NMR (CDCl$_3$) δ: 8.23 (1H, d, J=2.1 Hz), 7.93 (1H, dd, J=1.8, 8.4 Hz), 7.89 (1H, d, J=8.4 Hz), 6.57 (1H, s).

5-{5-[4-Bromo-3-(trifuoromethyl)phenyl]-3-(trifluoromethyl)-1H-pyrazol-1-yl}-2-pyridinesulfonamide (Step 5)

The title compound was prepared according to the procedure of step 1 in the example 4 using 1-[4-bromo-3-(trifluoromethyl)phenyl]-4,4,4-trifluoro-1,3-butanedione, instead of 1-(4-bromophenyl)-4,4,4-trifluoro-1,3-butanedione.

$^1$H-NMR (CDCl$_3$) δ: 8.64 (1H, d, J=2.6 Hz), 8.08 (1H, d, J=8.4 Hz), 7.91 (1H, dd, J=2.6, 8.4 Hz), 7.76 (1H, d, J=8.4 Hz), 7.70 (1H, d, J=2.0 Hz), 7.15 (2H, dd, J=2.2, 8.3 Hz), 5.17 (2H, br).

5-{5-[4-(1,3-Thiazol-4-yl)-3-(trifluoromethyl)phenyl]-3-(trifluoromethyl)-1H-pyrazol-1-yl}-2-pyridinesulfonamide (Step 6)

The title compound was prepared according to the procedure of step 3, 4 in the example 4 using 5-{5-[4-bromo-3-(trifluoromethyl)phenyl]-3-(trifluoromethyl)-1H-pyrazol-1-yl}-2-pyridinesulfonamide, instead of 5-[5-(4-bromophenyl)-4-chloro-3-(trifluoromethyl)-1H-pyrazol-1-yl]-2-pyridinesulfonamide.

m.p.: 114° C. (from ethanol/hexane); $^1$H-NMR (DMSO-d$_6$) δ: 9.23 (1H, d, J=1.8 Hz), 8.80 (1H, d, J=2.4 Hz), 8.17 (1H, dd, J=2.4, 8.1 Hz), 8.05 (1H, d, J=8.4 Hz), 7.98–7.94 (2H, m), 7.71 (1H, d, J=7.8 Hz), 7.67–7.62 (3H, m), 7.56 (1H, s). MS; 519 (M$^+$).

Example 6

5-{5-[4-(1,3-Thiazol-4-yl)phenyl]-3-(trifluoromethyl)-1H-pyrazol-1-yl}-2-pyridinesulfonamide Hydrochloride 5-{5-[4-(1,3-Thiazol-4-yl)phenyl]-3-(trifluoromethyl)-1H-pyrazol-1-yl}-2-pyridinesulfonamide (Step 1)

The title compound was prepared according to the procedure of step 3 in the Example 4 using 5-[5-(4-bromophenyl)-3-(trifluoromethyl)-1H-pyrazol-1-yl]-2-pyridinesulfonamide (Example 4, step 1), instead of 5-[5-(4-bromophenyl)-4-chloro-3-(trifluoromethyl)-1H-pyrazol-1-yl]-2-pyridinesulfonamide.

$^1$H-NMR (CDCl$_3$) δ: 8.89 (1H, d, J=1.8 Hz), 8.67 (1H, d, J=2.0 Hz), 8.02–7.93 (3H, m), 7.87 (1H, dd, J=2.5 and 8.4 Hz), 7.63 (1H, d, J=2.0 Hz), 7.34–7.28 (2H, m), 6.86 (1H, s), 5.43 (2H, br s).

5-{5-[4-(1,3-Thiazol-4-yl)phenyl]-3-(trifluoromethyl)-1H-pyrazol-1-yl}-2-pyridinesulfonamide Hydrochloride (Step 2)

To a solution of 5-{5-[4-(1,3-thiazol-4-yl)phenyl]-3-(trifluoromethyl)-1H-pyrazol-1-yl}-2-pyridinesulfonamide (470 mg, 1.04 mmol) in dichloromethane (6 ml) was added methanolic hydrochloric acid (4 ml) at room temperature. After evaporation, the residue obtained was recrystallized from methanol/diethyl ether to give 467 mg (92%) of the title compound as a white solid.

m.p.: 121° C. (recrystallized from methanol/diethyl ether); $^1$H-NMR (DMSO-d6) δ: 9.23 (1H, d, J=1.8 Hz), 8.74 (1H, d, J=2.3 Hz), 8.31 (1H, d, J=2.0 Hz), 8.11 (1H, dd, J=2.5 and 8.4 Hz), 8.08–8.00 (3H, m), 7.63 (2H, br s), 7.50–7.43 (2H, m), 7.38 (1H, s). MS (EI): 451 (M$^+$).

Example 7

5-{5-Ethyl-[4-(1,3-thiazol-4-yl)phenyl]-3-(trifluoromethyl)-1H-pyrazol-1-yl}-2-pyridinesulfonamide Hydrochloride 4-Bromo-N-methoxy-N-methylbenzamide (Step 1)

To a solution of 4-bromobenzoyl chloride (12.43 g, 56.6 mmol) and N,O-dimethyl hydroxyamine hydrochloride (8.29 g, 85.0 mmol) in CH$_2$Cl$_2$ (200 ml) was added triethylamine (23.7 ml, 170 mmol) at 0° C. The mixture was stirred at room temperature for 2 hours. Water (200 ml) was added and the aqueous layer was extracted with CH$_2$Cl$_2$ (150 ml×2). The combined organic layer was washed with 2N HCl (200 ml), saturated aqueous NaHCO$_3$ (200 ml), and brine (200 ml), dried over Na$_2$SO$_4$, and concentarated in vacuo to give 14.9 g (quant.) of the title compound as a white solid.

$^1$H-NMR (CDCl$_3$) δ: 7.61–7.52 (4H, m), 3.54 (3H, s), 3.36 (3H, s).

1-(4-Bromophenyl)-1-butanone (Step 2)

To a solution of 4-bromo-N-methoxy-N-methylbenzamide (13.4 g, 54.2 mmol) in THF (200 ml) was added n-PrMgBr (2M THF solution, 54.0 ml, 108 mmol) at 0° C. The mixture was stirred at room temperature for 45 minutes. Further n-PrMgBr (13.5 ml, 27.0 mmol) was added at 0° C., and the mixture was stirred at room temperature for 30 minutes. The excess reagent was quenched with saturated aqueous NH$_4$Cl (200 ml), and ether (300 ml) was added. The organic layer was separated and the aqueous layer was extracted with ether (300 ml). The combined organic layer was washed with water (200 ml) and brine (200 ml), dried over Na$_2$SO$_4$, and concentrated in vacuo. The obtained residue was chromatographed on a column of silica gel eluting with hexane/ethyl acetate (15:1) to give 10.1 g (82%) of the title compound as a yellow solid.

$^1$H-NMR (CDCl$_3$) δ: 7.82 (2H, d, J=8.6 Hz), 7.60 (2H, d, J=8.6 Hz), 2.91 (2H, t, J=7.2 Hz), 1.76 (2H, sextet, J=7.3 Hz), 1.00 (3H, t, J=7.4 Hz).

1-(4-Bromophenyl)-2-ethyl-4,4,4-trifluoro-1,3-butanedione (Step 3)

To a solution of hexamethyldisilazane (4.92 g, 30.5 mmol) in THF (10 ml) was added dropwise n-BuLi (1.57 M hexane solution, 19.4 ml, 30.5 mmol) at −78° C. and the mixture was stirred at room temperature for 15 minutes. The mixture was cooled down to −78° C. again and 1-(4-bromophenyl)-1-butanone (5.77 g, 25.4 mmol) in THF (25 ml) was added dropwise over 15 min. The resulting mixture was stirred at −78° C. for 30 minutes, then allowed to warm up to 0° C. and stirred for 40 minutes. The solution was recooled down to −78° C. and N-trifluoroacetylimidazole (5.00 g, 30.5 mmol) was added. The mixture was stirred at −78° C. for 20 minutes, and at room temperature for 2 hours. The reaction was quenched with 2N HCl (30 ml). The organic layer was separated and the aqueous layer was extracted with ethyl acetate (50 ml×2). The combined organic layer was washed with brine (50 ml), dried over Na$_2$SO$_4$, and concentrated in vacuo. The residue was chromatographed over silica gel with hexane/ethyl acetate (8:1 to 3:1) to give 5.64 g (69%) of the title compound as a oil.

TLC: Rf=0.35 (hexane/ethyl acetate=5/1).

5-[5-(4-Bromophenyl)-4-ethyl-3-(trifluoromethyl)-1H-pyrazol-1-yl]-2-pyridinesulfonamide (Step 4)

The title compound was prepared according to the procedure of step 1 in the Example 4 using 1-(4-bromophenyl)-2-ethyl-4,4,4-trifluoro-1,3-butanedione, instead of 1-(4-bromophenyl)-4,4,4-trifluoro-1,3-butanedione.

$^1$H-NMR (CDCl$_3$) δ: 8.57 (1H, d, J=2.5 Hz), 7.94 (1H, d, J=8.4 Hz), 7.76 (1 H, dd, J=2.5 and 8.4 Hz), 7.65–7.58 (2H, m), 7.15–7.08 (2H, m), 2.55 (2H, q, Hz), 1.13 (3H, t, J=7.6 Hz).

5-{4-Ethyl-5-[4-(1,3-thiazol-4-yl)phenyl]-3-(trifluoromethyl)-1H-pyrazol-1-yl}-2-pyridinesulfonamide (Step 5)

The title compound was prepared according to the procedure of step 3 in the Example 4 using 5-[5-(4-bromophenyl)-4-ethyl-3-(trifluoromethyl)-1H-pyrazol-1-yl]-2-pyridinesulfonamide, instead of 5-[5-(4-bromophenyl)-4-chloro-3-(trifluoromethyl)-1H-pyrazol-1-yl]-2-pyridinesulfonamide.

$^1$H-NMR (CDCl$_3$) δ: 8.91 (1H, d, J=2.0 Hz), 8.60 (1H, d, J=2.5 Hz), 8.07–8.00 (2H, m), 7.92 (1H, d, J=8.6 Hz), 7.80 (1H, dd, J=2.5 and 8.6 Hz), 7.65 (1H, d, J=2.0 Hz), 7.34–7.27 (2H, m), 5.26 (2H, br s), 2.60 (2H, q, J=7.7 Hz), 1.15 (3H, t, J=7.4 Hz).

5-{4-Ethyl-5-[4-(1,3-thiazol-4-yl)phenyl]-3-(trifluoromethyl)-1H-pyrazol-1-yl}-2-pyridinesulfonamide Hydrochloride (Step 6)

The title compound was prepared according to the procedure of step 2 in the Example 6 using 5-{4-ethyl-5-[4-(1,3-thiazol-4-yl)phenyl]-3-(trifluoromethyl)-1H-pyrazol-1-yl}-2-pyridinesulfonamide, instead of 5-{5-[4-(1,3-thiazol-4-yl)phenyl]-3-(trifluoromethyl)-1H-pyrazol-1-yl}-2-pyridinesulfonamide.

m.p.: 141° C. (recrystallized from dichloromethane/ethyl acetate); $^1$H-NMR (DMSO-d6) δ: 9.24 (1H, d, J=1.8 Hz), 8.61 (1H, d, J=2.5 Hz), 8.32 (1H, d, J=1.8 Hz), 8.13–8.07 (2H, m), 8.02 (1H, dd, J=2.5 and 8.4 Hz), 7.96 (1H, d, J=8.4 Hz), 7.56 (2H, br s), 7.50–7.45 (2H, m), 2.56 (2H, q, J=7.3 Hz), 1.10 (3H, t, J=7.4 Hz). MS (EI): 479 (M$^+$).

Example 8

5-[4-Ethyl-5-[4-(1,3-thiazol-5-yl)phenyl]-3-(trifluoromethyl)-1H-pyrazol-1-yl]-2-pyridinesulfonamide Hydrochloride 5-[4-Ethyl-5-[4-(1,3-thiazol-5-yl)phenyl]-3-(trifluoromethyl)-1H-pyrazol-1-yl]-2-pyridinesulfonamide (Step 1).

The title compound was prepared according to the procedure of Example 7 step 5 using 5-tributylstannylthiazole, instead of 4-tributylstannylthiazole.

$^1$H-NMR (CDCl$_3$) δ: 8.83 (s, 1H), 8.59 (d, J=1.8 Hz, 1H), 8.17 (s, 1H), 7.98 (d, J=7.7 Hz, 1H), 7.85 (dd, J=2.5, 8.4 Hz, 1H), 7.69 (d, J=8.6 Hz, 2H), 7.28 (d, J=9.2 Hz, 2H), 5.07 (br s, 2H), 2.60 (q, J=7.4 Hz, 2H), 1.16 (t, J=7.4 Hz, 3H).

5-[4-Ethyl-5-[4-(1,3-thiazol-5-yl)phenyl]-3-(trifluoromethyl)-1H-pyrazol-1-yl]-2-pyridinesulfonamide Hydrochloride (Step 2).

The title compound was prepared according to the procedure of Example 4 step 4 using 5-[4-ethyl-5-[4-(1,3-thiazol-5-yl)phenyl]-3-(trifluoromethyl)-1H-pyrazol-1-yl]-2-pyridinesulfonamide, instead of 5-{4-chloro-5-[4-(1,3-thiazol-4-yl)phenyl]-3-(trifluoromethyl)-1H-pyrazol-1-yl}-2-pyridinesulfonamide.

mp: 169° C. $^1$H-NMR (DMSO-d6) δ: 9.15 (s, 1H), 8.63 (dd, J=0.8, 2.3 Hz, 1H), 8.44 (d, J=0.7 Hz, 1H), 8.01 (d, J=2.5 Hz, 1H), 7.98 (d, J=0.8 Hz, 1H), 7.83 (d, J=8.6 Hz, 2H), 7.58 (br s, 2H), 7.48 (d, J=8.4 Hz, 2H), 7.39 (s, 1H). Anal. Calcd. for C$_{20}$H$_{16}$F$_3$N$_5$O$_2$S$_2$.1HCl.1.5H$_2$O: C, 44.24; H, 3.71; N, 12.90. Found: C, 44.54; H, 3.58; N, 12.83.

Example 9

5-{4-Fluoro-5-[4-(1,3-thiazol-4-yl)phenyl]-3-(trifluoromethyl)-1H-pyrazol-1-yl}-2-pyridinesulfonamide Hydrochloride 1-(4-Bromophenyl)-2-fluoro-1-ethanone (Step 1)

A mixture of 2-bromo-1-(4-bromophenyl)-1-ethanone (8.54 g, 30.7 mmol), potassium fluoride (8.92 g, 153 mmol) and 18-crown-6 ether (4.06 g, 15.3 mmol) in acetonitrile (170 ml) was refluxed for 7 hr. After evaporation, the mixture was dissolved in ethyl acetate (300 ml), washed with water (100 ml×2), and dried over magnesium sulfate. Removal of solvent gave 6.8 g of brown solid, which was chromatographed on a column of silica gel (600 g) eluting with ethyl acetate/hexane (1:10) to afford 5.00 g (75%) of the title compound as a pale yellow solid.

$^1$H-NMR (CDCl$_3$) δ: 7.81–7.76 (2H, m), 7.68–7.63 (2H, m), 5.47 (2H, d, J=46.9 Hz).

5-[4-Fluoro-5-(4-bromopheny)-3-(trifluoromethyl)-1H-pyrazol-1-yl]-2-pyridinesulfonamide (Step 2)

To a solution of 1-(4-bromophenyl)-2-fluoro-1-ethanone (3.54 g, 16.3 mmol) in tetrahydrofuran (50 ml) was added dropwise 1M lithium hexamethyldisilazide tetrahydrofuran solution (19.6 ml, 19.6 mmol) at −78° C. After stirring for 45 min., N-trifluoroacetylimidazole (2.3 ml, 19.6 mmol) was added. The resulting mixture was allowed to warm up to room temperature and stirred for 1.5 hr. The mixture was acidified with 2M hydrochloric acid and extracted with diethyl ether (300 ml). The separated organic layer was washed with water (100 ml×3) and dried over magnesium sulfate. The solution was evaporated to give 5.2 g of 1-(4-bromophenyl)-2,4,4,4-tetrafluoro-1,3-butanedione as a brown oil. This residue was heated with 5-hydrazino-2-pyrisinesulfonamide hydrochloride (1.10 g, 4.89 mmol) at refluxing temperature for 18 hr. After evaporation, the obtained residue was chromatographed on a column of silica gel (500 g) eluting with ethyl acetate/hexane (1:3 to 1:1) to afford 930 mg (12%) of the title compound as a yellow solid.

$^1$H-NMR (DMSO-d6) δ: 8.70 (1H, dd, J=0.8 and 2.3 Hz), 8.08 (1H, dd, J=2.3 and 8.4 Hz), 8.03 (1H, d, J=8.6 Hz), 7.76–7.70 (2H, m), 7.64 (2H, br s), 7.42–7.36 (2H, m). MS (EI): 464 and 466 (M$^+$).

5-{4-Fluoro-5-[4-(1,3-thiazol-4-yl)phenyl]-3-(trifluoromethyl)-1H-pyrazol-1-yl}-2-pyridinesulfonamide (Step 3)

The title compound was prepared according to the procedure of step 3 in the Example 4 using 5-[4-fluoro-5-(4-bromophenyl)-3-(trifluoromethyl)-1H-pyrazol-1-yl]-2-pyridinesulfonamide, instead of 5-[5-(4-bromophenyl)-4-chloro-3-(trifluoromethyl)-1H-pyrazol-1-yl]-2-pyridinesulfonamide.

$^1$H-NMR (CDCl$_3$) δ: 8.90 (1H, d, J=2.0 Hz), 8.67 (1H, d, J=2.5 Hz), 8.06–7.98 (3H, m), 7.86 (1H, dd, J=2.5 and 8.6 Hz), 7.65 (1H, d, J=2.0 Hz), 7.37–7.31 (2H, m), 5.41 (2H, br s).

5-{4-Fluoro-5-[4-(1,3-thiazol-4-yl)phenyl]-3-(trifluoromethyl)-1H-pyrazol-1-yl}-2-pyridinesulfonamide Hydrochloride (Step 4)

The title compound was prepared according to the procedure of step 2 in the Example 6 using 5-{4-fluoro-5-[4-(1,3-thiazol-4-yl)phenyl]-3-(trifluoromethyl)-1H-pyrazol-1-yl}-2-pyridinesulfonamide, instead of 5-{5-[4-(1,3-thiazol-4-yl)phenyl]-3-(trifluoromethyl)-1H-pyrazol-1-yl}-2-pyridinesulfonamide.

m.p.: 145° C. (recrystallized from methanol/dichloromethane); $^1$H-NMR (DMSO-d6) δ: 9.24 (1H, d, J=1.8 Hz), 8.73 (1H, d, J=2.3 Hz), 8.33 (1H, d, J=1.8 Hz), 8.15–8.08 (3H, m), 8.04 (1H, d, J=8.4 Hz), 7.63 (2H, br s), 7.47 (2H, m). MS (EI): 469 (M$^+$).

Example 10

5-[5-[4-(1,3-Thiazol-5-yl)phenyl]-3-(trifluoromethyl)-1H-pyrazol-1-yl]-2-pyridinesulfonamide Hydrochloride 5-[5-[4-(1,3-Thiazol-5-yl)phenyl]-3-(trifluoromethyl)-1H-pyrazol-1-yl]-2-pyridinesulfonamide (Step 1).

The mixture of 5-[5-(4-bromophenyl)-3-(trifluoromethyl)-1H-pyrazol-1-yl]-2-pyridinesulfonamide (400 mg, 0.8944 mmol) in 1,4-dioxane (10 mL) were added 5-tributylstannylthiazole (401 mg, 1.073 mmol), LiCl (94.8 mg, 2.236 mmol) and tetrakis(triphenylphosphine) palladium(0) (103 mg, 0.0894 mmol) at room temperature under nitrogen. The mixture was heated at reflux temperature for 16 hours, and cooled down to room temperature, the solvent was removed under reduced pressure and the residue was dissolved in ethyl acetate (100 mL), washed with water (30 mL), dried over MgSO4 and concentrated in vacuo. The residue was purified by flash chromatography eluting with ethyl acetate/hexane (1/1) to give title compound (281.3 mg, 70% yield).

¹H-NMR (CDCl₃) δ: 8.83 (s, 1H), 8.69 (d, J=1.6 Hz, 1H), 8.15 (s, 1H), 8.06 (d, J=8.4 Hz, 1H), 7.93 (dd, J=2.5, 8.4 Hz, 1H), 7.65 (d, J=8.6 Hz, 2H), 7.31 (d, J=8.6 Hz, 2H), 6.87 (s, 1H), 5.04 (br s, 1H).

5-[5-[4-(1,3-Thiazol-5-yl)phenyl]-3-(trifluoromethyl)-1H-pyrazol-1-yl]-2-pyridinesulfonamide Hydrochloride (Step 2).

The title compound was prepared according to the procedure of Example 4 using 5-[5-[4-(1,3-thiazol-5-yl)phenyl]-3-(trifluoromethyl)-1H-pyrazol-1-yl]-2-pyridinesulfonamide, instead of 5-{4-chloro-5-[4-(1,3-thiazol-4-yl)phenyl]-3-(trifluoromethyl)-1H-pyrazol-1-yl}-2-pyridinesulfonamide.

mp: 138° C. ¹H-NMR (DMSO-d6) δ: 9.14 (s, 1H), 8.75 (d, J=2.0 Hz, 1H), 8.43 (s, 1H), 8.12 (dd, J=2.5, 8.4 Hz, 1H), 8.03 (d, J=8.1 Hz, 1H), 7.79 (d,J=8.6 Hz, 2H), 7.64 (br s, 2H), 7.46 (d, J=8.2 Hz, 2H), 7.39 (s, 1H). Anal. Calcd. for $C_{18}H_{12}F_3N_5O_2S_2 \cdot 1HCl \cdot 0.5H_2O \cdot 0.3EtOH$: C, 43.74; H, 3.12; N, 13.71. Found: C, 43.72; H, 3.10; N, 13.36.

Example 11

5-{4-Fluoro-5-[4-(1,3-thiazol-5-yl)phenyl]-3-(trifluoromethyl)-1H-pyrazol-1-yl}-2-pyridinesulfonamide Hydrochloride 5-{4-Fluoro-5-[4-(1,3-thiazol-5-yl)phenyl]-3-(trifluoromethyl)-1H-pyrazol-1-yl}-2-pyridinesulfonamide (Step 1)

The title compound was prepared according to the procedure of step 1 in the Example 10 using 5-[4-fluoro-5-(4-bromophenyl)-3-(trifluoromethyl)-1H-pyrazol-1-yl]-2-pyridinesulfonamide (Example 8, step 1), instead of 5-[5-(4-bromophenyl)-5-ethyl-3-(trifluoromethyl)-1H-pyrazol-1-yl]-2-pyridinesulfonamide.

¹H-NMR (CDCl₃) δ: 8.84 (1H, s), 8.68 (1H, d, J=2.3 Hz), 8.17 (1H, s), 8.07 (1H, d, J=8.4 Hz), 7.92 (1H, dd, J=2.3 and 8.6 Hz), 7.73–7.67 (2H, m), 7.36–7.30 (2H, m), 5.08 (2H, br s).

5-{4-Fluoro-5-[4-(1,3-thiazol-5-yl)phenyl]-3-(trifluoromethyl)-1H-pyrazol-1-yl}-2-pyridinesulfonamide Hydrochloride (Step 2)

The title compound was prepared according to the procedure of step 2 in the Example 6 using 5-{4-fluoro-5-[4-(1,3-thiazol-5-yl)phenyl]-3-(trifluoromethyl)-1H-pyrazol-1-yl}-2-pyridinesulfonamide, instead of 5-{5-[4-(1,3-thiazol-4-yl)phenyl]-3-(trifluoromethyl)-1H-pyrazol-1-yl}-2-pyridinesulfonamide.

m.p.: 134° C. (recrystallized from methanol/acetone); ¹H-NMR (DMSO-d6) δ: 9.15 (1H, s), 8.75 (1H, d, J=2.3 Hz), 8.44 (1H, s), 8.12 (1H, dd, J=2.5 and 8.4 Hz), 7.85 (1H, d, J=8.4 Hz), 7.87–7.81 (2H, m), 7.65 (2H, br s), 7.52–7.45 (2H, m). MS (EI): 469 (M⁺).

Example 12

5-[5-Chloro-4-(1,3-thiazole-4-yl)phenyl]-3-(trifluoromethyl)-1H-pyrazol-1-yl]-2-pyridinesulfonamide Hydrochloride

[(4-tert-Butyldimethylsilyloxy)-3-chloro]phenyl-1-ethanone (Step 1)

To a solution of 1-(3-chloro-4-hydroxy)phenyl-1-ethanone (18.5 g, 0.11 mol, G. Leclerc et al., *J. Med. Chem.* 23, 738 (1980)) in DMF (300 mL), tert-butyldimethylsilylchloride (18 g, 0.12 mol) and imidazole (8.8 g, 0.13 mol) was added at room temperature and the mixture was stirred for 3 hours. The mixture was poured into water (300 mL) and extracted with diethyl ether (150 mL×2), washed with water (80 mL), dried over MgSO₄ and concentrated in vacuo gave clear brown oil. (33 g, quant.)

¹H-NMR (CDCl₃) δ: 7.98 (d, J=2.3 Hz, 1H), 7.75 (dd, J=2.3, 8.6 Hz, 1H), 6.91 (d, J=8.6 Hz, 1H), 2.54 (s, 3H), 2.04 (s, 9H), 0.26 (s, 6H).

1-(4-tert-Butyldimethylsilyloxy)-3-chlorophenyl-4,4,4-trifluoro-1,3-butanedione (Step 2)

To a solution of hexamethyldisilazane (1.8 mL, 8.4 mmol) in THF (20 mL), n-BuLi (1.53 M in n-hexane, 5.5 mL, 8.4 mmol) was added at 0° C. and stirred for 30 min at 0° C. The mixture was cooled to −70° C. and [(4-tert-butyldimethylsilyloxy)-3-chloro]phenyl-1-ethanone (from step 1, 2.0 g, 7.0 mmol) in THF (10 mL) was added dropwise and the mixture was stirred for 1 h at −70° C. Then trifluoroacetylimidazole (0.96 mL, 8.4 mmol) was added at −70° C. and the mixture was stirred for further 2 hours and water (30 mL) was added. 2N aqueous HCl was added to adjust pH to 4 and extracted with ethyl acetate (100 mL×2), dried over MgSO₄, and concentrated in vacuo gave pale red brown oil. (2.5 g, 93%).

¹H-NMR (CDCl₃) δ: 7.99 (s, 1H), 7.76 (d, J=8.0 Hz, 1H), 6.48 (d, J=8.0 Hz, 1H), 6.48 (s, 1H), 1.04 (s, 9H), 0.28 (s, 6H).

5-[5-(3-Chloro-4-hydroxyphenyl)-3-trifluoromethyl-1H-pyrazol-1-yl]-2-pyridinesulfonamide (Step 3)

To a solution of 1-(4-tert-butyldimethylsilyloxy)-3-chlorophenyl-4,4,4-trifluoro-1,3-butanedione (from step 2, 423 mg, 1.1 mmol) in EtOH (8 mL), 5-hydrazino-2-pyridinesulfonamide hydrochloride (300 mg, 1.3 mmol) was added and the mixture was refluxed for 12 hours. The mixture was cooled to room temperature and concentrated in vacuo and water (10 mL) was added and extracted with ethyl acetate (30 mL×2), dried over MgSO₄, and concentrated in vacuo gave oil (452 mg). The oil was dissolved in THF (8 mL) and TBAF (1.0 M in THF, 1.3 mL, 1.3 mmol) was added at 0° C. and the mixture was stirred for 30 min at room temperature. The mixture was poured into water (20 mL) and extracted with ethyl acetate (10 mL×3), dried over MgSO₄, and concentrated in vacuo. The residue was purified by flash chromatography eluting with ethyl acetate-hexane (1:2 to 1:1) to give title compound as a pale yellow powder (243 m g, 52%).

¹H-NMR (DMSO-d₆) δ: 8.71 (d, J=1.8 Hz, 1H), 8.07 (dd, J=2.5, 8.4 Hz, 1H), 8.02 (d, J=8.1 Hz, 1H), 7.63 (br s, 2H), 7.47 (d, J=2.0 Hz, 1H), 7.25 (s, 1H), 7.06 (d, J=2.1, 8.4 Hz, 1H), 6.96 (d, J=8.4 Hz, 1H), 7.61 (dd, J=7, 1 Hz, 1H), 7.47–7.46 (m, 2H), 2.64 (s, 3H).

[4-[1-[6-(Aminosulfonyl)-3-pyridinyl]-3-(trifluoromethyl)-1H-pyrazol-5-yl]-2-chlorophenyl]trifluoromethanesulfonate (Step 4)

To a solution of 5-[5-(3-chloro-4-hydroxyphenyl)-3-trifluoromethyl-1H-pyrazol-1-yl]-2-pyridinesulfonamide (from step 3, 2.4 g, 5.8 mmol) in CH₂Cl₂ (60 mL), 4-dimethylaminopyridine (1.0 g, 8.4 mmol) and trifluoromethanesulfonic anhydride (1.2 mL, 7.0 mmol) was added at 0° C. and the mixture was stirred for 30 min at room temperature. The mixture was concentrated in vacuo and water (20 mL) was added and extracted with ethyl acetate (80 mL), dried over MgSO₄, and concentrated in vacuo gave title compound as a brown amorphous solid (3.48 g, 100%).

¹H-NMR (CDCl₃) δ: 8.68 (d, J=2.5 Hz, 1H), 8.07 (d, J=8.4 Hz, 1H), 7.88 (dd, J=2.3, 8.4 Hz, 1H), 7.56 (d, J=2.1 Hz, 1H), 7.42 (d, J=8.6 Hz, 1H), 7.17 (dd, J=1.8, 8.6 Hz, 1H), 6.89 (s, 1H).

5-[5-Chloro-4-(1,3-thiazole-4-yl)phenyl]-3-(trifluoromethyl)-1H-pyrazol-1-yl]-2-pyridinesulfonamide Hydrochloride (Step 5)

The title compound was prepared according to the procedure of Example 4 step 3,4 using [4-[1-[6-(aminosulfonyl)-3-pyridinyl]-3-(trifluoromethyl)-1H-pyrazol-5-yl]-2-chlorophenyl]trifluoromethanesulfonate instead of 5-{4-chloro-5-[4-(1,3-thiazol-4-yl)phenyl]-3-(trifluoromethyl)-1H-pyrazol-1-yl}-2-pyridinesulfonamide.

mp: 118–120° C. ¹H-NMR (DMSO-d₆) δ: 8.97 (s, 1H), 8.71 (s, 1H), 8.10–8.02 (m, 3H), 7.92 (d, J=8.6 Hz, 1H), 7.51 (s, 1H), 7.18 (d, J=7.6 Hz, 1H), 6.91 (s, 1H). Anal. Calcd. for C₁₈H₁₁N₅O₂F₃Cl₂S₂: C, 41.39; H, 2.32; N, 13.41. Found: C, 42.80; H, 2.80; N, 12.68.

Example 13

5-[5-[3,5-Dichloro-4-(1,3-thiazol-5-yl)phenyl]-3-trifluoromethyl-1H-pyrazol-1-yl]-2-pyridinesulfoneamide Hydrochloride (4-Bromo-2,6-dichlorophenoxy)(tert-butyl)dimethylsilane (Step 1)

To a solution of 4-bromo-2,6-dichlorophenol (11.9 g, 49.2 mmol, H. Joyce et al., *J. Amer. Chem. Soc.*, 39, 2644 (1917)) in DMF (100 mL) imidazole (5.0 g, 74 mmol) and tert-butyldimethylsilylchloride (8.9 g, 59 mmol) was added at room temperature and the mixture was stirred for 1 h. The mixture was poured into water (300 mL) and extracted with diethyl ether (100 mL×2) and washed with water (50 mL×2), dried over MgSO₄ and concentrated in vacuo gave pale yellow oil. (15.3 g, 87%)

¹H-NMR (CDCl₃) δ: 7.40 (s, 2H), 1.04 (s, 9H), 0.28 (s, 6H).

1-[4-(tert-Butyldimethylsilyloxy)-3,5-dichlorophenyl]-1-ethanone (Step 2)

To a solution of (4-bromo-2,6-dichlorophenoxy)(tert-butyl)dimethylsilane (from step 1, 15.2 g, 42.7 mmol) in diethyl ether (100 mL), n-BuLi (1.57 M in n-hexane, 27.2 mL, 42.7 mmol) was added at −78° C. and the mixture was stirred for 1 h. N,N'-dimethylacetamide (4.2 mL, 44 mmol) in THF (20 mL) was added at −78° C. and the mixture was stirred for 2 hours. The mixture was added water (100 mL) and extracted with diethyl ether (50 mL×3), dried over MgSO₄ and concentrated in vacuo. The residue was purified by flash chromatography eluting with ethyl acetate-hexane (1:10) to give title compound as a pale yellow oil (4.7 g, 34%).

¹H-NMR (CDCl₃) δ: 7.87 (s, 2H), 2.55 (s, 3H), 1.06 (s, 9H), 0.32 (s, 6H).

(4-Acetyl-2,6-dichlorophenyl)trifluoromathanesulfonate (Step 3)

To a solution of 1-[4-(tert-butyldimethylsilyloxy)-3,5-dichlorophenyl]-1-ethanone (from step 2, 4.6 g, 14.5 mmol) in THF (50 mL) was added TBAF (1.0 M in THF, 17.4 mL) at 0° C. and the mixture was stirred for 1 h at room temperature. The mixture was poured into water (50 mL) and extracted with ethyl acetate (30 mL×2), dried over MgSO₄ and concentrated in vacuo gave title compound as a yellow brown oil. The oil was dissolved in CH₂Cl₂ (100 mL) and 4-dimethylaminopyridine (2.6 g, 21 mmol) and trifluoromethanesulfonic anhydride (2.9 mL, 17 mmol) was added at room temperature and the mixture was stirred for 0.5 h. The mixture was concentrated in vacuo and water (30 mL was added and extracted with ethyl acetate (50 mL×2), dried over MgSO₄ and concentrated in vacuo. The residue was purified by flash chromatography eluting with ethyl acetate-hexane (1:10) to give title compound as a white powder(2.1 g, 43%).

¹H-NMR (CDCl₃) δ: 8.00 (s, 2H), 2.62 (s, 3H).

2,6-Dichloro-4-(-4,4,4-trifluoro-1,3-oxobutanoyl)phenyl Trifluoromethanesulfonate (Step 4)

The title compound was prepared according to the procedure of step 2 of Example 12 using (4-acetyl-2,6-dichlorophenyl)trifluoromathanesulfonate instead of 1-[3-chloro-4-[(trimethylsilyl)oxy]phenyl]-1-ethanone.

¹H-NMR (CDCl₃) δ: 7.84 (s, 2H), 7.08 (br s, 1H), 6.20 (br s, 1H).

[4-[1-[6-(Aminosulfonyl)-3-pyridinyl]-3-(trifluoromethyl)-1H-pyrazol-5-yl]-2,6-dichlorophenyl]trifluoromethanesulfonate (Step 5)

The title compound was prepared according to the procedure of Example 4 using 2,6-Dichloro-4-(-4,4,4-trifluoro-1,3-oxobutanoyl)phenyl trifluoromethanesulfonate instead of 1-(4-bromophenyl)-4,4,4-trifluoro-1,3-butanedione.

¹H-NMR (CDCl₃) δ: 8.71 (d, J=2.3 Hz, 1H), 8.11 (d, J=8.2 Hz, 1H), 7.91 (dd, J=2.5, 8.4 Hz, 1H), 7.36 (s, 2H), 6.91 (s, 1H), 5.22 (br s, 2H).

5-[5-[3,5-Dichloro-4-(1,3-thiazol-5-yl)phenyl]-3-trifluoromethyl-1H-pyrazol-1-yl]-2-pyridinesulfoneamide Hydrochloride (Step 6)

The title compound was prepared according to the procedure of Example 6 using [4-[1-[6-(aminosulfonyl)-3-pyridinyl]-3-(trifluoromethyl)-1H-pyrazol-5-yl]-2,6-dichlorophenyl]trifluoromethanesulfonate instead of 5-{5-[4-(1,3-thiazol-4-yl)phenyl]-3-(trifluoromethyl)-1H-pyrazol-1-yl}-2-pyridinesulfonamide.

mp: 123–125° C. ¹H-NMR (DMSO-d₆) δ: 9.36 (s, 1H), 8.85 (d, J=2.3 Hz, 1H), 8.18 (dd, J=2.5, 8.4 Hz, 1H), 8.08 (d, J=8.4 Hz, 1H), 8.00 (s, 1H), 7.72 (s, 2H), 7.53 (s, 1H). Anal. Calcd. for C₁₈H₁₁N₅O₂F₃Cl₃S₂: C, 38.83; H, 1.99; N, 12.58. Found: C, 38.80; H, 2.49; N, 11.36.

Example 14

5-[5-Chloro-4-(1,3-thiazole-5-yl)phenyl]-3-(trifluoromethyl)-1H-pyrazol-1-yl]-2-pyridinesulfonamide Hydrochloride The title compound was prepared according to the procedure of Example 10 using [4-[1-[6-(aminosulfonyl)-3-pyridinyl]-3-(trifluoromethyl)-1H-pyrazol-5-yl]-2-chlorophenyl]trifluoromethanesulfonate from step 4 of example 12 instead of 5-[5-(4-bromophenyl)-3-(trifluoromethyl)-1H-pyrazol-1-yl]-2-pyridinesulfonamide.

mp: 167–168° C. 1H-NMR (DMSO-d₆) δ: 9.28 (s, 1H), 8.81 (d, J=2.0 Hz, 1H), 8.31 (s, 1H), 8.15 (dd, J=2.5, 8.4 Hz, 1H), 8.05 (d, J=8.4 Hz, 1H), 7.79 (d, J=8.1 Hz, 1H), 7.79 (d, J=1.6 Hz, 1H), 7.68 (br s, 1H), 7.48 (s, 1H), 7.36 (dd, J=1.8, 8.1 Hz, 1H), 5.76 (s, 2H), Anal. Calcd. for C18H11N5O2F3Cl2S2: C, 41.39; H, 2.32; N, 13.41. Found: C, 40.88; H, 2.35; N, 13.02.

Example 15

5-(5-(3-Fluoro-4-(1,3-thiazol-5-yl)phenyl)-3-trifluoromethyl-1H-pyrazol-1-yl)-2-pyridinesulfonamide Hydrochloride 1-(3-Fluoro-4-hydroxyphenyl)-1-ethanone (Step 1)

1-(3-Fluoro-4-hydroxyphenyl)-1-ethanone was prepared according to the procedure described in *J.Med.Chem.*, 23, 738–744 (1980).

4-Acetyl-2-fluorophenyl Trifluoromethanesulfonate (Step 2)

To a stirred solution of 1-(3-fluoro-4-hydroxyphenyl)-1-ethanone (3.9 g, 25.30 mmol) in pyridine (86 ml) was added trifluoromethanesulfonic anhydride (5.5 ml, 32.89 mmol) dropwise at 0° C. under nitrogen. The reaction mixture was stirred at room temperature for 17 h. This was poured onto water and extracted with ethyl acetate. The extracts was washed with 2N HCl, brine, dried (MgSO$_4$), and concentrated to afford 7.38 g as a brown oil. The crude material was used for next step directly.

$^1$H-NMR (CDCl$_3$) δ: 7.88–7.80 (2H, m), 7.49–7.43 (1H, m), 2.63 (3H, s).

4-(1-(6-Aminosulfonyl-3-pyridinyl)-3-trifluoromethyl-1H-pyrazol-5-yl)-2-fluorophenyl Trifluoromethanesulfonate (Step 3)

To a stirred solution of hexamethyldisilazane (6.4 ml, 30.36 mmol) in tetrahydrofuran (65 ml) was added n-butyllithium (19.3 ml, 30.36 mmol) dropwise at 0° C. under nitrogen. The reaction mixture was stirred at 0° C. for 30 min. Then cooled to −78° C., to the mixture was added a solution of 4-acetyl-2-fluorophenyltrifluoromethanesulfonate (7.24 g, 25.30 mmol) in tetrahydrofuran (30 ml) dropwise and stirred at −78° C. for 1 h. Then 1-trifluoroacetylimidazole (3.5 ml, 30.36 mmol) was added to the mixture at same temperature and the mixture was stirred at −78° C. for 3 h. This was quenched by water and the pH was adjusted to pH 4–5, extracted with ethyl acetate. The extracts was dried (MgSO$_4$) and concentrated. This was purified on silica gel eluting with ethyl acetate/hexane (1:10/1:8/1:4) to afford 2-fluoro-4-(4,4,4-trifluoro-3-oxobutanoyl)phenyltrifluoromethanesulfonate (3.0 g) as a red oil. A mixture of 2-Fluoro-4-(4,4,4-trifluoro-3-oxobutanoyl)phenyltrifluoromethanesulfonate (1.0 g, 2.62 mmol) and 5-hydrazino-2-pyridinesulfonamide hydrochloride (823 mg, 3.66 mmol) in ethanol (35 ml) was stirred at reflux for 15 h. After cooling, the solvent was removed and the residue was diluted with ethyl acetate, washed with water. The extracts was dried (MgSO$_4$) and concentrated. This was purified on silica gel eluting with ethyl acetate/hexane (1:10/1:8/1:6/1:3) to afford 886 mg_(63.3%) of the titled compound as a white amorphous.

$^1$H-NMR (CDCl$_3$) δ: 8.66 (1H, d, J=2.5 Hz), 8.08 (1H, d, J=8.4 Hz), 7.88 (1H, dd, J=8.4, 2.5 Hz), 7.46–7.40 (1H, m), 7.31–7.25 (1H, m), 7.13–7.10 (1H, m), 6.90 (1H, s), 6.28 (2H, br.s).

5-(5-(3-Fluoro-4-(1,3-thiazol-5-yl)phenyl)-3-trifluoromethyl-1H-pyrazol-1-yl)-2-pyridinesulfonamide (Step 4)

A mixture of 4-(1-(6-aminosulfonyl-3-pyridinyl)-3-trifluoromethyl-1H-pyrazol-5-yl)-2-fluorophenyltrifluoromethanesulfonate (440 mg, 0.823 mmol), 5-tributylstannyl-1,3-thiazol (370 mg, 0.988 mmol), tetrakis(triphenylphosphine)palladium (95 mg, 0.082 mmol), lithium chloride (87 mg, 2.058 mmol) in 1,4-dioxane (10 ml) was stirred at reflux for 16 h. After cooling, the mixture was diluted with ethyl acetate, washed with water. The organic layer was dried (MgSO$_4$) and concentrated. This was purified on silica gel eluting with ethyl acetate/hexane (1:3/1:2) to afford 236 mg (61.1%) of the titled compound as a white solid.

$^1$H-NMR (CDCl$_3$) δ: 8.91 (1H, s), 8.69–8.68 (1H, m), 8.32 (1H, s), 8.07 (1H, dd, J=8.4, 0.7 Hz), 7.93 (1H, dd, J=8.6, 2.5 Hz), 7.67 (1H, t, J=7.7 Hz), 7.18 (1H, dd, J=10.9, 1.6 Hz), 7.06 (1H, dd, J=8.1, 1.8 Hz), 6.89 (1H, s), 6.08 (2H, s).

5-(5-(3-Fluoro-4-(1,3-thiazol-5-yl)phenyl)-3-trifluoromethyl-1H-pyrazol-1-yl)-2-pyridinesulfonamide Hydrochloride (Step 5)

5-(5-(3-Fluoro-4-(1,3-thiazol-5-yl)phenyl)-3-trifluoromethyl-1H-pyrazol-1-yl)-2-pyridinesulfonamide (236 mg, 0.50 mmol) was dissolved with HCl—MeOH and the solvent was removed. The residue was washed with ethyl acetate to afford 233 mg (92.1%) of the titled compound as a slight yellow solid.

$^1$H-NMR (DMSO) δ: 9.26 (1H, s), 8.79 (1H, d, J=1.8 Hz), 8.48 (1H, s), 8.13 (1H, dd, J=8.6, 2.5 Hz), 8.04 (1H, d, J=8.4 Hz), 7.95 (1H, t, J=8.1 Hz), 7.66 (2H, br.s), 7.57–7.52 (1H, m), 7.46 (1H, s), 7.27 (1H, dd, J=8.1, 1.8 Hz); IR (KBr) ν: 1736, 1474, 1394, 1342, 1242, 1177, 1144, 974 cm$^{-1}$; mp: 173–176° C.

Example 16

5-[4-Chloro-5-[3-chloro-4-(1,3-thiazol-5-yl)phenyl]-3-trifluoromethyl-1H-pyrazol-1-yl]-2-pyridinesulfonamide 1-[4-(tert-Butyldimethylsilyloxy)-3-chlorophenyl]-2-chloro-4,4,4-trifluoro-1,3-butanedione (Step 1)

To a solution of 1-(4-tert-Butyldimethylsilyloxy)-3-chlorophenyl-4,4,4-trifluoro-1,3-butanedione (from step 2 of Example 12, 1.9 g, 5 mmol) in CH$_2$Cl$_2$ (15 mL) was added SO$_2$Cl$_2$ (680 mg, 5 mmol) in CH$_2$Cl$_2$ (5 mL) at 0° C. and the mixture was stirred for 30 min at room temperature. The mixture was added 10% aqueous K$_2$CO$_3$ (25 mL) and stirred 5 min. The mixture was acidified by the addition of 2N aqueous HCl and extracted with CH$_2$Cl$_2$ (30 mL×3), dried over MgSO$_4$, and concentrated in vacuo gave orange color oil. (1.3 g) This was used next step without further purification.

5-[4-Chloro-5-(3-chloro-4-hydroxyphenyl)-3-trifluoromethyl-1H-pyrazol-1-yl]-2-pyridinesulfonamide (Step 2)

The title compound was prepared according to the procedure of Example 12 step 3 using 1-[4-(tert-butyldimethylsilyloxy)-3-chlorophenyl]-2-chloro-4,4,4-trifluoro-1,3-butanedione instead of 1-(4-tert-butyldimethylsilyloxy)-3-chlorophenyl-4,4,4-trifluoro-1,3-butanedione. This was used next step without further purification.

MS (EI): m/z 452 (M$^+$).

[4-[1-[6-(Aminosulfonyl)-3-pyridinyl]-4-chloro-3-(trifluoromethyl)-1H-pyrazol-5-yl]-2-chlorophenyl] trifluoromethanesulfonate (Step 3)

The title compound was prepared according to the procedure of step 4 of Example 12 step 4 using 5-[4-chloro-5-(3-chloro-4-hydroxyphenyl)-3-trifluoromethyl-1H-pyrazol-1-yl]-2-pyridinesulfonamide instead of 5-[5-(3-chloro-4- hydroxyphenyl)-3-trifluoromethyl-1H-pyrazol-1-yl]-2-pyridinesulfonamide.

$^1$H-NMR (CDCl$_3$) δ: 8.62 (m, 1H), 8.07 (d, J=8.4 Hz, 1H), 7.83 (m, 1H), 7.59 (d,J=1.8 Hz, 1H), 7.49 (d,J=8.4 Hz, 1H), 7.57–7.40 (m, 1H), 5.10 (s, 2H).

5-[4-Chloro-5-[3-chloro-4-(1,3-thiazol-5-yl)phenyl]-3-trifluoromethyl-1H-pyrazol-1-yl]-2-pyridinesulfonamide (Step 4)

The title compound was prepared according to the procedure of Example 15 step 4 using [4-[1-[6-(aminosulfonyl)-3-pyridinyl]-4-chloro-3-(trifluoromethyl)-1H-pyrazol-5-yl]-2-chlorophenyl]trifluoromethanesulfonate instead of 4-(1-(6-aminosulfonyl-3-pyridinyl)-3-trifluoromethyl-1H-pyrazol-5-yl)-2-fluorophenyltrifluoromethanesulfonate.

mp: 191–193° C. $^1$H-NMR (CDCl$_3$) δ: 8.94 (s, 1H), 8.65 (d, J=2.5 Hz, 1H), 8.21 (s, 1H), 8.08 (d, J=8.4 Hz, 1H), 7.92 (dd, J=2.5, 8.4 Hz, 1H), 7.64 (d, J=7.9 Hz, 1H), 7.56 (d, J=1.8 Hz, 1H), 7.18 (dd, J=1.6, 8.0 Hz, 1H), 5.13 (s, 214). Anal. Calcd. for C$_{18}$H$_{10}$N$_5$O$_2$F$_3$Cl$_2$S$_2$: C, 41.55; H, 1.94; N, 13.46. Found: C, 41.62; H, 2.15; N, 12.58.

Example 17

6-[5-[3-Methyl-4-(1,3-thiazol-4-yl)phenyl]-3-(trifluoromethyl)-1H-pyrazol-1-yl]-3-pyridinesulfonamide Hydrochloride 2-Bromo-1-(4-hydroxy-2-methylphenyl)-1-ethanone (Step 1)

To a stirred solution of 4'-hydroxy-2'-methylacetophenone (4.5 g, 30.0 mmol) in dioxane (7 ml) was added a solution of bromine (4.87 g, 30.5 mmol) in dioxane (28 ml) dropwise at room temperature. After addition, the mixture was stirred at room temperature for 30 minutes. The volatile was evaporated in vacuo, and the residue was used for next reaction without further purification. (5.57 g, 81% yield).

$^1$H-NMR (CDCl$_3$) δ: 7.71 (d, J=9 Hz, 1H), 6.76–6.71 (m, 2H), 5.71 (s, 1H), 4.40 (s, 2H), 2.55 (s, 3H).

3-Methyl-4-(1,3-thiazol-4-yl)phenol (Step 2)

To a stirred solution of phosphorus pentasulfide (6.0 g, 13.5 mmol) in dioxane (60 ml) was added formamide (7.2 g, 160 mmol), and the mixture was heated at reflux temperature for 2 hours. The reaction mixture was cooled down to room temperature, and the solution was decanted away from solids. To a stirred solution of 2-bromo-1-(4-hydroxy-2-methylphenyl)-1-ethanone from step 1 (2.4 g, 10.5 mmol) in dioxane (20 ml) was added the thioformamide solution, and the mixture was heated at reflux temperature for 6 hours. The reaction mixture was cooled down to room temperature, and made basic by addition of 0.5M NaOH aqueous solution. The whole was extracted with ethyl acetate. The organic layer was washed with brine, dried over MgSO$_4$, and concentrated in vacuo. The residue was purified by flash chromatography eluting with ethyl acetate-hexane (1:4) to give title compound (1.54 g, 77% yield).

$^1$H-NMR (DMSO-d$_6$) δ: 9.46 (s, 1H), 9.10 (d, J=2 Hz, 1H), 7.59 (d, J=2 Hz, 1H), 7.39 (d, J=8 Hz, 1H), 6.67–6.61 (m, 2H), 2.30 (s, 3H).

3-Methyl-4-(1,3-thiazol-4-yl)phenyl Trifluoromethanesulfonate (Step 3)

To a stirred solution of 3-methyl-4-(1,3-thiazol-4-yl) phenol from step 2 (1.54 g, 8.05 mmol) in CH$_2$Cl$_2$ (48 ml) was added 2,6-lutidine (1.04 g, 9.66 mmol), 4-dimethylaminopyridine (0.20 g, 1.61 mmol), trifluoromethanesulfonic anhydride (2.73 g, 9.66 mmol) at −30° C. under nitrogen, and the mixture was stirred for 1 hour, and then allowed to warm up to room temperature for 2 hours. The reaction mixture was diluted with water and the whole was extracted with CH$_2$Cl$_2$. The organic layer was washed with brine, dried over MgSO$_4$, and concentrated in vacuo, and the residue was used for next reaction without further purification. (2.60 g, 99% yield).

Mass (m/e) 323 (M$^+$).

1-[3-Methyl-4-(1,3-thiazol-4-yl)phenyl]-1-ethanone (Step 4)

To a stirred solution of 3-methyl-4-(1,3-thiazol-4-yl) phenyl trifluoromethanesulfonate from step 3 (2.60 g, 8.05 mmol) in dioxane (75 ml) was added tributyl(1-ethoxyvinyl) tin (3.5 g, 9.66 mmol), tetrakis(triphenylphosphine) palladium (930 mg, 0.805 mmol), lithium chloride (850 mg, 20.0 mmol), and the mixture was heated at reflux temperature for 8 hours. The reaction mixture was cooled down to room temperature, and diluted with ethyl acetate. The whole was washed with saturated potassium fluoride aqueous solution, and the precipitate was removed by filteration through celite. The resulting solution was extracted with ethyl acetate. The organic layer was concentrated in vacuo. To the residue was added THF (50 ml), 2N HCl aqueous solution (50 ml), and the mixture was heated at reflux temperature for 8 hours. The reaction mixture was cooled down to room temperature, made neutral by addition of NaHCO$_3$, and extracted with ethyl acetate. The organic layer was washed with brine, dried over MgSO$_4$, and concentrated in vacuo. The residue was purified by flash chromatography eluting with ethyl acetate-hexane (1:5) to give title compound (714 mg, 41% yield).

$^1$H-NMR (CDCl$_3$) δ: 8.92 (d, J=2 Hz, 1H), 7.89–7.84 (m, 2H), 7.74 (d, J=8 Hz, 1H), 7.44 (d, J=2 Hz, 1H), 2.64 (s, 3H), 2.53 (s, 3H).

4,4,4-Trifluoro-1-[3-methyl-4-(1,3-thiazol-4-yl)phenyl]-1,3-butanedione (Step 5)

To a stirred solution of ethyl trifluoroacetate (500 mg, 3.52 mmol) in tert-butyl methyl ether (4 ml) was added sodium methoxide (28 wt.% solution in methanol; 0.9 ml, 4.0 mmol) over 2 min. A solution of 1-[3-methyl-4-(1,3-thiazol-4-yl)phenyl]-1-ethanone from step 4 (714 mg, 3.33 mmol) in t-butylmethylether (6 ml) was added dropwise over 5 minutes, and the mixture was stirred for 20 hours. 2N HCl (10 ml) was added, and the whole was extracted with ethyl acetate. The organic layer was washed with brine, dried over MgSO$_4$, and concentrated in vacuo, and the residue was used for next reaction without further purification. (1.05 g, 99% yield).

$^1$H-NMR (CDCl$_3$) δ: 8.93 (d, J=2 Hz, 1H), 7.88–7.78 (m, 3H), 7.49 (d, J=2 Hz, 1H), 6.61 (s, 1H), 2.56 (s, 3H).

5-[3-Methyl-4-(4-thiazolyl)phenyl]-1-[2-(5-sulfamoyl) pyridyl]-3-trifluoromethyl-1H-pyrazole (Step 6)

The title compound was prepared according to the procedure of Example 1, step 2 using 4,4,4-trifluoro-1-[3-methyl-4-(4-thiazolyl)phenyl]butane-1,3-dione instead of 4,4,4-trifluoro-1-[4-(2-furyl)phenyl]butane-1,3-dione.

mp: 142.0–143.0° C. $^1$H-NMR (CDCl$_3$) δ: 8.91 (d, J=2 Hz, 1H), 8.80 (d, J=2 Hz, 1H), 8.30 (dd, J=3, 9 Hz, 1H), 7.87 (d, J=9 Hz, 1H), 7.59 (d, J=8 Hz, 1H), 7.41 (d, J=2 Hz, 1H), 7.29–7.26 (m, 1H), 7.09 (d, J=8 Hz, 1H), 6.80 (s, 1H), 5.26

(brs, 2H), 2.45 (s, 3H). Anal.Calcd.for.$C_{19}H_{14}F_3N_5O_2S_2$: C, 49.03; H, 3.03; N, 15.05. Found: C, 48.95; H, 3.36; N, 14.68. MS (EI): m/z 465 ($M^+$).

5-[3-Methyl-4-(4-thiazolyl)phenyl]-1-[2-(5-sulfamoyl) pyridyl]-3-trifluoromethyl-1H-pyrazole Hydrochloride. (Step 7)

5-[3-Methyl-4-(4-thiazolyl)phenyl]-1-[2-(5-sulfamoyl) pyridyl]-3-trifluoromethyl-1H-pyrazole(0.1 g, 0.21 mmol) was dissolved in 10% methanolic HCl (2 mL), and volatiles were removed by evaporation. The residue was recrystallized from methanol/dichloromethane to give the title compound (0.09 g, 85.7% yield).

mp: 138.0–140.0° C. $^1$H-NMR (DMSO-$d_6$) δ: 9.22 (d, J=2 Hz, 1H), 8.73 (d, J=2 Hz, 1H), 8.45 (dd, J=2, 9 Hz, 1H), 8.02 (d, J=9 Hz, 1H), 7.94 (d, J=2 Hz, 1H), 7.76 (brs, 2H), 7.62 (d, J=8 Hz, 1H), 7.41 (brs, 1H), 7.33 (s, 1H), 7.13 (d, J=8 Hz, 1H), 2.42 (s, 3H). Anal.Calcd.for.$C_{19}H_{14}F_3N_5O_2S_2$, HCl,0.7H$_2$O: C, 44.35; H, 3.21; N, 13.61. Found: C, 44.02; H, 3.26; N, 13.37. MS (EI): m/z 465 ($M^+$).

Example 18

5-[5-[3-Methyl-4-(1,3-thiazol-4-yl)phenyl]-3-trifluoromethyl-1H-pyrazol-1-yl]-2-pyridinesulfonamide Hydrochloride The title compound was prepared according to the procedure of Example 17 using 5-hydrazino-2-pyridinesulfonamide hydrochloride (Example 6) instead of 2-hydrazino-5-pyridinesulfonamide dihydrochloride.

mp: amorphous $^1$H-NMR (DMSO-$d_6$) δ: 9.21 (d, J=2.0 Hz, 1H), 8.73 (d, J=2.5 Hz, 1H), 8.12 (dd, J=2.5, 8.4 Hz, 1H), 8.01 (d, J=8.4 Hz, 1H), 7.95 (d, J=1.8 Hz, 1H), 7.64 (d, J=8.1 Hz, 1H), 7.62 (br s, 2H), 7.43 (s, 1H), 7.34 (s, 1H), 7.17 (d, J=8.1 Hz, 1H), 2.48 (s, 3H). Anal. Calcd. for $C_{19}H_{15}N_5O_2F_3ClS_2$: C, 45.47; H, 3.01; N, 13.95. Found: C, 45.83; H, 3.52; N, 13.19.

Example 19

5-(4-Ethyl-5-(3-fluoro-4-(1,3-thiazol-4-yl)phenyl)-3-trifluoromethyl-1H-pyrazol-1-yl)-2-pyridinesulfonamide 4-Bromo-3-fluorobenzoic acid (Step 1)

A mixture of 4-bromo-3-fluorotoluene (15.0 g, 79.35 mmol) and sodium hydroxide (3.3 g, 82.53 mmol) in pyridine (80 ml) and water (160 ml) was stirred at reflux. Potassium permanganese (52.7 g, 333.28 mmol) was added to the mixture over 30 min. The resulting suspension was heated at reflux for 3 h. The mixture was filtered through celite. The celite was washed with hot water, followed by ethyl acetate. The cooled aqueous layer was acidified to pH 1 with conc.HCl and extracted with ethyl acetate. The extracts was dried (MgSO$_4$) and concentrated to afford 15.0 g (86.3%) of the titled compound as a white crystal. The compound was used for the next reaction directly.

$^1$H-NMR (CDCl$_3$) δ: 7.81–7.71 (2H, m), 7.65–7.60 (1H, m).

4-Bromo-3-fluoro-N-methoxy-N-methylbenzamide (Step 2)

To a stirred solution of 4-bromo-3-fluorobenzoic acid (5.0 g, 22.83 mmol) in dichloromethane (100 ml) was added WSC (8.8 g, 45.66 mmol), N,O-dimethylhydroxylamine hydrochloride (4.5 g, 45.66 mmol) and stirred at room temperature for 5 h. The solvent was removed and the residue was diluted with ethyl acetate. The organic layer was washed with water, dried (MgSO$_4$), and concentrated to afford 5.47 g of the titled compound as a yellow oil. The compound was used for the next reaction directly.

$^1$H-NMR (CDCl$_3$) δ: 7.63–7.58 (1H, m), 7.53–7.49 (1H, m), 7.43–7.39 (1H, m), 3.55 (3H, s), 3.37 (3H, s).

1-(4-Bromo-3-fluorophenyl)-1-butanone (Step 3)

To a stirred solution of 4-Bromo-3-fluoro-N-methoxy-N-methylbenzamide (3.0 g, 12.19 mmol) in tetrahydrofuran (35 ml) was added 2M n-propylmagnesium bromide (12.2 ml, 24.38 mmol) dropwise under nitrogen at 0° C. The reaction mixture was stirred at room temperature for 2 h. This was quenched by sat. ammonium chloride and stirred at rt for 30 min. The organic layer was separated and the aqueous layer was extracted with ethyl acetate. The extracts was dried (MgSO$_4$) and concentrated. This was purified on silica gel eluting with ethyl acetate/hexane (1:10) to afford 2.44 g (81.7%) of the titled compound as a slight yellow oil.

$^1$H-NMR (CDCl$_3$) δ: 7.71–7.59 (3H, m), 2.90 (2H, t, J=7.4 Hz), 1.77 (2H, m), 1.00 (3H, t, J=7.4 Hz).

5-(5-(4-Bromo-3-fluorophenyl)-4-ethyl-3-trifluoromethyl-1H-pyrazol-1-yl)-2-pyridinesulfonamide (Step 4)

To a stirred solution of hexamethyldisilazane (2.5 ml, 11.75 mmol) in tetrahydrofuran (25 ml) was added n-butyllithium (7.5 ml, 11.75 mmol) dropwise at 0° C. under nitrogen. The reaction mixture was stirred at room temperature for 30 min. Then cooled to −78° C., to the mixture was added a solution of 1-(4-bromo-3-fluorophenyl)-1-butanone (2.4 g, 9.79 mmol) in tetrahydrofuran (12 ml) dropwise and stirred at rt for 1 h. Then 1-trifluoroacetylimidazole (1.3 ml, 11.75 mmol) was added to the mixture at same temperature, the mixture was stirred at rt for 5 h. This was quenched by water and the pH was adjusted to pH 4–5, extracted with ethyl acetate. The extracts was dried (MgSO$_4$) and concentrated. This was purified on silica gel eluting with ethyl acetate/hexane (1:20/1:15) to afford 2.7 g (80.9%) as a yellow oil. A mixture of 1-(4-bromo-3-fluorophenyl)-2-ethyl-4,4,4-trifluoro-1,3-butanedione (1.5 g, 4.40 mmol) and 5-hydrazino-2-pyridinesulfonamide hydrochloride (1.28 g, 5.72 mmol) in ethanol (60 ml) was stirred at reflux for 3 h. After cooling, the solvent was removed and the residue was diluted with ethyl acetate, washed with water. The extracts was dried (MgSO$_4$) and concentrated. This was purified on silica gel eluting with ethyl acetate/hexane (1:10/1:5/1:4) to afford 1.64 g (75.6%) of the titled compound as a white amorphous.

$^1$H-NMR (CDCl$_3$) δ: 8.58–8.57 (1H, m), 7.99–7.95 (1H, m), 7.79 (1H, dd, J=8.6, 2.5 Hz), 7.70–7.64 (1H, m), 7.05 (1H, dd, J=8.6, 1.8 Hz), 6.91–6.88 (1H, m), 5.40 (2H, br.s), 2.56 (2H, q, J=7.6H), 1.14 (3H, t, J=7.6 Hz).

5-(4-Ethyl-5-(3-fluoro-4-(1,3-thiazol-4-yl)phenyl)-3-trifluoromethyl-1H-pyrazol-1-yl)-2-pyridinesulfonamide (Step 5)

A mixture of 5-(5-(4-bromo-3-fluorophenyl)-4-ethyl-3-trifluoromethyl-1H-pyrazol-1-yl)-2-pyridinesulfonamide (450 mg, 0.912 mmol), 4-tributylstannyl-1,3-thiazol (410 mg, 1.095 mmol), tetrakis(triphenylphosphine)palladium (105 mg, 0.091 mmol), lithium chloride (97 mg, 2.281 mmol) in 1,4-dioxane (11 ml) was stirred at reflux for 17 h. After cooling, the mixture was diluted with ethyl acetate, washed with water. The organic layer was dried (MgSO$_4$) and concentrated. This was purified on silica gel eluting with ethyl acetate/hexane (1:3/1:2) to afford 350 mg (77.1%) of the titled compound as a yellow solid.

¹H-NMR (CDCl₃) δ: 8.91–8.90 (1H, m), 8.61–8.60 (1H, m), 8.39–8.33 (1H, m), 7.97–7.92 (2H, m), 7.85–7.80 (1H, m), 7.14–7.05 (2H, m), 5.28 (2H, br.s), (2H, q, J=7.6 Hz), 1.16 (3H, t, J=7.6 Hz); IR (KBr) ν: 1470,1448, 1354,1292, 1178, 1157, 1128, 1076 cm⁻¹; mp: 182–185° C.

Example 20

5-(4-Ethyl-5-(3-fluoro-4-(1,3-thiazol-5-yl)phenyl)-3-trifluoromethyl-1H-pyrazol-1-yl)-2-pyridinesulfonamide 5-(4-Ethyl-5-(3-fluoro-4-(1,3-thiazol-5-yl)phenyl)-3-trifluoromethyl-1H-pyrazol-1-yl)-2-pyridinesulfonamide (Step 1)

A mixture of 5-(5-(4-bromo-3-fluorophenyl)-4-ethyl-3-trifluoromethyl-1H-pyrazol-1-yl)-2-pyridinesulfonamide from step 4 of Example 19 (450 mg, 0.912 mmol), 5-tributylstannyl-1,3-thiazol (410 mg, 1.095 mmol), tetrakis (triphenylphosphine)palladium (105 mg, 0.091 mmol), lithium chloride (97 mg, 2.281 mmol) in 1,4-dioxane (11 ml) was stirred at reflux for 5 h. After cooling, the mixture was diluted with ethyl acetate, washed with water. The organic layer was dried (MgSO₄) and concentrated. This was purified on silica gel eluting with ethyl acetate/hexane (1:3/1:2) to afford 220 mg (48.5%) of the titled compound as a slight yellow solid.

¹H-NMR (CDCl₃) δ: 8.92 (1H, s), 8.58 (1H, d, J=2.6 Hz), 8.33 (1H, s), 8.00 (1H, d, J=8.4 Hz), 7.85 (1H, dd, J=8.4, 2.4 Hz), 7.73 (1H, t, J=7.7 Hz), 7.15–7.06 m), 6.26 (2H, br.s), 2.60 (2H, q, J=7.7 Hz), 1.17 (3H, t, J=7.7 Hz). IR (KBr) ν: 1564, 1472, 1445, 1331, 1285, 1074, 835 cm⁻¹; mp: 189–191° C.

Example 21

5-(5-(3-Fluoro-4-(1,3-thiazol-4-yl)phenyl)-3-trifluoromethyl-1H-pyrazol-1-yl)-2-pyridinesulfonamide Hydrochloride 1-(2-Fluoro-4-hydroxyphenyl)-1-ethanone (Step 1)

To a stirred suspension of aluminum chloride (42 g, 312 mmol) in 1,2-dichloroethane (100 ml) was added 3-fluorophenol (31 g, 276 mmol) dropwise at 0° C. After addition, acetyl chloride (24 g, 306 mmol) was added dropwise and then the mixture was heated at reflux temperature for 16 hours. The mixture was cooled down to room temperature, and poured into ice. The whole was extracted with diethylether. The organic layer was washed with brine, dried over MgSO₄, and concentrated in vacuo. The residue was recystallized with hexane to give title compound (3.57 g, 8% yield).

¹H-NMR (CDCl₃) δ: 7.88–7.82 (m, 1H), 6.74 (dd, J=9, 2 Hz, 1H), 6.64 (dd, J=13, 2 Hz, 1H), 2.62 (d, J=5 Hz, 3H).

2-Bromo-1-(2-fluoro-4-hydroxyphenyl)-1-ethanone (Step 2)

To a stirred solution of 1-(2-fluoro-4-hydroxyphenyl)-1-ethanone (2.56 g, 16.6 mmol) in dioxane (4 ml) was added a solution of bromine (2.70 g, 16.9 mmol) in dioxane (15 ml) dropwise, and the mixture was stirred at room temperature for 3 hours. The volatile was evaporated in vacuo, and the residue was used for next reaction without further purification. (2.4 g, 62% yield).

¹H-NMR (CDCl₃) δ: 7.95–7.89 (m, 1H), 6.73 (dd, J=9, 2 Hz, 1H), 6.63 (dd, J=13, 3 Hz, 1H), 5.96 (s, 1H), 4.48 (d, J=3 Hz, 2H).

3-Fluoro-4-(1,3-thiazol-4-yl)phenol (Step 3)

To a stirred solution of phosphorus pentasulfide (4.0 g, 9.0 mmol) in dioxane (40 ml) was added formamide (4.8 g, 106 mmol), and the mixture was heated at reflux temperature for 2 hours. The reaction mixture was cooled down to room temperature, and the solution was decanted away from solids. To a stirred solution of 2-bromo-1-(2-fluoro-4-hydroxyphenyl)-1-ethanone (1.2 g, 5.15 mmol) in dioxane (14 ml) was added the thioformamide solution, and the mixture was heated at reflux temperature for 6 hours. The reaction mixture was cooled down to room temperature, and made basic by addition of 2N NaOH aqueous solution. The whole was extracted with ethyl acetate. The organic layer was washed with brine, dried over MgSO₄, and concentrated in vacuo. The residue was purified by flash chromatography eluting with ethyl acetate-exane (1:4) to give title compound (864 mg, 86% yield).

¹H-NMR (DMSO-d₆) δ: 10.03 (s, 1H), 9.04 (d, J=2 Hz, 1H), 7.89–7.83 (m, 1H), 7.67–7.64 (m, 1H), 6.64–6.53 (m, 2H).

3-Fluoro-4-(1,3-thiazol-4-yl)phenyl Trifluoromethanesulfonate (Step 4)

To a stirred solution of 3-fluoro-4-(1,3-thiazol-4-yl) phenol (864 mg, 4.43 mmol) in CH₂Cl₂ (27 ml) was added 2,6-lutidine (570 mg, 5.32 mmol), 4-dimethylaminopyridine (108 mg, 0.89 mmol), trifluoromethanesulfonic anhydride (1.5 g, 5.32 mmol) at −30° C. under nitrogen, and the mixture was stirred for 1 hour, and then allowed to warm up to room temperature for 2 hours. The reaction mixture was diluted with water and the whole was extracted with CH₂Cl₂. The organic layer was washed with brine, dried over MgSO₄, and concentrated in vacuo, and the residue was used for next reaction without further purification. (1.45 g, 99% yield).

1-[3-Fluoro-4-(1,3-thiazol-4-yl)phenyl]-1-ethanone (Step 5)

To a stirred solution of 3-fluoro-4-(1,3-thiazol-4-yl) phenyl trifluoromethanesulfonate (1.45 g, 4.43 mmol) in dioxane (42 ml) was added tributyl(1-ethoxyvinyl)tin (1.92 g, 5.32 mmol), tetrakis(triphenylphosphine) palladium (512 mg, 0.44 mmol), lithium chloride (466 mg, 11.0 mmol), and the mixture was heated at reflux temperature for 16 hours. The reaction mixture was cooled down to room temperature, and diluted with ethyl acetate. The whole was washed with saturated potassium fluoride aqueous solution, and the precipitate was removed by filteration through celite. The resulting solution was extracted with ethyl acetate. The organic layer was concentrated in vacuo. To the residue was added THF (20 ml), 2N HCl aqueous solution (20 ml), and the mixture was heated at reflux temperature for 8 hours. The reaction mixture was cooled down to room temperature, made neutral by addition of NaHCO₃, and extracted with ethyl acetate. The organic layer was washed with brine, dried over MgSO₄, and concentrated in vacuo. The residue was purified by flash chromatography eluting with ethyl acetate-hexane (1:5) to give title compound (666 mg, 68% yield).

¹H-NMR (CDCl₃) δ: 8.90–8.89 (m, 1H), 8.41–8.35 (m, 1H), 7.99–7.97 (m, 1H), 7.83 (dd, J=8, 2 Hz, 1H), 7.75 (dd, J=12, 2 Hz, 1H), 2.63 (s, 3H).

4,4,4-Trifluoro-1-[3-fluoro-4-(1,3-thiazol-4-yl)phenyl]-1,3-butanedione (Step 6)

To a stirred solution of 1-[3-fluoro-4-(1,3-thiazol-4-yl) phenyl]-1-ethanone (666 mg, 3.01 mmol), ethyl trifluoroacetate (470 mg, 3.31 mmol) in t-butylmethylether (40 ml) was added sodium methoxide (28 wt.% solution in methanol; 0.8 ml, 3.6 mmol) over 5 minutes, and the mixture was stirred for 20 hours. The mixture was made neutral by addition of 2N HCl, and the whole was extracted with ethyl acetate. The organic layer was washed with brine, dried over MgSO$_4$, and concentrated in vacuo. The residue was used for next reaction without further purification. (1.06 g, 99% yield).

5-(5-(3-Fluoro-4-(1,3-thiazol-4-yl)phenyl)-3-trifluoromethyl-1H-pyrazol-1-yl)-2-pyridinesulfonamide (Step 7)

A suspension of 4,4,4-trifluoro-1-(3-fluoro-4-(1,3-thiazol-4-yl)phenyl)-1,3-butanedione (503 mg, 1.59 mmol) and 5-hydrazino-2-pyridinesulfonamide hydrochloride (392 mg, 1.74 mmol) in ethanol (22 ml) was stirred at reflux for 28 h. After cooling, the solvent was removed and the residue was added water, extracted with ethyl acetate. The extracts was dried (MgSO$_4$) and concentrated. This was purified on silica gel eluting with ethyl acetate/hexane (1:4/1:3/1:2) to afford 172 mg (23.0%) of the titled compound as a yellow solid.

$^1$H-NMR (CDCl$_3$) δ: 8.89 (1H, d, J=1.6 Hz), 8.69 (1H, d, J=1.8 Hz), 8.30–8.24 (1H, m), 8.02–7.99 (1H, m), 7.91–7.86 (2H, m), 7.14–7.08 (2H, m), 6.88 (1H, s), 5.54 (2H, s).

5-(5-(3-Fluoro-4-(1,3-thiazol-4-yl)phenyl)-3-trifluoromethyl-1H-pyrazol-1-yl)-2-pyridinesulfonamide Hydrochloride (Step 8)

5-(5-(3-Fluoro-4-(1,3-thiazol-4-yl)phenyl)-3-trifluoromethyl-1H-pyrazol-1-yl)-2-pyridinesulfonamide (172 mg, 0.37 mmol) was dissolved with HCl-MeOH and the solvent was removed. The residue was washed with ethyl acetate to afford 120 mg (64.1%) of the titled compound as a slight yellow solid.

$^1$H-NMR (DMSO) δ: 9.27 (1H, d, J=1.5 Hz), 8.78–8.77 (1H, m), 8.21–8.02 (4H, m), 7.64 (2H, br.s), 7.49 (1H, dd, J=12.2, 1.5 Hz), 7.45 (1H, s), 7.28 (1H, dd, J=8.2, 1.8 Hz). IR (KBr) ν: 1474, 1342, 1240, 1178, 1136, 974 cm$^{-1}$; mp: amorphous Example 22

5-(5-(3-Chloro-4-(2-furyl)phenyl)-3-(trifluoromethyl)-1H-pyrazol-1-yl)-2-pyridinesulfonamide 3-Hydrazino-2-sulfamylpyridine hydrochloride(70 mg, 0.31 mmol) and 4,4,4-trifluoro-1-(3-dichloro-4-furylphenyl)-1,3-butanedione (100 mg, 0.32 mmol) were dissolved in ethanol (20 mL). The reaction mixture was refluxed overnight. The reaction mixture was cooled to room temperature, concentrated. The crude product was dissolved in EtOAc (100 mL) and washed with NaHCO$_3$ (saturated, 100 mL). The organic layer was dried (MgSO$_4$) and concentrated to give the crude solid. The crude product was purified by flash chromatography eluting with ethyl acetate/hexane (1/4) to provide the desired product as a white solid (127 mg, 85.8% yield).

The chemical structures of the compounds of Formula (I) prepared in the Examples 1 to 22, are summarized in the following table. In the table, "Fu" represents furyl, "Thz" represents 1,3-thiazolyl and "Oxz" represents oxazolyl.

Following formula [AX]

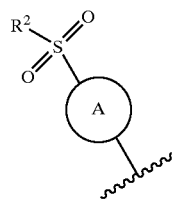

[AX] is a heteoaryl moiety selected from the group consisting of

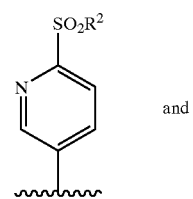   A11 and

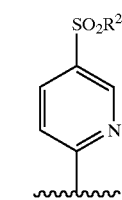   A12

TABLE

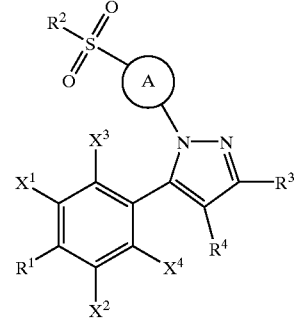

(I)

| Ex. # | A | R$^1$ | R$^2$ | R$^3$ | R$^4$ | X$^1$ | X$^2$ | X$^3$ | X$^4$ |
|---|---|---|---|---|---|---|---|---|---|
| 1 | A12 | 2-Fu | NH$_2$ | CF$_3$ | H | H | H | H | H |
| 2 | A11 | 2-Fu | NH$_2$ | CF$_3$ | H | H | H | H | H |
| 3 | A11 | 2-Oxz | NH$_2$ | CF$_3$ | H | H | Cl | H | H |
| 4 | A11 | 4-Thz | NH$_2$ | CF$_3$ | Cl | H | H | H | H |
| 5 | A11 | 4-Thz | NH$_2$ | CF$_3$ | H | H | CF$_3$ | H | H |
| 6 | A11 | 4-Thz | NH$_2$ | CF$_3$ | H | H | H | H | H |
| 7 | A11 | 4-Thz | NH$_2$ | CF$_3$ | CH$_3$CH$_2$ | H | H | H | H |
| 8 | A11 | 5-Thz | NH$_2$ | CF$_3$ | CH$_3$CH$_2$ | H | H | H | H |
| 9 | A11 | 4-Thz | NH$_2$ | CF$_3$ | F | H | H | H | H |
| 10 | A11 | 5-Thz | NH$_2$ | CF$_3$ | H | H | H | H | H |
| 11 | A11 | 5-Thz | NH$_2$ | CF$_3$ | F | H | H | H | H |
| 12 | A11 | 4-Thz | NH$_2$ | CF$_3$ | H | H | Cl | H | H |
| 13 | A11 | 5-Thz | NH$_2$ | CF$_3$ | H | Cl | Cl | H | H |
| 14 | A11 | 5-Thz | NH$_2$ | CF$_3$ | H | H | Cl | H | H |
| 15 | A11 | 5-Thz | NH$_2$ | CF$_3$ | H | H | F | H | H |
| 16 | A11 | 5-Thz | NH$_2$ | CF$_3$ | Cl | H | Cl | H | H |
| 17 | A12 | 4-Thz | NH$_2$ | CF$_3$ | H | H | CH$_3$ | H | H |
| 18 | A11 | 4-Thz | NH$_2$ | CF$_3$ | H | H | CH$_3$ | H | H |
| 19 | A11 | 4-Thz | NH$_2$ | CF$_3$ | CH$_3$CH$_2$ | H | F | H | H |
| 20 | A11 | 5-Thz | NH$_2$ | CF$_3$ | CH$_3$CH$_2$ | H | F | H | H |

TABLE-continued

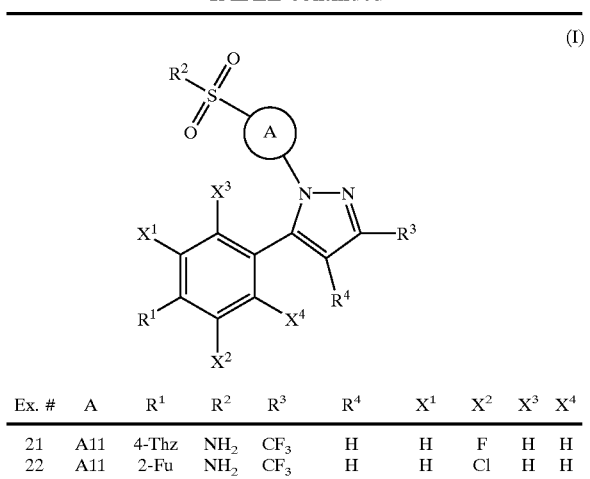

| Ex. # | A | R¹ | R² | R³ | R⁴ | X¹ | X² | X³ | X⁴ |
|---|---|---|---|---|---|---|---|---|---|
| 21 | A11 | 4-Thz | NH₂ | CF₃ | H | H | F | H | H |
| 22 | A11 | 2-Fu | 2-Fu | NH₂ | CF₃ | H | H | Cl | H | H |

What is claimed is:

1. A compound having the formula

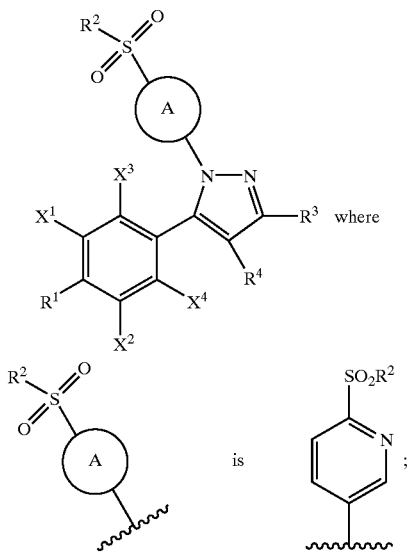 where $R^2\underset{O}{\overset{O}{\underset{\|}{\overset{\|}{S}}}}$—(A)— is $\underset{SO_2R^2}{\text{pyridine ring}}$ ;

$R^1$ is furyl, thiazolyl or oxazolyl;
$R^2$ is $NH_2$;
$R^3$ is trifluoromethyl;
$R^4$ is hydrogen, fluoro or ethyl;
$X^1$ and $X^2$ are independently hydrogen or chloro; and
$X^3$ and $X^4$ are hydrogen.

2. A compound according to claim 1 selected from the group consisting of 5-(5-(4-(2-furyl)phenyl)-3-(trifluoromethyl)-1H-pyrazol-1-yl)-2-pyridinesulfonamide;
5-(5-(3-chloro-4-(1,3-oxazol-2-yl)phenyl)-3-(trifluoromethyl)-1H-pyrazol-1-yl)-2-pyridinesulfonamide;
5-(4-chloro-5-(4-(1,3-thiazol-4-yl)phenyl)-3-(trifluoromethyl)-1H-pyrazol-1-yl)-2-pyridinesulfonamide;
5-(5-(4-(1,3-thiazol-4-yl)phenyl)-3-(trifluoromethyl)-1H-pyrazol-1-yl)-2-pyridinesul formamide;
5-(5-ethyl-(4-(1,3-thiazol-4-yl)phenyl)-3-(trifluoromethyl)-1H-pyrazol-1-yl)-2-pyridinesulfonamide;
5-(4-ethyl-5-(4-(1,3-thiazol-5-yl)phenyl)-3-(trifluoromethyl)-1H-pyrazol-1-yl)-2-pyridinesulfonamide;
5-(4-fluoro-5-(4-(1,3-thiazol-4-yl)phenyl)-3-(trifluoromethyl)-1H-pyrazol-1-yl)-2-pyridinesulfonamide;
5-(5-(4-(1,3-thiazol-5-yl)phenyl)-3-(trifluoromethyl)-1H-pyrazol-1-yl)-2-pyridinesulfonamide;
5-(4-fluoro-5-(4-(1,3-thiazol-5-yl)phenyl)-3-(trifluoromethyl)-1H-pyrazol-1-yl)-2-pyridinesulfonamide;
5-(5-chloro-(4-(1,3-thiazol-4-yl)phenyl)-3-(trifluoromethyl)-1H-pyrazol-1-yl)-2-pyridinesulfonamide;
5-(5-chloro-(4-(1,3-thiazol-5-yl)phenyl)-3-(trifluoromethyl)-1H-pyrazol-1-yl)-2-pyridinesulfonamide;
5-(4-chloro-5-(3-chloro-4-(1,3-thiazol-5-yl)phenyl)-3-(trifluoromethyl)-1H-pyrazol-1-yl)-2-pyridinesulfonamide;
5-(5-(3-methyl-4-(1,3-thiazol-4-yl)phenyl)-3-(trifluoromethyl)-1H-pyrazol-1-yl)-2-pyridinesulfonamide;
5-(4-ethyl-5-(3-fluoro-4-(1,3-thiazol-5-yl)phenyl)-3-(trifluoromethyl)-1H-pyrazol-1-yl)-2-pyridinesulfonamide;
5-(5-(3-chloro-4-(2-furyl)phenyl)-3-(trifluoromethyl)-1H-pyrazol-1-yl)-2-pyridinesulfonamide; and
salts thereof.

3. A compound according to claim 1 selected from the group consisting of 5-(5-(4-(2-furyl)phenyl)-3-(trifluoromethyl)-1H-pyrazol-1-yl)-2-pyridinesulfonamide;
5-(5-(3-chloro-4-(1,3-oxazol-2-yl)phenyl)-3-(trifluoromethyl)-1H-pyrazol-1-yl)-2-pyridinesulfonamide;
5-(4-ethyl-5-(4-(1,3-thiazol-5-yl)phenyl)-3-(trifluoromethyl)-1H-pyrazol-1-yl)-2-pyridinesulfonamide;
5-(4-fluoro-5-(4-(1,3-thiazol-4-yl)phenyl)-3-(trifluoromethyl)-1H-pyrazol-1-yl)-2-pyridinesulfonamide;
5-(5-(4-(1,3-thiazol-5-yl)phenyl)-3-(trifluoromethyl)-1H-pyrazol-1-yl)-2-pyridinesulfonamide;
5-(5-chloro-(4-(1,3-thiazol-4-yl)phenyl)-3-(trifluoromethyl)-1H-pyrazol-1-yl)-2-pyridinesulfonamide;
5-(5-chloro-4-(1,3-thiazol-5-yl)phenyl)-3-(trifluoromethyl)-1H-pyrazol-1-yl)-2-pyridinesulfonamide;
5-(5-(3-methyl-4-(1,3-thiazol-4-yl)phenyl)-3-(trifluoromethyl)-1H-pyrazol-1-yl)-2-pyridinesulfonamide;
5-(4-ethyl-5-(3-fluoro-4-(1,3-thiazol-5-yl)phenyl)-3-(trifluoromethyl)-1H-pyrazol-1-yl)-2-pyridinesulfonamide;
5-(5-(3-chloro-4-(2-furyl)phenyl)-3-(trifluoromethyl)-1H-pyrazol-1-yl)-2-pyridinesulfonamide; and
salts thereof.

* * * * *